(12) United States Patent
Wong et al.

(10) Patent No.: US 6,319,695 B1
(45) Date of Patent: Nov. 20, 2001

(54) PRODUCTION OF FUCOSYLATED CARBOHYDRATES BY ENZYMATIC FUCOSYLATION SYNTHESIS OF SUGAR NUCLEOTIDES; AND IN SITU REGENERATION OF GDP-FUCOSE

(75) Inventors: Chi-Huey Wong, Rancho Santa Fe; Yoshitaka Ichikawa, San Diego; Gwo-Jenn Shen, Carlsbad, all of CA (US); Kun-Chin Liu, New Haven, CT (US)

(73) Assignee: The Scripps Research Insitute, LaJolla, CA (US)

( * ) Notice: Subject to any disclaimer, the term of this patent is extended or adjusted under 35 U.S.C. 154(b) by 0 days.

(21) Appl. No.: 07/961,076

(22) Filed: Oct. 14, 1992

Related U.S. Application Data

(63) Continuation-in-part of application No. 07/910,612, filed on Jul. 8, 1992, now abandoned, which is a continuation-in-part of application No. 07/901,260, filed on Jun. 19, 1992, now abandoned, which is a continuation-in-part of application No. 07/777,662, filed on Oct. 15, 1991, now abandoned.

(51) Int. Cl.[7] ............................................. C12P 19/18
(52) U.S. Cl. ................................................ 435/97; 435/84
(58) Field of Search ................................. 435/84, 97

(56) References Cited

U.S. PATENT DOCUMENTS

| | | | |
|---|---|---|---|
| 4,137,401 | 1/1979 | Lemieux et al. | 536/116 |
| 4,235,871 | 11/1980 | Papahadjopoulos et al. | 424/19 |
| 4,501,728 | 2/1985 | Geho et al. | 424/38 |
| 4,563,445 | 1/1986 | Feizi et al. | 514/25 |
| 4,686,193 | 8/1987 | Kolar | 436/536 |
| 4,770,994 | 9/1988 | Rittenhouse | 435/7 |
| 4,837,028 | 6/1989 | Allen | 424/450 |
| 4,925,796 | * 5/1990 | Bergh et al. | 435/97 |
| 5,079,353 | 1/1992 | Ratcliffe et al. | 536/53 |
| 5,109,126 | 4/1992 | Agrawal et al. | 536/29 |
| 5,180,674 | * 1/1993 | Roth | 435/288 |
| 5,246,840 | 9/1993 | Nilsson . | |
| 5,264,352 | 11/1993 | Thiem et al. . | |
| 5,278,299 | 1/1994 | Wong et al. | 536/53 |
| 5,344,870 | 9/1994 | Ratcliffe et al. | 525/54.2 |

FOREIGN PATENT DOCUMENTS

| | | |
|---|---|---|
| 3626915 A1 | 2/1988 | (DE) . |
| WO87/05330 | * 9/1987 | (WO) . |
| WO 91/16449 | 10/1991 | (WO) . |

OTHER PUBLICATIONS

Foster, *J. Biol. Chem.*, 266:3526–3531 (1991).
Muramatsu, *Eur. J. Biochem.*, 157:71–75 (1986).
Prieels et al., *J. Biol. Chem.*, 256:10456–10463 (1981).
Campbell et al., *J. Biol. Chem.*, 259:11208–11214 (1984).
Larsen et al., *Proc. Natl. Acad. Sci., U.S.A.*, 87:6674–6678 (1990).
Kukowska–Latallo et al., *Genes and Devel.*, 4:1288–1303 (1990).
Ichikawa et al.,*J. Amer. Chem. Soc.*, 113:4698–4700 (1991).
Dumas et al., *Bioorg. & Med. Chem. Lett.*, 1:425 (1991).
Gokhale, *Can. J. Chem.*, 68:1063 (1990).
Phillips et al., *Science*, 250:1130–1132 (1990).
Palcic et al., *Glycobiology*, 1:205 (1991).
Wong et al., *J. Org. Chem.*, 47:5416 (1982).
Schachter et al., *Method Enzymol.*, 28:285 (1972).
Dumas et al., *Biorg. & Med. Chem. Lett.*, 2:33 (1992).
Ichikawa et al., *J. Am. Chem. Soc.*, 113:6300–6302 (1991).
Liu et al., *J. Org. Chem.*, 57:3748–3750 (1992).
Ichikawa et al., *J. Org. Chem.*, 57:2943–2946 (1992).
Borman, *C&EN*, pp. 25–28 (Dec. 7, 1992).
David et al., *Adv. in Carbohydr. Chem. and Biochem.*, 49:215–219 (1991).

* cited by examiner

Primary Examiner—Leon B. Lankford, Jr.
(74) *Attorney, Agent, or Firm*—Welsh & Katz, Ltd.

(57) ABSTRACT

This invention contemplates improved methods of enzymatic production of carbohydrates especially fucosylated carbohydrates. Improved syntheses of glycosyl 1- or 2-phosphates using both chemical and enzymatic means are also contemplated. The phosphorylated glycosides are then used to produce sugar nucleotides that are in turn used as donor sugars for glycosylation of acceptor carbohydrates. Especially preferred herein is the use of a disclosed method for fucosylation.

20 Claims, 3 Drawing Sheets

Figure 1:
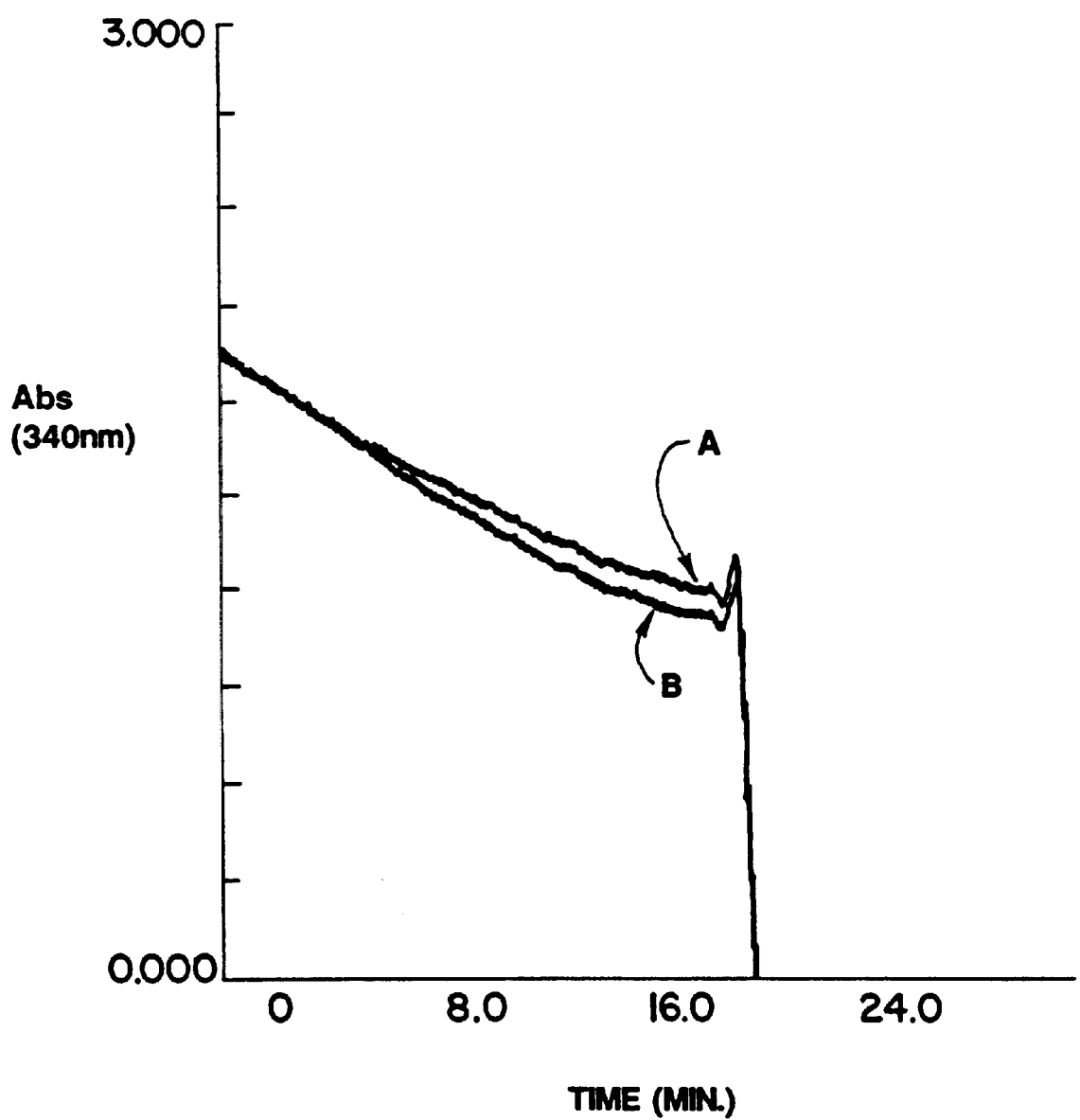

PRODUCTION OF FUCOSYLATED CARBOHYDRATES BY ENZYMATIC FUCOSYLATION SYNTHESIS OF SUGAR NUCLEOTIDES; AND IN SITU REGENERATION OF GDP-FUCOSE

CROSS-REFERENCE TO RELATED APPLICATIONS

This application is a continuation-in-part of U.S. patent application Ser. No. 07/910,612, filed Jul. 8, 1992, now abandoned, that is a continuation-in-part of U.S. patent application Ser. No. 07/901,260, filed Jun. 19, 1992, now abandoned, that is a continuation-in-part of U.S. patent application Ser. No. 07/777,662, filed Oct. 15, 1991, now abandoned, whose disclosures are incorporated herein by reference.

BACKGROUND OF THE INVENTION

1. Field of the Invention

This invention provides for improved methods of enzymatic production of carbohydrates especially fucosylated carbohydrates. The invention provides for improved synthesis of glycosyl 1- or 2-phosphates using both chemical and enzymatic means. These phosphorylated glycosides are then used to produce sugar nucleotides which are in turn used as donor sugars for glycosylation of acceptor carbohydrates. Especially preferred herein is the use of the disclosed methods for fucosylation.

2. Summary of the Invention

This invention provides for a method of producing a fucosylated carbohydrate in a single reaction mixture comprising the steps of: using a fucosyltransferase to form an O-glycosidic bond between a nucleoside 5'-diphosphofucose and an available hydroxyl group of a carbohydrate acceptor molecule to yield a fucosylated carbohydrate and a nucleoside 5'-diphosphate; and recycling in situ the nucleoside 5'-diphosphate with fucose to form the corresponding nucleoside 5'-diphospho-fucose. Preferred methods of this invention include the use of guanine as a base for the nucleoside, the use of catalytic amounts of nucleosides, the use of N-acetylglucosamine, galactose, N-acetylgalactosamine or N-acetyllactosamine as the carbohydrate acceptor molecule, and the use of a sialylated carbohydrate acceptor molecule.

This invention further contemplates the above method for producing fucosylated sialylated carbohydrate molecule through enzymatic formation of glycosidic linkages in a single reaction mixture comprising: forming a first glycosidic linkage between an diphosphonucleoside-activated glycosyl donor such as UDP-Gal and an available hydroxyl group of a carbohydrate acceptor molecule such as GlcNAc using a first glycosyltransferase such as β1,4-galactosyltransferase in preparing Galβ1,4GlcNAc; forming a second glycosidic linkage between a monophosphonucleoside-activated sialyl donor such as CMP-NeuAc and an available hydroxyl group of the sugar acceptor molecule such as the 3-position hydroxyl of the Gal of Galβ1,4GlcNAc using a sialyltransferase such as α2,3sialyltransferase; forming a third glycosidic linkage between a diphosphonucleoside-activated fucosyl donor such as GDP-Fuc and an available hydroxyl group of the sugar acceptor molecule such as the 3-position hydroxyl of the GlcNAc of Galβ1,4GlcNAc using a fucosyltransferase such as α1,3/4fucosyltransferase wherein at least one of steps (a) (b) or (c) further comprise the in situ formation of the phosphonucleotide-activated glycosyl donor from a catalytic amount of the corresponding monophosphate and diphosphate nucleoside. Especially preferred are methods of this invention wherein the fucosylated sialylated carbohydrate moiety product is a sialylated Lewis ligand such as sialyl Le$^x$ (SLe$^x$) or sialyl Le$^a$ (SLe$^a$) and wherein the fucose is transferred from a fucosyl donor to a hydroxyl group of a N-acetylglucosamine or galactose residue of the carbohydrate acceptor molecule.

This method embraces multiple glycosyltransferases catalyzing reactions in a single reaction mixture and preferred are those methods where one glycoslytransferase is a sialyltransferase selected from the group consisting of: α2,3 sialyltransferase, an α2,4 sialyltransferase an α2,6 sialyltransferase and α2,8 sialyltransferase. The invention contemplates the fucosylation of an oligosaccharide and preferred are those fucosyltransferases selected from the group consisting of: a α1,2 fucosyltransferase, α1,3/4 fucosyltransferase, α1,3 fucosyltransferase, α1,6 fucosyltransferase and α1,4 fucosyltransferase. Especially preferred fucosyltransferases include β-galactosidase α1,2 fucosyltransferase, N-acetylglucosamine α1,3 fucosyltransferase, N-acetylglucosamine α1,4 fucosyltransferase and N-acetyl-glucosamine α1,6 fucosyltransferase.

The carbohydrate acceptor molecules are virtually unlimited because the glycosyltransferases are not selective beyond the adjacent sugar positions. Thus they may be any carbohydrate substituted molecule wherein the carbohydrate is a Galβ1,4GlcNAc molecule or an analog thereof, or terminates in a Galβ1,4GlcNAc-X moiety and where X is an organic molecule. Additional carbohydrate acceptor molecules that are substrates for a fucoylase include analogs of Galβ1,4GlcNAc and Galβ1,4GlcNAc-X. Exemplary of such molecules as lactose, NeuAcα1,6Galβ1,4GlcNAc, Galβ1, 3GlcNAc, Galβ1,4Glucal (lactal), NeuAcα2,3Galβ1, 4Glucal, the 2-halo-substituted reaction products of the above glucals, Galβ1,4(5-thio)Glc, Galβ1,4GlcNAcβ-O-allyl and the like. It is to be understood that the carbohydrate acceptor molecule must contain an available hydroxyl group on the saccharide to which the donated fucosyl or other sugar group is linked, and the hydroxyl that must be present is determined by the glocsyltransferase enzyme that is utilized in the reaction.

The method contemplated herein further comprises regeneration of catalytic amounts of nucleotides used to form nucleoside sugars. A preferred bases for the nucleotides are either cytidine, guanine, or uridine. Monosaccharide donors are activated nucleotide sugars such as cytidine 5'-monophospho-N-acetylneuraminic acid, guanidine 5'-diphospho-fucose and uridine 5'-diphospho-galactose.

In addition to the above methods, this invention also contemplates in vitro reaction systems. Such systems refer to an inert or nonreactive container or compartment housing the reagents used to conduct the above described reactions. More specifically, these reaction systems have at a minimum a fucosyltransferase and a nucleoside diphosphofucose forming enzyme. These reaction systems can further comprise guanosine diphosphofucose pyrophosphorylase as the GDP-fucose-forming enzyme, a kinase such as pyruvate kinase or fructose-1,6-diphosphate kinase, acetyl kinase or fucose kinase. Other reagents can include a NADPH regeneration system or guanosine diphosphate mannose and guanosine diphospho mannose pyrophosphorylase. If a NADPH regeneration system is present it can include a catalytic amount of NADP, isopropanol in about 1 percent to about 10 percent, preferably about 2 percent to 4 percent w/v of the reaction system, and an alcohol dehydrogenase.

A number of chemical methods for synthesizing oligosaccharides are also disclosed herein. One method includes the production of a glycosyl 1- or 2-phosphate by reacting a blocked glycosyl ring having a hydroxyl at the anomeric position (1- or 2-position) with a trivalent phosphitylation reagent to yield a blocked glycosyl 1- or 2-phosphite-substituted ring. The blocked phosphite is oxidized to form a corresponding phosphate that is utilized in an enzymatic reaction. The glycosyl ring can include a galactosyl, glucosyl, fucosyl, N-acetylglucosyl and mannosyl as well as other saccharides. The preferred trivalent phosphitylating reagents are dibenzyl N,N-dialkylphosphoroamidite such as dibenzyl N,N-diethylphosphoroamidite. Such dialkyls are lower alkyls of 1–5 carbons inclusive and they can be the same or different. This method further utilizes blocking reagents such as acetyl or benzyl. The glycosyl ring is optionally from the group consisting of D- or L-aldoses having four, five or six carbons or from the group consisting of D- or L-ketoses having four, five or six carbons, as well as saccharides having up to nine carbons in the saccharide chain.

This invention further contemplates novel intermediates for the production of glycosyl 1- or 2-phosphates. A preferred intermediate is a blocked phosphityl monosaccharide of the formula I:

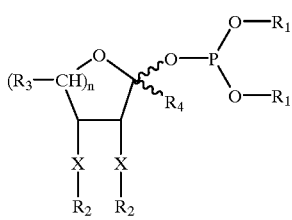

I wherein $R_1$ is aryl or lower alkyl;

X is independently oxygen or nitrogen;

$R_2$ in independently an acyl, benzyl, silyl or alkyl blocking group;

$R_3$ is independently —$CH_3$, —$OR_2$, —$CH_2OR_2$, —CH($OR_2$)—CH($OR_2$), or —CH($OR_2$)—CH($OR_2$)—CH($OR_2$);

$R_4$ is hydrogen (H), carboxyl or $C_1$–$C_5$ or benzyl carboxylate ester; and n is 1 or 2.

In a preferred group of compounds of formula I, $R_4$ is hydrogen so that formula I becomes formula II, below, wherein $R_1$, $R_2$, $R_3$, X and n are as before defined.

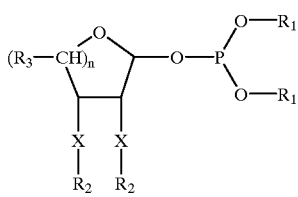

II

One group of especially preferred compounds are those wherein the monosaccharide is a six-membered ring, $R_4$ is H, and each X is oxygen such as mannose or fucose. Preferred are compounds wherein $R_1$ is benzyl and $R_2$ is benzyl or acetyl. Examples of preferred intermediates include dibenzylphosphityl 2,3,4,6-tetra-O-acetyl-D-mannoside or dibenzylphosphityl 2,3,4-tri-O-acetyl-L-fucoside.

Another group of especially preferred compounds are those wherein the monosaccharide is a six-membered ring, $R_1$ and $R_2$ are as above, one X is nitrogen with the others being oxygen. Exemplary compounds of that group include GlcNAc, GalNAc and NeuAc. Illustrative of these compounds are dibenzylphosphityl 2-acetamido-2-deoxy-3,4,6-tri-O-acetyl-D-glucoside and 2-acetamido-2-deoxy-3,4,6-tri-O-acetyl-D-galactoside.

A monosaccharide analog is also disclosed that is 2,3,4-tri-O-benzoyl-α-L-fucopyranosyl bromide.

Definitions

The phrase "available hydroxyl group" refers to a hydroxy-substituted carbon forming a part of the ring portion of a carbohydrate acceptor molecule that can form a glycosidic linkage through the action of a glycosyltransferase transferring a mono- or diphosphonucleoside-activated glycosyl donor to the available carbon. The "available hydroxyl group" is typically at the 3-position for fucosylation.

The phrase "blocked glycosyl ring" refers to glycosyl rings where the available amino or hydroxy substituents have been reacted with acyl, benzyl, silyl or alkyl blocking groups. Such groups have been generally described in Green, T. W., "Protective Groups in Organic Synthesis," John Wiley and Sons, Inc., 1981.

The term "carbohydrate(s)" is meant to include any organic moiety having carbohydrates covalently linked to any monomeric saccharides. This would include disaccharides, oligosaccharides, glycolipids, glycoproteins and unnatural linkages such as saccharides bound to organic compounds not naturally bound to sugars.

The phrase "carbohydrate acceptor molecule" refers to a molecule bearing at least one monosaccharide wherein that monosaccharide has one or more available hydroxyl groups for forming glycosidic linkages with mono- or diphosphonucleoside-activated glycosyl donors.

The phrase "catalytic amount" refers to concentrations of reagents that are present in relatively minor amounts compared to reagents which are in stoichiometric amounts and are not reduced in concentration by any significant amount during the reaction process. Those reagents that are present in catalytic amounts are typically activation reagents that are then regenerated recycled into the reaction by side reactions.

The phrase "mono or diphosphonucleoside-activated glycosyl donor" or "activated donor molecule" refers to a nucleotide sugar such as uridine 5'-diphospho-galactose. These compounds contain high energy bonds that facilitate the formation of the glycosyl bond to the carbohydrate acceptor molecule. The nucleoside can be comprised any of the natural bases and sugars and can also include minor derivatives such as methyl or azo substitutions on the base, dehydroxylated or blocked hydroxy groups on the sugars, and thiophosphate analogs of the diphosphate moiety.

The phrase "glycosidic linkage" refers to a oxygen/carbon linkage typically found between sugars. It can be either α or β in its configuration and typically involves a dehydration synthesis reaction where an diphosphonucleoside-activated glycosyl donor is transferred to an available carbon of a carbohydrate acceptor molecule using a glycosyltransferase.

The phrase "glycosyl ring" refers to a sugar or amino sugar having 5 or 6 carbons in the ring. Including aldoses, deoxyaldoses and ketoses without regard for orientation or configuration of the bonds of the asymmetric carbons. This includes such sugars as ribose, arabinose, xylose, lyxose, allose, altrose, glucose, idose, galactose, talose, ribulose, xylulose, psicose, N-acetylglucosamine, N-acetylgalactosamine, N-acetylmannosamine, N-acetylneuraminic acid, fructose, sorbose, tagatose, rhamnose and fucose.

The term "glycosyltransferase" refers to a family of enzymes that join a mono- or diphosphonucleoside-activated glycosyl donor to an available carbon of a carbohydrate acceptor molecule through a glycosidic linkage. These enzymes include both enzymes purified from natural sources and sources that have been genetically modified to express such enzymes. The glycosyltransferase family includes sialyltransferases, N-acetylglucosaminyltransferases, N-acetylgalactosaminyltransferases, fucosyltransferases, mannosyltransferases, galactogyltransferases, and KDO transferases.

The phrase "NADPH regeneration system" refers to a complement of enzymes that recycle NADP generated from an in situ enzyme reaction back to NADPH. Typically, such a system relies on an alcohol dehydrogenase converting an alcohol (isopropanol) to a ketone (acetone).

The phrase "sialylated Lewis ligand" in functional terms refers to molecule capable of binding to either the ELAM receptor or the GMP-140 receptor proteins. Chemically defined these ligands include the natural tetrasaccharide ligands $SLe^x$ and $SLe^a$ and derivatives thereof. Such derivatives include minor substitutions of the hydroxy groups for hydrogen, alkyl, acyloxy, alkoxy, halo, glycosyl, and the like, glycal molecules, a glycosyl ring compound in which the ring oxygen with S or NH and their alkyl, oxygenated or acyl derivatives, attachment of the anomeric carbon to carbohydrates or organic molecules, changes in the orientation and positions of glycosidic linkages or the substitution of enantiomers of the natural sugars.

The phrase "stoichiometric proportion" refers to amounts of starting product that are present in a direct proportion to the reaction products. A reagent is in stoichiometric proportion to the end products because it typically is used in the reactions producing the end product and is not regenerated during that process. Stoichiometric proportions typically approximate a 1:1 or 2:1 ratio of starting product to end product.

The phrase "trivalent phosphitylating reagent" refers to a reagent that reacts with a hydroxyl group of an organic compound to form a phosphite-containing product, which can be oxidized with an oxidizing reagent to produce a phosphate compound after deprotection.

Unless stated otherwise, all references are incorporated herein by reference.

Abbreviations

ADP, adenosine 5'-diphosphate;
ATP, adenosine 5'-triphosphate;
CMP, cytidine 5'-monophosphate;
CDP, cytidine 5'-diphosphate;
CTP, cytidine 5'-triphosphate;
CMP-NeuAc, cytidine 5'-monophospho-N-acetylneuraminic acid;
Fuc, fucose;
Fk, fucose kinase;
Fuc-1-P, fucose 1-phosphate;
Fuc-T, fucosyltransferase;
Gal, galactose;
GalNAc, N-acetylgalactosamine;
GTP, guanosine 5'-triphosphate;
GDP-Fuc, guanosine 5'-diphospho fucose;
GDP, guanosine 5'-diphosphate;
GDP-Man, guanosine 5'-diphospho-mannose;
GDP-ManPP, GDP-mannose pyrophosphorylase;
GDP-FUCPP, GDP-fucose pyrophosphorylase;
Glc-1-P, glucose-1-phosphate;
GlcNAc, N-acetylglucosamine;
ManNAc, N-acetylmannosamine;
NADP (NADPH), nicotinamide adenine dinucleotide phosphate;
NeuAc, N-acetylneuraminic acid;
NMK, nucleoside monophosphate kinase;
MK, myokinase;
PPase, inorganic pyrophosphatase;
PK, pyruvate kinase;
PEP, phospho(enol)pyruvate;
Pyr, pyruvate;
PPi, inorganic pyrophosphate;
Pi, inorganic phosphate;
Rha, rhamnose;
UDP, uridine 5'-diphosphate;
UTP, uridine 5'-triphosphate;
UDP-Glc, uridine 5'-diphospho-glucose,
UDP-Gal, uridine 5'-diphospho-galactose Many of the structural formulas utilized herein contain only two or three groups bonded to ring carbon atoms. Following convention, the unshown groups are hydrogen atoms and are usually not depicted bonded to carbon atoms unless stereochemistry is desired to be shown. In other formulas, darkened wedge-shaped lines are used to depict bonds coming up from the plane of the page, whereas dashed wedge-shaped lines are used to depict bonds that recede from the plane of the paper. Wavy lines are used to indicate that both types of bonding (both $\alpha$ and $\beta$-bonds) are contemplated.

DETAILED DESCRIPTION OF THE DRAWINGS

FIG. 1 provides a typical time course of the conversion of GDP-mannose to GDP-fucose by NADPH oxidation using optical density (Abs) measurements. Curve A: control cuvette without GDP-mannose. Curve B: same as control except 1 $\mu$mole of GDP-mannose was added. The ordinate is in absorbance units at 340 nm, whereas the abscissa is in minutes.

Figure 2A:
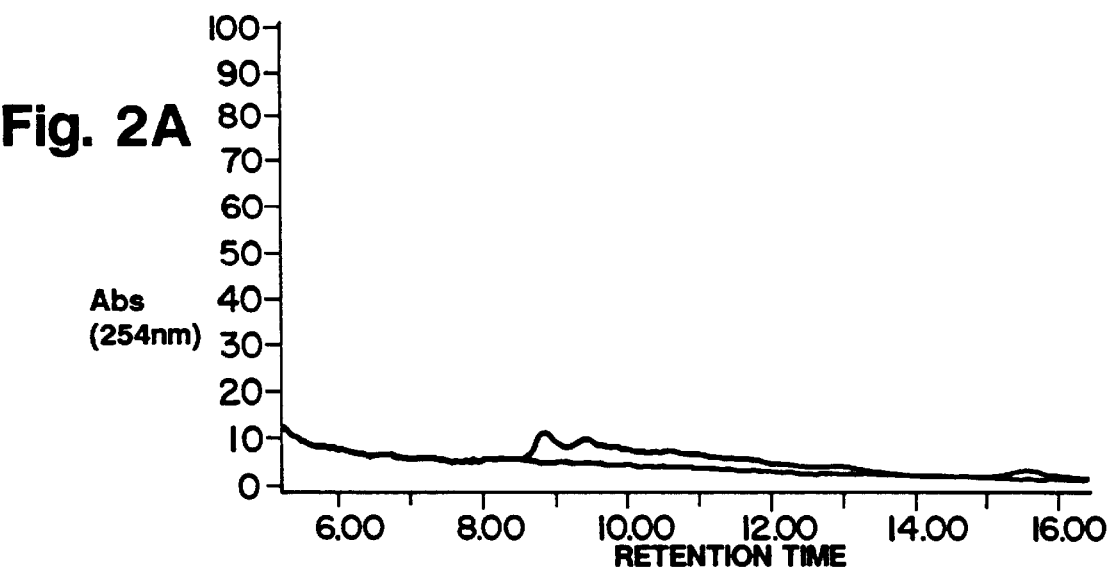
Figure 2B:
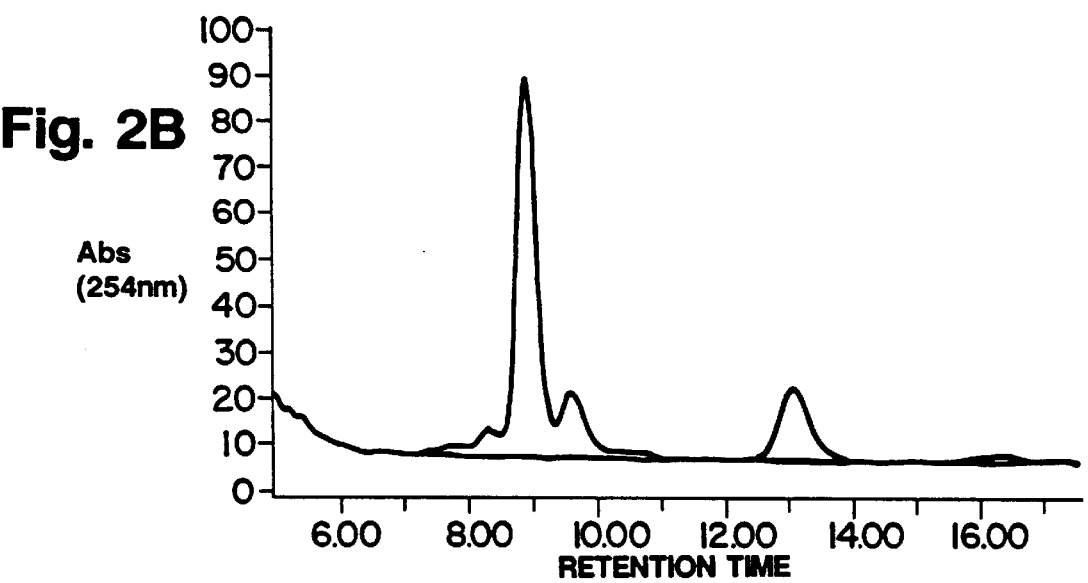
Figure 2C:
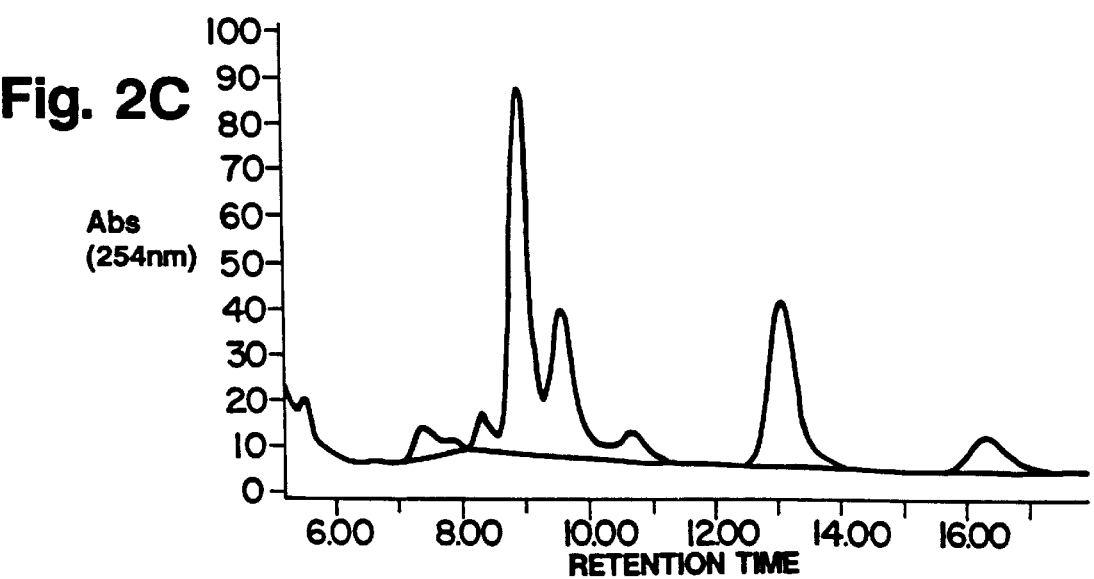

FIG. 2, in three panels as FIGS. 2-A, 2-B and 2-C, shows HPLC elution charts for the conversion of GDP-mannose (a) to GDP-fucose (b) at zero time (2-A), about three hours (2-B) and about six hours (2-C), respectively, after initiation of the reaction. The ordinate is in relative absorption units at 254 nm, whereas the abscissa is in minutes.

Figure 3:
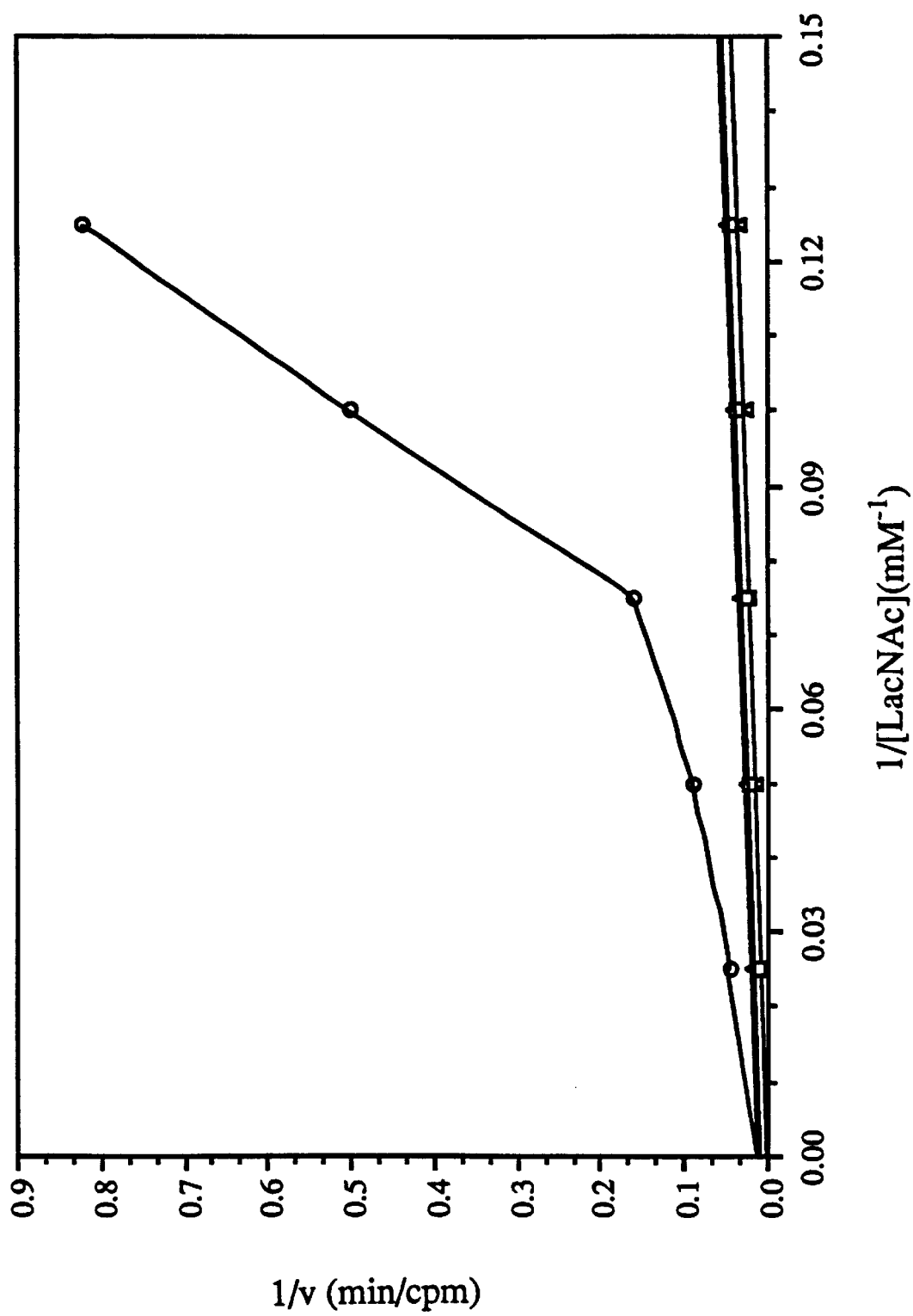

FIG. 3 is a graph that illustrates the synergistic inhibition of $\alpha$1,3 fucosyltransferase with guanosine 5'-diphosphate (GDP) and Compound 50 in the presence of 0.2 mM $^{14}$C-GDP-fucose, and 20 mM $MnCl_2$ at pH 6.2. Symbols are as follows: open triangles=no inhibitor; closed triangles= 0.05 mM GDP; open squares=34 mM Compound 50; and open circles=0.05 mM GDP plus 34 mM Compound 50. The ordinate is in units of the inverse of the initial velocity of product formation (1/v), whereas the abscissa is the inverse of the concentration of N-acetyllactosamine (LacNAc).

DETAILED DESCRIPTION OF THE INVENTION

This invention contemplates an in situ multi-enzyme reaction process in which a carbohydrate acceptor molecule is fucosylated with a nucleoside 5'-diphosphofucose using a fucosyltransferase wherein the nucleoside 5'-diphosphofucose is preferably enzymatically generated from catalytic amounts of nucleotides. See generally Schemes 1 and 2, below.

Scheme 1
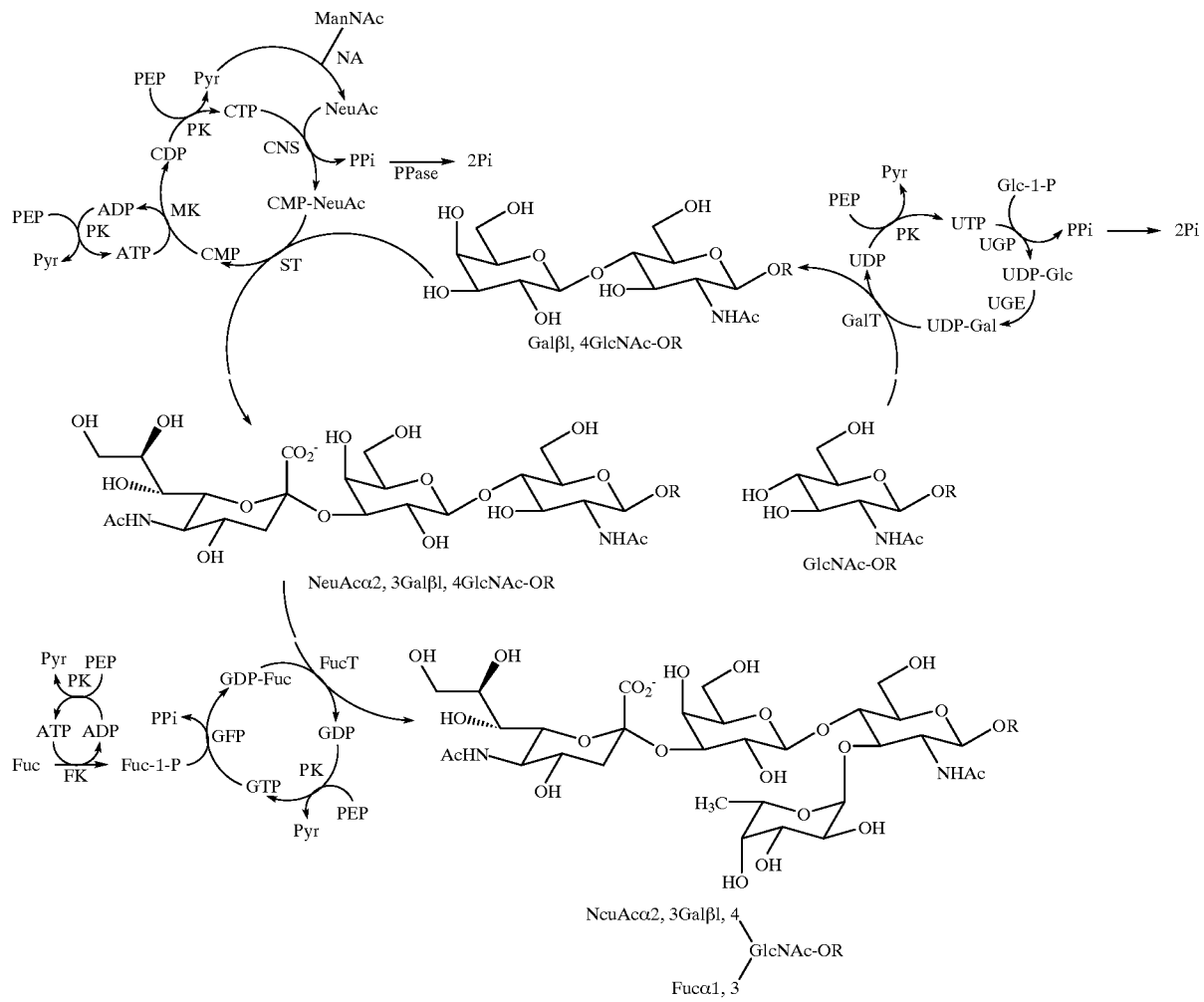
Scheme 2
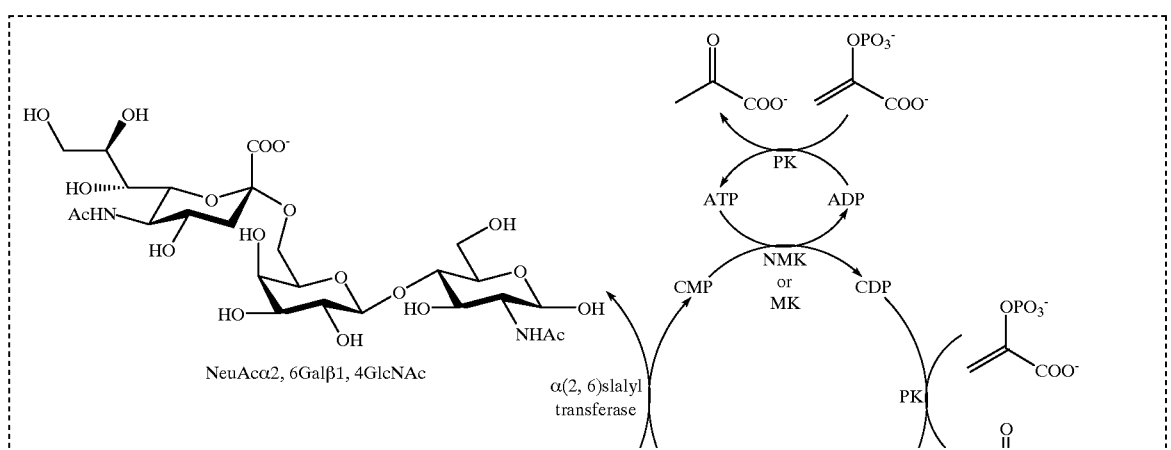

-continued

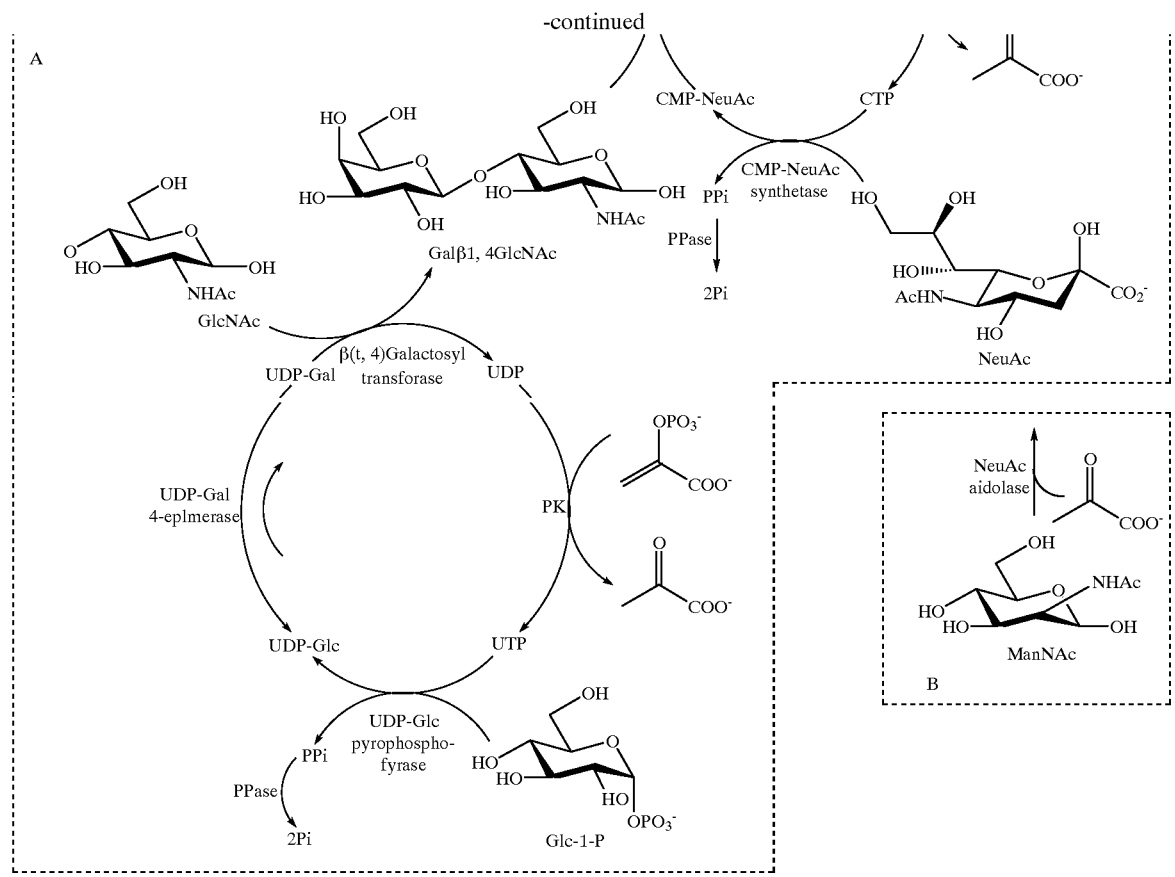

More specifically, the disclosed invention provides for improved means to obtain the precursor nucleotide sugars that function as donor substrates for the glycosyltransferase reactions. These methods include chemical and enzymatic means. The chemical improvement relates to improved yield and stability in the blocked sugars intermediate compounds used to form the glycosyl 1- or 2-phosphates which in turn are oxidized to phosphates, which are condensed with nucleoside monophosphates to yield nucleoside 5'-diphospho sugars or nucleotide sugars.

Another aspect of this invention is the development of a multi-enzyme system comprising more than one glycosyltransferase reaction for the synthesis of carbohydrates wherein one improvement resides in the use of catalytic amounts of nucleotide. Nucleotides are regenerated from the mono- or di-phosphate form to the tri-phosphate form using in situ enzymatic reaction simultaneous with the glycosyltransferase reactions. Catalytic amounts of nucleotide are useful because of the inhibitory effect nucleotides have on glycosyltransferases.

The following related U.S. patent applications contain subject matter related to the described inventions: U.S. Ser. No. 07/670,701 filed Mar. 18, 1991; U.S. Ser. No. 07/707, 600 filed May 30, 1991; U.S. Ser. No. 07/738,211 filed Jul. 30, 1991 entitled Oligosaccharide Enzyme Substrates and Inhibitors: Methods and Compositions; U.S. Ser. No. 07/852,409, filed Mar. 16, 1992 and U.S. Ser. No. 07/889, 652, filed May 26, 1992. Each of these five patent applications is hereby incorporated herein by reference.

A. Fucosylation

One aspect of this invention focuses on the use of the above described and referenced technology for the fucosylation of carbohydrates. Fucosylation is a common terminal modification for many biologically active carbohydrates such as the Lewis antigens both sialylated and nonsialylated.

(1) Fucosyltransferases.

Fucosylation arises from the action of a fucosyltransferase. Fucosyltransferases are well known and have been reviewed in Adv. Enzymol., 52:44–56 (1981). The carbon of the acceptor carbohydrate is typically a ring member of a glucose, galactose or N-acetylglucosamine, or an analogue thereof. The O glycosidic linkage is most commonly in the α orientation. The most common sites are the 2-, 3-, or 6-hydroxyl of galactose, the 3-, 4-, or 6-hydroxyl group of N-acetylglucosamine or the 3- or 4-hydroxyl of glucose. Glucal- and (5-thio)glucose-containing saccharides can also be the accepting saccharide unit of an acceptor carbohydrate for fucosyltransferase enzymes.

Fucosyltransferases can be isolated from natural sources or from recombinant microorganisms which have been genetically altered to express fucosyltransferases. Purified native fucosyltransferases have been described by Foster, J. Biol Chem. 266:3526–3531 (1991); Muramatsu, Eur. J. Biochem., 157:71–75 (1986); and Prieels et al., J. Biol Chem., 256:10456–10463 (1981). Fucosyltransferase genes have been reported as cloned and expressed by Campbell et al., J. Biol Chem., 259:11208–11214 (1984); Larsen, et al., Proc. Natl. Acad. Sci., U.S.A., 87:6674–6678 (1990); and Kukowska-Latallo, et al., Genes and Devel., 4:1288–1303 (1990); Weston et al., J. Biol. Chem., 267:4152 (1992).

In general, the fucosyltransferases are membrane bound. Thus, intact fucosyltransferases are typically insoluble in aqueous solution. To facilitate their use in the methods and reaction systems of this invention, it is preferable to use soluble enzymes wherein the insoluble cytoplasmic tail has been deleted or rendered more hydrophilic by selective deletion or addition of polar amino acids. However, native intact fucosyltransferases can be used in this invention through the addition of minor quantities of nonionic detergents such as Triton X-100.

Fucosyltransferases are a specific type of glycosyltransferase. The activated donor molecule is typically a nucleotide 5'-diphosphofucose. The reaction generates the nucleotide as a leaving group, and a fucose having a reactive carbonium ion that forms a glycosidic linkage with the available hydroxyl group of the acceptor molecule.

(2) Fucosylation reaction conditions and substrates.

The fucosyltransferases are typical glycosylases and are relatively hardy enzymes. Reaction conditions suitable for most glycosyltransferases are suitable for fucosyltransferases. For example, suitable reaction conditions include a temperature range of about 10° to 40° C., buffers include organic and inorganic buffers with their pI within the physiological pH range. An acceptable pH range is about 4 to about 9. Salt concentrations are about 0 to 200 mM, and about 0.1 to about 1.0 percent of a nonionic detergent (e.g., Triton-X 100) is used when the enzymes are otherwise not soluble in the aqueous fucosylation medium. Divalent cations such as $Mn^{2+}$ are often needed.

The carbohydrate acceptor molecules are virtually unlimited. The known sites linkage are provided above; however, the remainder of the carbohydrate acceptor molecule is not critical. The fucosyltransferases are quite substrate tolerant and beyond the acceptor sugar upon which the fucose is attached and sugars immediately adjacent to the acceptor sugar, the remaining structure of the substrate is of little significance. The acceptor carbohydrate molecules can be made up exclusively of sugar residues including monosaccharides, of glycoproteins, of glycolipids, or unnatural compounds where the sugar accepting the fucose is linked to compounds such as aryl, heterocycles, cycloalkanes and acyclic hydrocarbons.

A preferred carbohydrate acceptor molecule terminates in a Galβ1,4GlcNAc-X moiety in which X is an organic molecule. Exemplary X groups are noted hereinafter in the text. Exemplary carbohydrate acceptor molecules include Galβ1,4GlcNAc, lactose, NeuAcα2,6Galβ1,4GlcNAc, Galβ1,3GlcNAc, Galβ1,4Glucal (lactal), NeuAcα2,3Galβ1, 4Glucal, the 2-halo-substituted reaction products of the above glucals, Galβ1,4(5-thio)Glc, Galβ1,4GlcNAcβ-O-allyl.

A $SLe^x$ or $SLe^a$ analog can thus include a halogen atom in place of one of the ring hydroxyls. A new method has been found for preparing 2- or 3-halo-mono- and oligosaccharides from their corresponding glycals through the use of chloroperoxidase. The resulting 2(3)-deoxy-2(3)-halosaccharides can then be utilized in the syntheses discussed elsewhere herein.

In accordance with this method, a glycal is admixed with hydrogen peroxide, a halide ion of choice (chloride, bromide or iodide) and a catalytic amount of chloroperoxidase (EC 1.11.10) in an aqueous buffer having a pH value of about 2.5 to about 3.5 to form a reaction mixture. The resulting reaction mixture is then maintained until the desired product is formed. Concentrations of the various reagents can vary as is well known in the art. Exemplary concentrations and syntheses are provided hereinafter. The halohydron product so formed is then preferably recovered.

At ambient room temperature, typical reaction times are about 15 minutes to 2–4 days. Iodide reacts most rapidly and chloride reacts most slowly.

Thermodynamically formed products are typically obtained except where 1,3-diaxial interactions preclude formation of a 2-axially substituted product. When 1,3-diaxial interactions are present in the reacting glycal, stereospecificity in the halohydrated product is observed as to the α- or β-orientation of the halo group, with both anomers of the 1- or 2-hydroxyl group also being formed. Exemplary syntheses of 2- or 3-halo carbohydrate acceptor molecules and their precursors are illustrated in Schemes 3, 4 and 4a below.

Bromohydration of a sialyl $Le^x$ molecule having a terminal glycal (Compound 36 of Scheme 4a) that has a solution conformation similar to that of sialyl $Le^x$ provided products (Compounds 37a and 37b). Those products shared the same conformation as Compound 36 and sialyl $Le^x$ in the binding domain area consisting of NeuAc-Gal-Fuc according to NOE studies.

Brominated saccharides can also be prepared using N-bromosuccinimide (NBS) in an acetonitrile-water solvent. This procedure can be used to provide a changed ratio of products formed such as Compound 32 and 33 that are produced equally in the enzymatic reaction, and in a 1:2.5 (32:33) ratio using NBS. The 3-halo Compound 35 and its isomeric halohydration product Compound 35a are produced in a 2:3 (35:35a) ratio using the NBS reaction as compared to a single isomer, Compound 35, when the enzymatic reaction is used.

Scheme 3

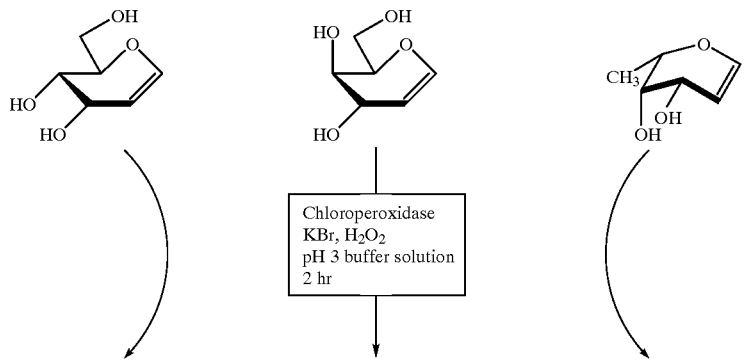

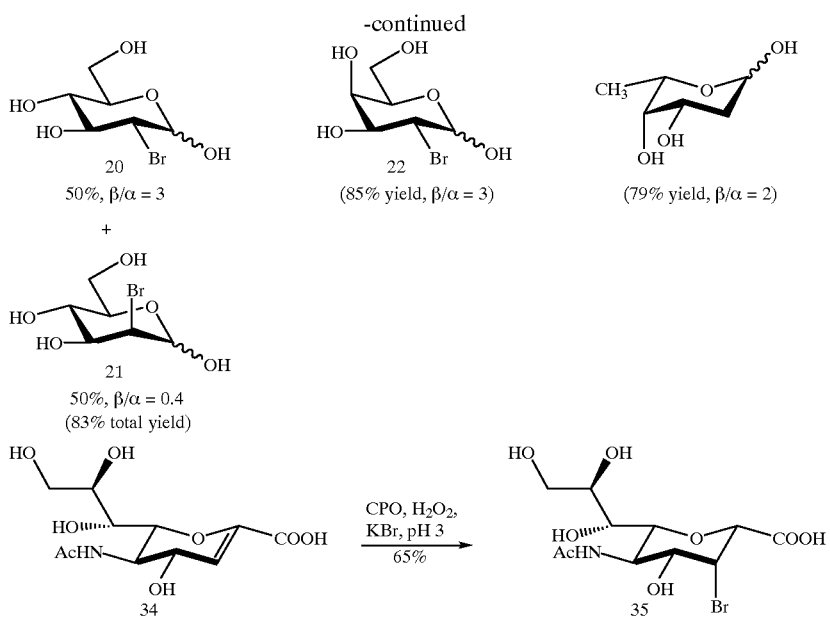

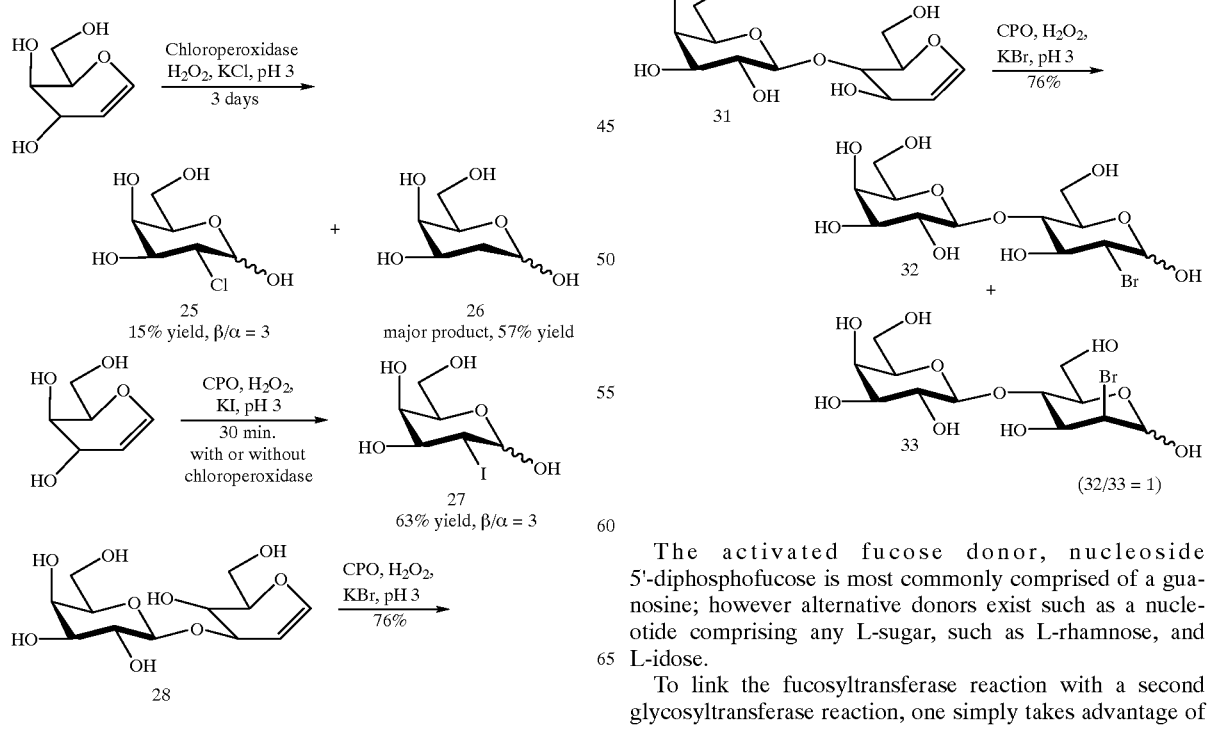

Scheme 3 illustrates the bromohydration of D-glucal, D-galactal and D-fucal and the formation of the corresponding 2-deoxy-2-bromomonosaccharides, Compounds 20, 21, 22 and 23. The bromohydration of sialal, Compound 34, with chloroperoxidase (CPO), to form the corresponding 3-deoxy-3-bromosialic acid, Compound 35, is also shown at the bottom of Scheme 3.

Scheme 4 illustrates the chloro- and iodohydration of galactal to form Compounds 25, 26 and 27. Also shown in Scheme 4 is the bromohydration of Gal1,3Glucal (Compound 28) and Gal1,4Glucal (Compound 31) to form the corresponding α- and β-2-deoxy-2-bromo compounds, Compounds 29 and 30, and Compounds 32 and 33, respectively.

The activated fucose donor, nucleoside 5'-diphosphofucose is most commonly comprised of a guanosine; however alternative donors exist such as a nucleotide comprising any L-sugar, such as L-rhamnose, and L-idose.

To link the fucosyltransferase reaction with a second glycosyltransferase reaction, one simply takes advantage of the fact that the optimum reaction conditions for most glycosyltransferases overlap. Thus, the given reaction conditions for any glycosyltransferase permit the functioning of the known fucosyltransferases. Using the reaction conditions set forth above for the fucosyltransferases and using routine titration experimentation, one can obtain reaction conditions suitable for the synthesis of a fucosylated oligosaccharide using only monosaccharides.

In general when selecting reaction conditions for multiple glycosyltransferase reactions in a single reaction mixture, one takes into consideration, temperature, pH, solvent osmolarity and ionic composition as set forth above. When one of the glycosyltransferases is a fucosyltransferase, acceptable reaction conditions include a pH range preferably between about 6.0 to about 8.5 and most preferably between about 7.0 and about 7.5. Divalent cations such as $Mn^{2+}$ are useful and divalent ion chelators are not desired.

The buffers are not critical. Aqueous buffers such as HEPES are adequate. The osmolarity of the buffer inclusive of the buffer is between 100 mOsm to about 300 mOsm.

The above conditions at which the enzymes function are referred to herein as biological reaction conditions.

The reaction times vary with the substrates, enzymes, and temperatures. Typically, the reaction times are be from 24 to 96 hours.

Under certain circumstances, when using a galactosyltransferase and the monosaccharide acceptor has an aglycon of one position of glucose in an α-orientation, the reaction conditions may include lactalbumin, preferably α-lactalbumin.

For example, the sialyltransferase reaction described in Ichikawa et al., *J. Amer. Chem. Soc.*, 113:4698–4700 (1991) can be linked with a recombinant human Lewis α(1,3/4) fucosyltransferase as described by Kukowska-Latallo et al., *Genes and Devel.*, 4:1288 (1990). One simply follows the basic reaction mixture of aqueous buffer (HEPES) having a pH range of 7.0–7.5, a salt concentration 50–200 mM is appropriate. The reaction is run at about 37° C.

B. Substrate Specificity and Inhibition Study of Glycosyltransferases

α1,3/4FucT. The fucosyltransferase that is capable of transferring the Fuc moiety from GDP-Fuc to the 3- and the 4-OH groups of GlcNAc to produce $Le^x$ or $Le^a$ is α1,3/4FucT. [Fukowska-Latallo et al., *Gene & Development*, 4:1288 (1990); Dumas et al., *Bioorg. & Med. Chem. Lett.*, 1:425 (1990)]. As indicated in Table 1, below, the enzyme catalyzes the fucosylation of Galβ1,3GlcNAc faster ($V_{rel}$ 580) than Galβ1,4GlcNAc (LacNAc) ($V_{rel}$ 100) (Entries 1 and 4) at 10 mM concentration of the carbohydrate acceptor. Sialylated LacNAc (Entry 7) is also a substrate for this enzyme, allowing the synthesis [Dumas et al., *Bioorg. & Med. Chem. Lett.*, 1:425 (1991)] of sialyl $Le^x$. Interestingly, Galβ1,4(5-thio)Glc [Gautheron-Le Narvor et al., *J. Chem. Soc. Chem. Commun.*, 1130 (1991); Wong et al., *J. Am. Chem. Soc.*, 113:8137–8245 (1991)] is a better substrate than the corresponding disaccharide, lactose (Entries 2 and 3) under these conditions. Each of the substrates of Table 1 constitutes a carbohydrate acceptor for fucose from the fucosyl donor using this enzyme. Galβ1,4deoxynojirimycin [Gautheron-Le Narvor et al., *J. Chem. Soc. Chem. Commun.*, 1130 (1991); Wong et al., *J. Am. Chem. Soc.*, 113:8137–8245 (1991)] (Entry 11), however, is an inhibitor ($IC_{50}$ 40 mM). Due to the limited supply of α1,3/4Fuc, no further investigation was carried out.

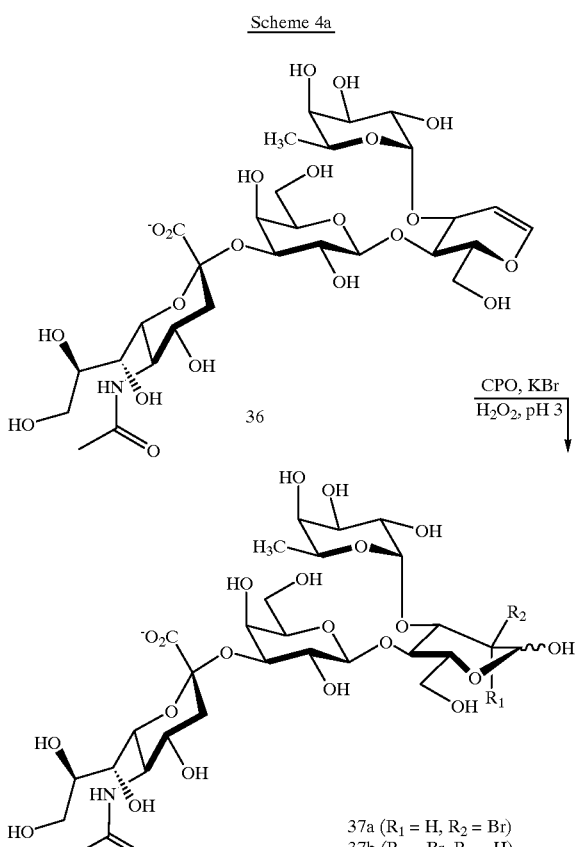

Scheme 4a

TABLE 1

Disaccharide and trisaccharides as substrates or inhibitors for α1,3/4Fucosyltransferase.

| Entry | Substrates | $V_{rel}^a$ |
|---|---|---|
| 1. | Galβ1,4GlcNAc | 100 |
| 2. | Galβ1,4Glc | 120 |
| 3. | Galβ1,4(5-thioGlc)$^c$ | 310 |
| 4. | Galβ1,3GlcNAc | 580 |
| 5. | GlcNAcβ1,4GlcNAc | 23 |
| 6. | Galβ1,4GalNAc | 27 |
| 7. | NeuAcα2,3Galβ1,4GlcNAc$^d$ | 60 |
| 8. | Fucα1,2Galβ1,4Glc$^e$ | 250 |
| 9. | GlcNAcβ1,6Galβ1,4Glc$^e$ | 13 |
| | Inhibitors | $IC_{50}$ (mM) |
| 10. | Galβ1,4(3-deoxy)GlcNAcβOallyl$^c$ | >125 |
| 11. | Galβ1,4deoxynojirimycin$^c$ | 40 |
| 12. | Galβ1,4Glucal$^{c,f}$ | >125 |

$^a$Relative velocities with 0.20 mM GDP-Fuc, 20 mM $MnCl_2$, and 10 mM acceptor. Specific activity = 2U/mg (1U = 1 μmol of GDP-Fuc consumed per hour). $^b$Inhibitor concentration required to give 50% inhibition with 0.2 mM GDP-Fuc. $^c$Gautheron-Le Narvor, C. et al., J. Chem. Soc. Chem. Commun. 1991, 1130; Wong, C.-H. et al., J. Am. Chem. Soc. 1991, 113, 8137. $^d$Purchased from Oxford GlycoSystems, Inc., Rosedale, New York. $^e$Purchased from Sigma, St. Louis, MO. $^f$Haworth, W.N. et al, J. Chem. Soc. 1930, 2644.

α1,3FucT. The enzyme responsible for sialyl $Le^x$ production is human plasma type α1,3FucT, which has been recently cloned, overexpressed, [Weston et al., *J. Biol. Chem.*, 267:4152 (1992)] and utilized in synthesis. The substrate specificity indicated (Table 2, below), as expected, that the enzyme is more specific for LacNAc (V/$K_m$ 2.9, Entry 1) than Galβ1,3GlcNAc (V/$K_m$ 0.22, Entry 5). Similar to the result for α1,3/4FucT (Entry 3 in Table 1), Galβ1,4 (5-thio)Glc is also a substrate for αFucT (Entry 3 in Table 2). Unlike the α1,3/4 enzyme, lactal (Entry 6) is a substrate for the α1,3 enzyme.

The trisaccharide NeuAcα2,3Galβ1,4GlcNAc (Entry 7), a precursor to sialyl Le$^x$, is the best substrate with a relative maximum velocity of 620 percent based on LacNAc. The α2,6-linked sialoside (Entry 10) is about 50 times less active as a substrate than the α2,3-isomer. It is worth noting that the enzyme can also transfer Fuc to the glucal-containing sialylated trisaccharide ($V_{rel}$ 330 percent, Entry 9).

With regard to binding, the enzyme has higher affinity for disaccharides (Entries 1,3,4,6) than trisaccharides. An increase of affinity was observed when the GlcNAc moiety of LacNAc was replaced with 5-thio-Glc, glucal [Haworth et al., *J. Chem. Soc.*, 2644 (1990)] or GlcNAcβOallyl. Lactose has, however, a very low affinity although the relative rate at $V_{max}$ is quite high (150 percent). Each of the substrates of Table 2 is a carbohydrate acceptor for fucose from the fucosyl donor using this enzyme.

TABLE 2

Disaccharide and trisaccharides as substrates for α1,3Fucosyltransferase.

| Entry | Substrates | $K_m$ (mM) | $V_{rel}$$^a$ |
|---|---|---|---|
| 1. | Galβ1,4GlcNAc | 35 | 100 |
| 2. | Galβ1,4Glc | 500 | 150 |
| 3. | Galβ1,4(5-thioGlc)$^b$ | 12 | 51 |
| 4. | Galβ1,4GlcNAcβOallyl$^c$ | 16 | 64 |
| 5. | Galβ1,3GlcNAc | 600 | 130 |
| 6. | Galβ1,4Glucal$^{b,d}$ | 34 | 10 |
| 7. | NeuAcα2,3Galβ1,4GlcNAc$^e$ | 100 | 620 |
| 8. | NeuAcα2,3Galβ1,4GlcNAcβOallyl$^f$ | 280 | 380 |
| 9. | NeuAcα2,3Galβ1,4Glucal$^f$ | 64 | 330 |
| 10. | NeuAcα2,6Galβ1,4GlcNAc$^g$ | 70 | 13 |

$^a$Relative maximal velocities with 0.1 mM GDP-Fuc, 10 mM MnCl$_2$ and 10 mM Galβ1,4GlcNAc. Specific activity = 2.6 U/mg (1U = 1μmol of GDP-Fuc consumed per h). $^b$Gautheron-Le Narvor, C. et al., J. Chem. Soc. Chem. Commun. 1991, 1130.; Wong, C.-H. et al., J. Am. Chem. Soc. 1991, 113, 8137. $^d$Haworth, W. N, et al., J. Chem. Soc. 1930, 2644. $^e$Purchased from Oxford GlycoSystems, Inc., Rosedale, New York. $^f$Prepared enzymatically using an α2,3sialyltransferase from Cytel Co. in this study. $^g$Ichikawa, Y. et al., J. Am. Chem. Soc. 1991, 113, 4698.

In our study of the inhibition of α1,3FucT (Table 3, below), the observation that 3'-deoxy-LacNAc-βOallyl [Gautheron-Le Narvor et al.,*J. Chem. Soc. Chem. Commun.*, 1130 (1991); Wong et al., *J. Am. Chem. Soc.*, 113:8137–8245 (1991)] is a weak inhibitor (Entry 5), is consistent with the previous report on deoxygenated oligosaccharides for glycosyltransferases. [Hindsgaul et al., *J. Biol. Chem.*, 266:17858 (1991)]. Among the acceptor carbohydrate substrate analogs examined, Galβ1, 4deoxynojirimycin is the most potent inhibitor (Entry 4, $IC_{50}$=8 mM).

Two aza sugars [Kajimoto et al., *J. Am. Chem. Soc.*, 113:6679 (1991)] known to be potent α-fucosidase inhibitors were assayed as the acceptor analogs (Entries 8 and 9), and they were found to be moderate inhibitors versus LacNAc for FucT ($IC_{50}$ about 34 to about 52 mM). Deoxynojirimycin was, however, a substrate for α1,4GalT. [Wong et al.,*J. Am. Chem. Soc.*, 113:8137–8145 (1991)]. GDP-Man is also a potent inhibitor of α1,3FucT ($IC_{50}$ 2 mM).

For the product inhibition study, our attention was focused on the released nucleoside diphosphate. GDP is a byproduct of enzymatic fucosylation and is a very potent noncompetitive inhibitor versus LacNAc ($K_{ii}$=0.13 mM, $K_{is}$=0.16 mM, Entry 10). Another nucleoside diphosphate, UDP released from the enzymatic galactosylation is also a very potent inhibitor of GalT ($K_i$=0.46 mM). GDP-Fuc is a potent inhibitor of α1,3FucT at concentration above 0.2 mM in the presence of 10 mM LacNAc. It is, however, not an inhibitor of α1,3/4FucT.

In addition to aza sugar Entries 8 and 9 in Table 3, other aza sugars such as Compounds 51, 52 and 53, below, also inhibit α-fucosidase activity as does Compound 50 (Entry 9 of Table 3). Compounds 50–53 exhibited $K_i$ values with that enzyme of 4, 22, 8 and 1.4 μM, respectively. [See also, Dumas et al., *Bioorg. & Med. Chem. Lett.*, 2:33 (1992).]

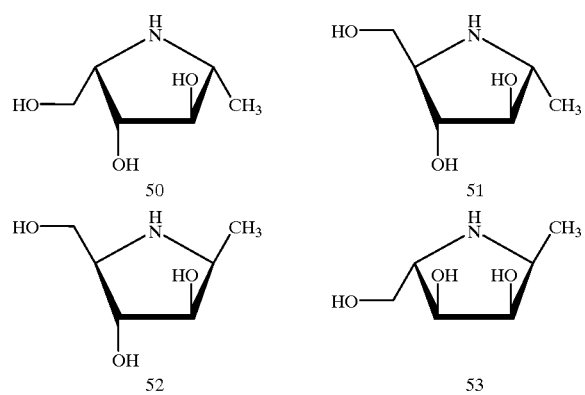

In addition to Compound 50, it has now been found that Compound 53 is also a competitive inhibitor of human plasma type α-1,3-fucosyltransferase. The $IC_{50}$ value versus LacNAc was 80 mM. In addition, GDP, which is formed during the fucosylation reaction from GDP-Fuc and is a noncompetitive inhibitor, when present at its $IC_{50}$ of 0.05 mM, exhibits a profound, synergistic inhibition in the presence of either of Compounds 50 or 53. Data from an exemplary inhibition study using Compound 50 are shown in FIG. 3. This synergistic effect may be due to an interaction between GDP and the aza sugar in the active site of the enzyme to form a complex that mimics the transition state structure of the fucosyltransfer reaction.

The above results provide a process for inhibiting a glycosyltransferase reaction such as a fucosyltransferase reaction. In accordance with that process, a glycosyltransferase such as human plasma type α1,3-fucosyltransferase, a carbohydrate acceptor molecule such as LacNAc, an activated glycosyl donor molecule such as GDP-Fuc and an inhibiting amount of an aza sugar such as either of Compounds 50 or 53 are admixed in an aqueous medium and are maintained under biological reaction conditions for a time period sufficient for the glycosyltransferase reaction to be inhibited.

More preferably, an inhibitory amount of the nucleoside diphosphate product of the glycosylation reaction such as UDP or GDP where GDP-Fuc is the glycosylation donor is also present. The inhibitory amounts of the aza sugar and nucleoside diphosphate, when present, are preferably within at least 10 percent of their individual $IC_{50}$ values, and more preferably those amounts are at least 50 percent of their individual $IC_{50}$ values measured in vitro as discussed hereinafter for the particular glycosylation reaction to be inhibited. Concentrations in excess of the $IC_{50}$ values can also be used. That glycosylation reaction is typically inhibited by at least 25 percent, and more preferably by at least 50 percent.

The glycosylation inhibition can take place in vitro or in vivo. An exemplary in vitro inhibition study is illustrated hereinafter. For in vivo use, the enzyme, the glycosyl donor and acceptor molecules and GDP are present in the host mammal, which can be a laboratory mammal such as a mouse, rat or rabbit, or a human. The aza sugar is administered to the host by a usually used technique for administering drugs as are well known in the art. Added amounts of GDP can also be administered, if desired. The biological reaction conditions are provided by the body of the host mammal. The added aza sugar is maintained within the host mammal until it is excreted or catabolized.

TABLE 3

Inhibition of α1,3FucT

| Entry | Inhibitors | $IC_{50}$[a] (mM) |
|---|---|---|
| 1. | Galβ1,4Glucal[b] | NI[c] |
| 2. | Galβ1,3GlcNAc | NI |
| 3. | Galβ1,3GalNAc | >100 |
| 4. | Galβ1,4Deoxynojirimycin[b] | 8 |
| 5. | Galβ1,4(3-deoxy)GlcNAcβOallyl[b] | 710 |
| 6. | GlcNAcβ1,4GlcNAc | NI |
| 7. | GDP-Man | 2 |
| 8. | (structure)[d] | 52 |
| 9. | (structure)[d] | 34 |
| 10. | GDP | 0.05[e] |

[a]Inhibitor concentration required to give 50% inhibition with 0.1 mM GDP-Fuc, 10 mM $Mn^{2+}$ and 10 mM LacNAc at pH 6.2 and 37° C.
[b]Gautheron-Le Narvor, C. et al., J. Chem. Soc., Chem. Commun. 1991, 1130.
[c]No inhibition observed up to 50 mM of inhibitor concentration.
[d]Kajimoto, T. et al., J. Am. Chem. Soc. 1991, 113, 6679.
[e]$K_i$ = 19 ± 3 mM.
[e]$K_{ii}$ = 0.13 ± 0.05 mM, $K_{is}$ = 0.16 ± 0.06 mM.

C. Chemical and Enzymatic Means for Producing GDP-Fucose

The fucosyltransferase cycle reaction can be driven by either the addition of stoichiometric amounts of the appropriate sugar nucleotide such as GDP-fucose or preferably, the sugar nucleotide can be generated by catalytic amounts of the corresponding nucleotide and stoichiometric amounts of PEP and Man-1-P or Fuc-1-P.

GDP-fucose is the preferred activated sugar donor for the known fucosyltransferases. It is difficult and expensive to manufacture, and for the other reaction cycles described herein, it is preferred that its synthesis involve the in situ regeneration of its nucleotide precursors. A general scheme is presented in the fucose cycle of Scheme 1.

(1) Chemical synthesis of fucose 1-phosphate and GDP-fucose

The chemical synthesis of GDP-Fuc relies on the coupling of fucose 1-phosphate and an activated GMP such as GMP-morpholidate. See, generally, (a) Kochetkov et al., Adv. Carbohydr. Chem. Biochem., 28:307 (1973); (b) Moffat, Methods Enzymol., 8:136 (1966); and (c) Roseman et al., Am. Chem. Soc., 83:659 (1961). Due to the relatively high lability of fucose 1-phosphate and GDP-Fuc, the reported chemical yields for the synthesis of Fuc-1-P and the coupling reaction of Fuc-1-P and GMP derivative have been low. Several fucose 1-phosphate syntheses have been reported. Since only Fuc-1-P among the sugar nucleotides has a thermodynamically unstable β-phosphate moiety on the anomeric center of fucose, it is difficult to control the stereochemistry of the anomeric center. Herein are provided two efficient routes to GDP-Fuc: one by chemical and another by enzymatic method.

The first chemical synthesis of GDP-Fuc was performed by Barker's group. [Nunez et al., Can. J. Chem., 59:2086 (1981).] For the preparation of fucose 1-phosphate, they used 2,3,4-tri-O-acetyl-β-L-fucose, prepared from the corresponding bromo derivative followed by fractional crystallization, and phosphorylation of the resulting β-anomer. The Hindsgaul group [Gokhale, Can. J. Chem., 68:1063 (1990)] used a glycosylation reaction of acetofucosyl bromide and dibenzylphosphate tetrabutylammonium salt to produce a relatively unstable glycosyl phosphate (<10 min. in silica gel chromatography). Schmidt et al. [Schmidt et al., Liebigs Ann. Chem., 191:121 (1991)] used a fucosyl imidate and obtained the glycosidation product, without Lewis acid catalyst, in high yield. The van Boom group [Westerduinn et al., Tetrahedron Lett., 27:1211 (1986)] used a trivalent phosphitylating agent on 2,3,4-tri-O-benzyl-fucose and converted to an α-fucosyl phosphate.

Described herein are two improved approaches for chemical synthesis of GDP-fucose (see Schemes 5–7, below). One, Scheme 5, uses a glycosylation reaction of benzoylated (Bz) fucosyl bromide (Compound 3) and dibenzylphosphate. Employing a benzoyl group instead of acetyl as the protective group yields improved stability for the fucosyl derivative and stereoselectivity of the glycosylation reaction. The glycosylation of Compound 3 and dibenzylphosphate (Linshorst et al., Carbohydr. Res., 209:119 (1991)] proceeded very smoothly and gave the coupling product in 95 percent yield as a sole product. As expected, Compound 4 was stable enough to be purified on silica gel column (>3 hours); however, the purified material was unstable. When the purified Compound 4 was left overnight at room temperature, some decomposition and anomerization of Compound 4 were observed. It should be noted that the purified Compound 4 was used for the next step immediately. Deprotections of the benzyl (Bn) groups from the phosphate moiety and the benzoyl groups were performed stepwise as described previously. [Gokhale et al., Can. J. Chem., 68:1063 (1990).]

Scheme 5

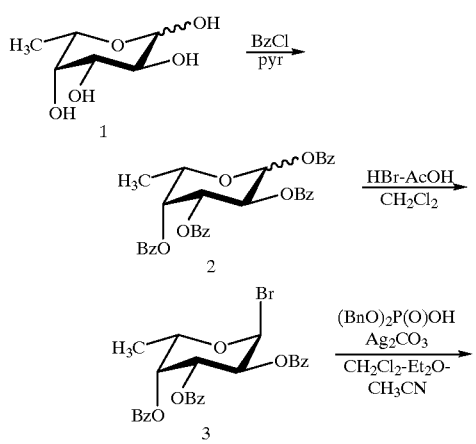

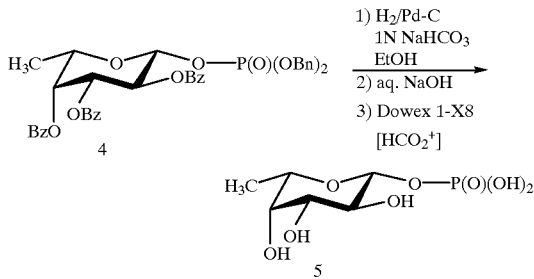

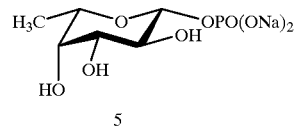

The phosphitylation reaction using (BnO₂)PNEt₂ (DDP) illustrated in Scheme 6 is quite useful for forming a variety of phosphites and corresponding phosphates in high yields. Further exemplary compounds and details are discussed hereinafter in Section H.

Fuc-1-P is efficiently activated by conversion to the trialkylammonium salt by reaction with guanosine-5'-monophospho morpholidate (1:2) in a solvent such as pyridine. The product, GDP-Fuc, Compound 12, is purified using conventional column chromatography. These reactions are shown in Scheme 7, below.

The other approach uses a trivalent phosphitylating reagent such as dibenzyl N,N-diethylphosphoroamidite (DDP) which has been used for the preparation of dihydroxyacetylphosphate (DHAP) (See Scheme 6, below.) [Pederson et al., *Tetrahedron*, 47:2643 (1991).] Thus, 2,3, 4-tri-O-acetyl fucose, Compound 7, prepared by either chemical and enzymatic deacetylation [Hennen et al., *J. Org. Chem.*, 53:4943 (1988)], was phosphinated with DDP in the presence of tetrazole. The reaction proceeded smoothly to give 79 percent yield of Compound 8, a compound of formulas I and II, which was oxidized to the corresponding phosphate Compound 9. Deprotection of Compound 9 was performed similarly to the preparation of Compound 5 from Compound 4.

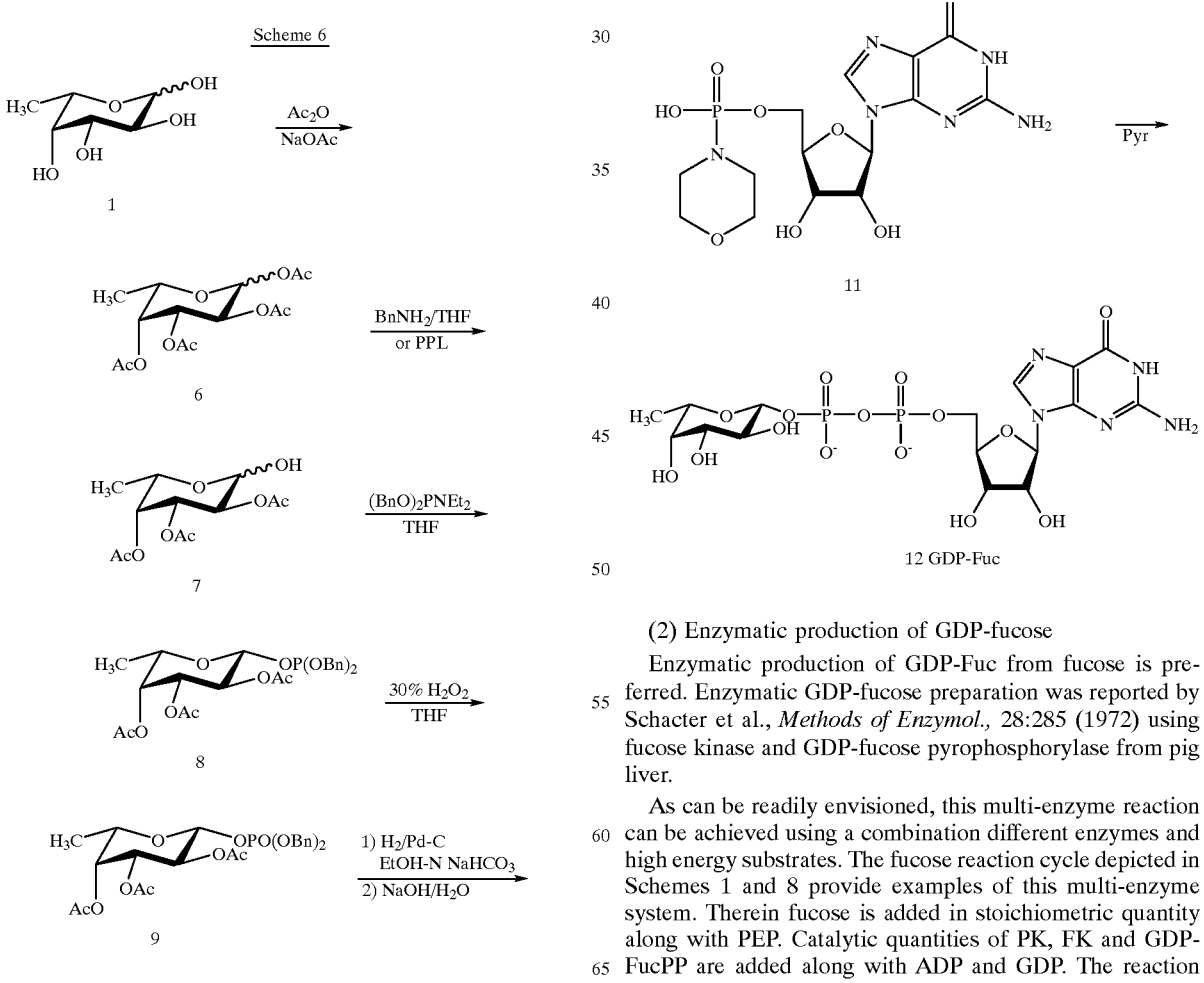

(2) Enzymatic production of GDP-fucose

Enzymatic production of GDP-Fuc from fucose is preferred. Enzymatic GDP-fucose preparation was reported by Schacter et al., *Methods of Enzymol.*, 28:285 (1972) using fucose kinase and GDP-fucose pyrophosphorylase from pig liver.

As can be readily envisioned, this multi-enzyme reaction can be achieved using a combination different enzymes and high energy substrates. The fucose reaction cycle depicted in Schemes 1 and 8 provide examples of this multi-enzyme system. Therein fucose is added in stoichiometric quantity along with PEP. Catalytic quantities of PK, FK and GDP-FucPP are added along with ADP and GDP. The reaction conditions are similar to those provided above for the transferases.

Scheme 8

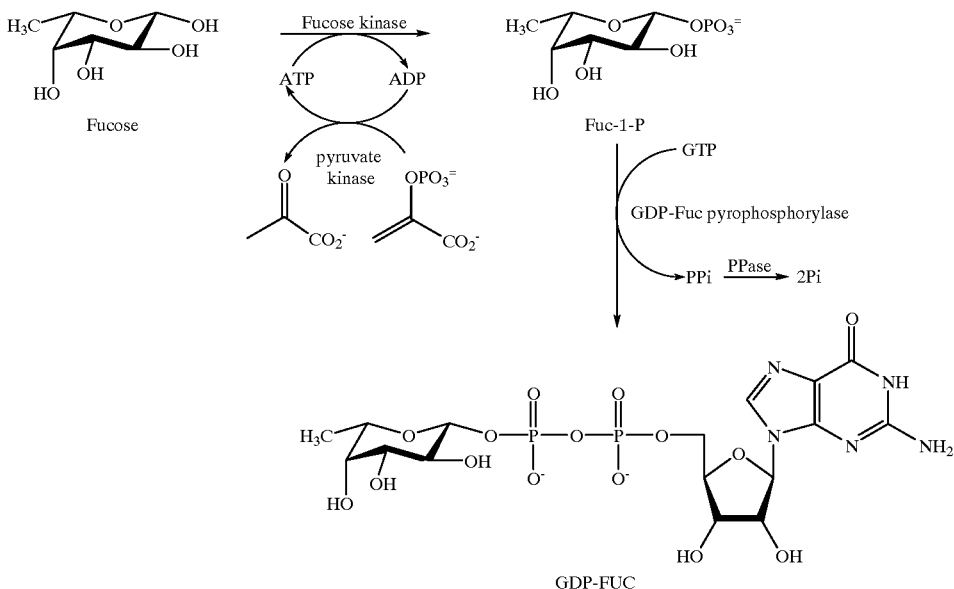

(3) Mannose as a starting material

Alternatively, GDP-Fuc can be obtained efficiently from the preparation of GDP-mannose and subsequent enzymatic conversion to GDP-Fuc. The precursor to GDP-Man is Man-1-P, Compound 18. Man-1-P is made using the same approach as described for the production of fucose-1-P. Preferred is the use of acetyl blocking groups to form mannose per O-acetate as shown in Scheme 9, below. Alternatively, Man-1-P can be enzymatically produced in a manner analogous to Glc-1-P.

Scheme 9

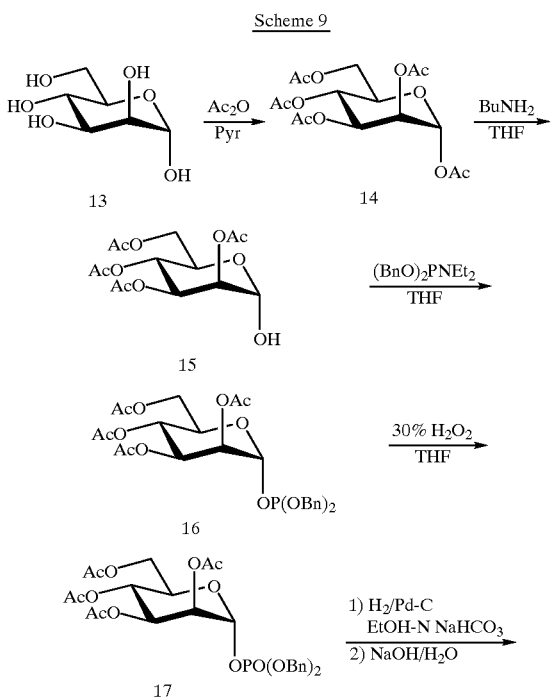

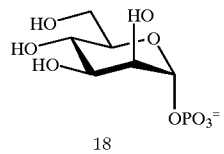

18

The enzymatic synthesis of GDP-fucose from mannose 1-phosphate with in situ generation of GDP-mannose is achieved by combining two enzyme systems: GDP-mannose pyrophosphorylase and GDP-fucose synthetic enzymes. NADPH regeneration is required for the formation of GDP-fucose. Such regeneration can be achieved with the use of NADPH dependent alcohol dehydrogenase from *Thermoanaerobacterium brokii* in the presence of isopropanol or glucose phosphate dehydrogenase in the presence of glucose. GDP-mannose pyrophosphorylase can be obtained from yeast as described below; but other sources such as Arthrobacter [Preiss et al., *J. Biol. Chem.*, 239:3119 (1964)], *Escherichia coli* [Lieberman et al., *J. Bact.*, 101:965 (1970)], as well as from mammalian source [Smoot et al., *Eur. J. Blochem.*, 148:83 (1985)] have been described.

The conversion of GDP-fucose from GDP-mannose was first reported by Ginsburg and Kirkman [Ginsburg et al., *J. Am. Chem. Soc.*, 80:3481 (1958). The enzyme was partially purified and used to demonstrate the conversion of GDP-mannose to GDP-fucose from *A. aerogenes* (ATCC 12658), currently was renamed as *Klebsiella pneumoniae* [Ginsburg, *J. Biol. Chem.*, 235:2196 (1960)]. The reaction was NADPH dependent. Yamamoto et al. also reported the synthesis of GDP-fucose from GDP-mannose by using the enzyme obtained from *Agrobacterium radiobacter* [Yamamoto et al., *Agric. Biol. Chem.*, 48:823 (1984)].

Herein is described the conversion of mannose-1-phosphate to GDP-fucose with in situ generation of GDP-mannose. Mannose-1-phosphate is converted to GDP-fucose by combining two enzyme systems, GDP-mannose pyrophosphorylase and GDP-fucose synthetic enzyme with regeneration of NADPH. Although the initial result gives low yield, however, it is expected that if higher enzyme activities are obtained, the yield can be improved significantly. These reactions are outlined in Schemes 10 and 11.

Scheme 10
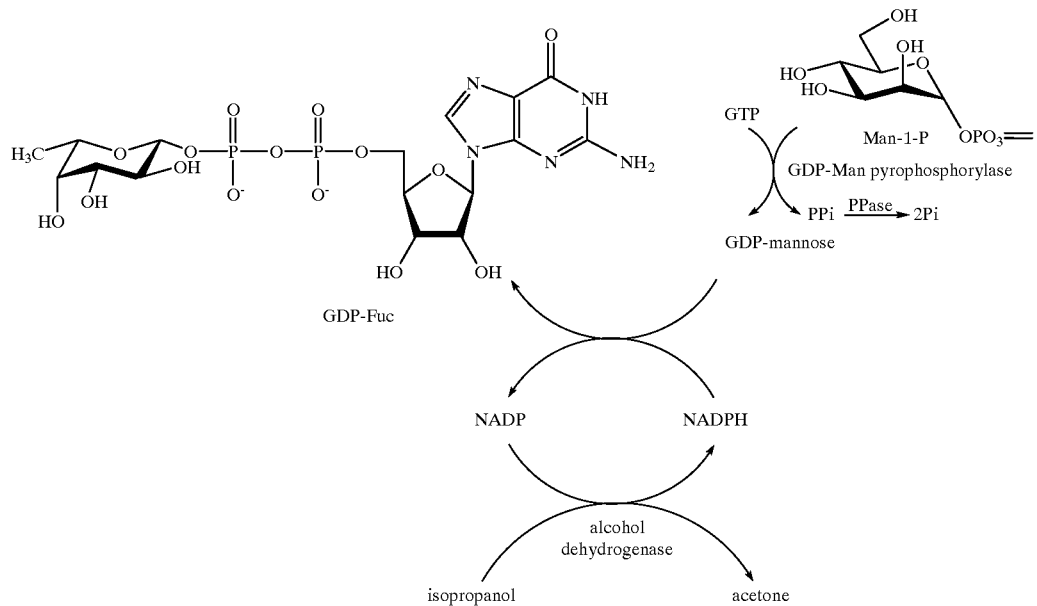
Scheme 11
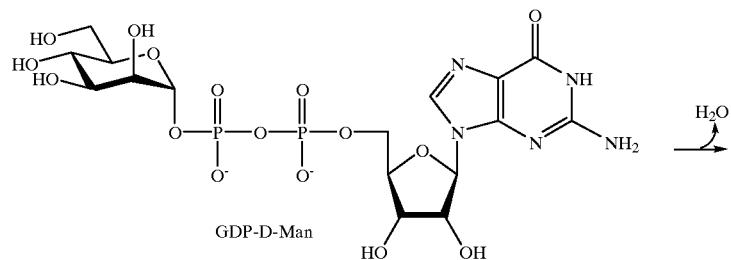
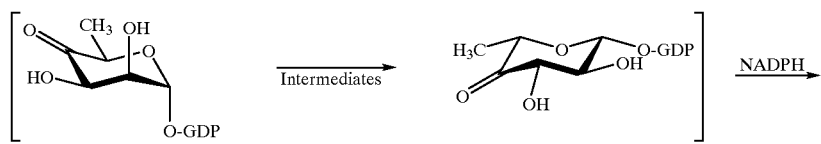
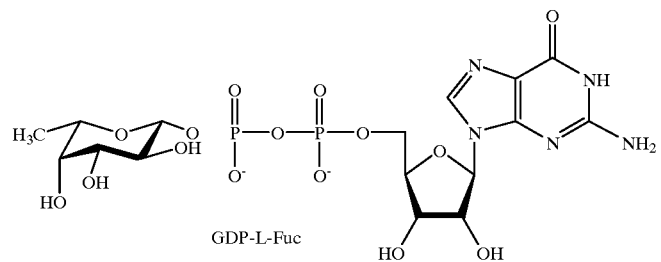

For the synthesis of fucosylated oligosaccharide, a cofactor regeneration system was used in which the released GDP was converted to GTP with the aid of phosphoenolpyruvate (PEP) and pyruvate kinase (PK), and the produced NADP was converted to NADPH with 2-propanol in the presence of alcohol dehydrogenase. Using α1,3/4 fucosyltransferase, Galβ1,3GlcNAc was converted to Galβ1,3(Fucα1,4)GlcNAc. [Dumas et al., *Biomed. Chem. Lett.*, 1:425 (1991)].

D. Recycling Nucleotides

Because glycosyltransferases are often inhibited by nucleotides, it is preferred that the nucleotide concentration be kept to a minimum. The regeneration of nucleoside triphosphates from nucleotide donor sugars permits the use of catalytic amounts of nucleotides, which effectively eliminates undue inhibition of glycosyltransferase activity. The regeneration of the nucleotides able to serve as the high energy bonds of the nucleotide fucosyl donor molecules requires that the reaction conditions support both pyruvate kinase and guanosine 5'-diphosphofucose pyrophosphorylase enzyme reactions. An exemplary recycling system is shown in Scheme 12, below.

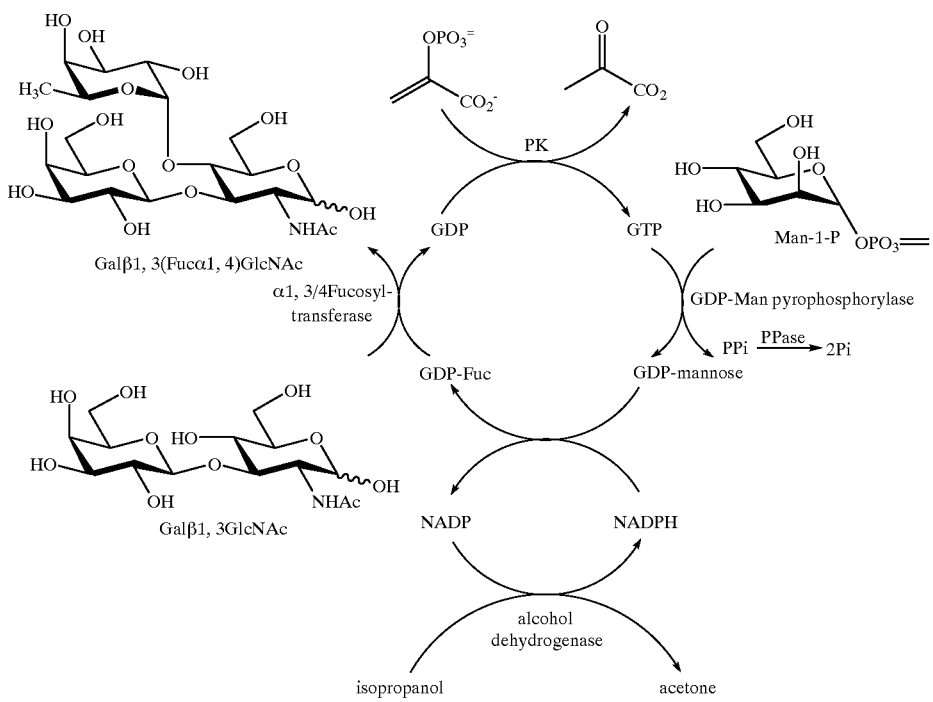

Scheme 12

These activated donor monosaccharide regeneration systems support the glycosyltransferase reactions. The regeneration systems include activated donor monosaccharide, and the enzymes for regenerating the activated nucleotide sugar donor from their respective phosphate donor, nucleotide and sugar donor. The enzymes in the regeneration system include kinases such pyruvate kinase, acetylkinase and 1,6-diphospho fructokinase respectively and nucleotide-sugar-pyrophosphorylases such as GDP-Fuc-PP. Phosphate donors include PEP, acetylphosphate, and D-fructose 1,6-diphosphate.

Some phosphate donors can inhibit the activity of other enzymes in the system and the donors should be selected with care. The nucleotide which is phosphorylated by the kinase should be selected to function as suitable substrate for the nucleotide-sugar-pyrophosphorylase.

The regeneration system described above can be inhibited by a feed back mechanism if the inorganic pyrophosphate concentration is excessive. Use of catalytic amounts of inorganic pyrophosphatase corrects this problem.

E. Sialyl Lewis Ligands

Preferred final products produced by the methods described herein are pharmaceutically active carbohydrates. Such products include sialyl Lewis ligands. (See Schemes 1 and 13, hereinbelow. The R group of Scheme 13 can be hydrogen or an organic group X, as noted before). Sialyl Lewis ligands are defined as any compound that binds to a selecting receptor as described in Polley, et al., *Proc. Natl. Acad. Sci., U.S.A.*, 88:6224–6228 (1991). These ligands are typified by their sialic acid- and fucose-containing terminal structures found on glycoproteins and glycolipids. These ligands include the naturally occurring ligands sialyl $Le^x$ ($SLe^x$) and sialyl $Le^a$ ($SLe^a$). These ligands further include unnatural analogs which bind in a similar manner to the natural receptors of the ligands. For example, ligand analogs can be made with acceptor oligosaccharide analogs for glycosyltransferases. Several acceptor analogs are well known and include the deoxygenated oligosaccharides described in Hindsgaul et. al., *J. Biol. Chem.*, 266:17858–17862 (1991).

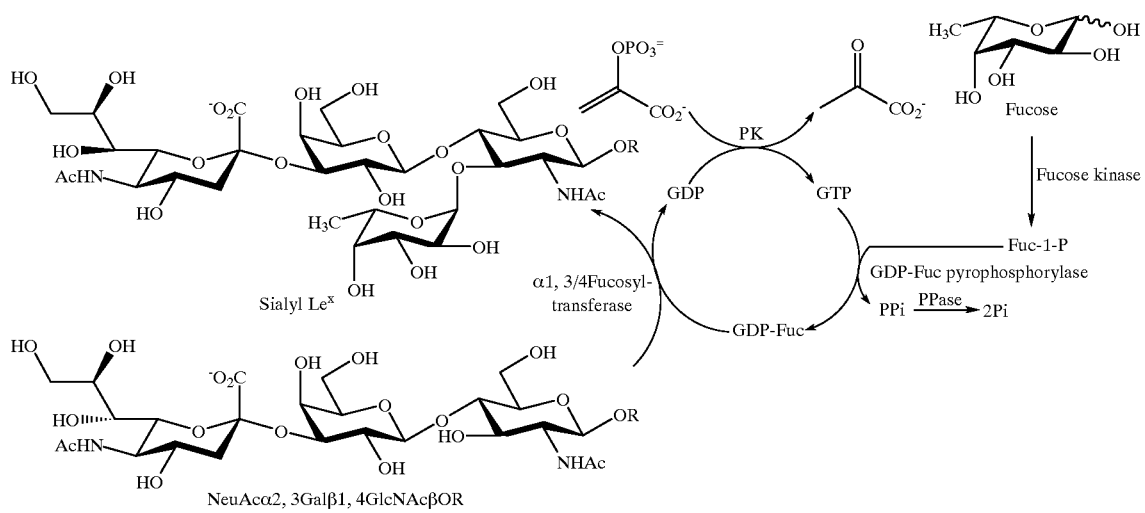

Scheme 13

Ligand analogs are readily made using the above reaction methods and are readily tested using the assay described below. For example, the receptors recognize a ligand that has been modified from the natural site by virtue of a epimerization reaction (from a GlcNAc to a GalNAc), or a change in orientation of one of the glycosidic linkages (an $\alpha 2,6$ to a $\beta 2,6$ linkage). Exemplary procedures are discussed below.

Galactosylation Two multienzyme systems for the synthesis of LacNAc have been developed with in situ cofactor regeneration. One starts with Glc-1-P and uses UDP-Glc pyrophosphorylase (EC 2.7.7.9, UDPGP) and UDP-Gal 4-epimerase (EC 5.1.3.2, UDPGE) [Wong et al., *J. Org. Chem.*, 47:5416 (1982); Auge et al, *Carbohydr. Res.*, 151:147 (1986); Thiem et al., *Angew. Chem. Int. Ed. Engl.*, 30:1163 (1991); Thiem et al., *Synthesis*, 141 (1992)]. This is shown in Scheme 14, below, wherein NAcGlcβOallyl (Compound 40; X is O-allyl) is used as the illustrative acceptor for GalT. UDP-galactose is generated from UDP-Glc with UDPGE; however, this equilibrium favors the formation of UDP-Glc and Glc-1-P has to be prepared separately. Glc-1-P can be prepared using the phosphitylation reaction discussed herein.

Scheme 14

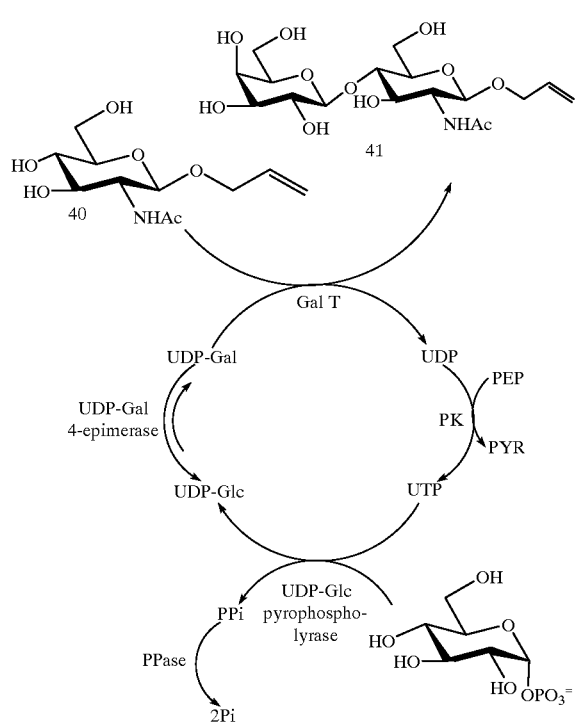

The other uses Gal instead of Glc-1-P, as a donor precursor, and UDPGP, galactokinase (GK; EC 2.7.1.6) and Gal-1-P uridyltransferase (Gal-1-P UT; EC 2.7.7.12). This is shown in Scheme 15 below using 1-$^{13}$C-Gal that is illustrated in the scheme by a hatched circle at the 1-position. GK is specific for galactose, allowing the direct production of Gal-1-P, which is converted to UDP-Gal with Gal-1-P UT and UDP-Glc. The latter system was proven to be suitable for the preparation of [Gal-1-$^{13}$C]-LacNAc.

Scheme 15

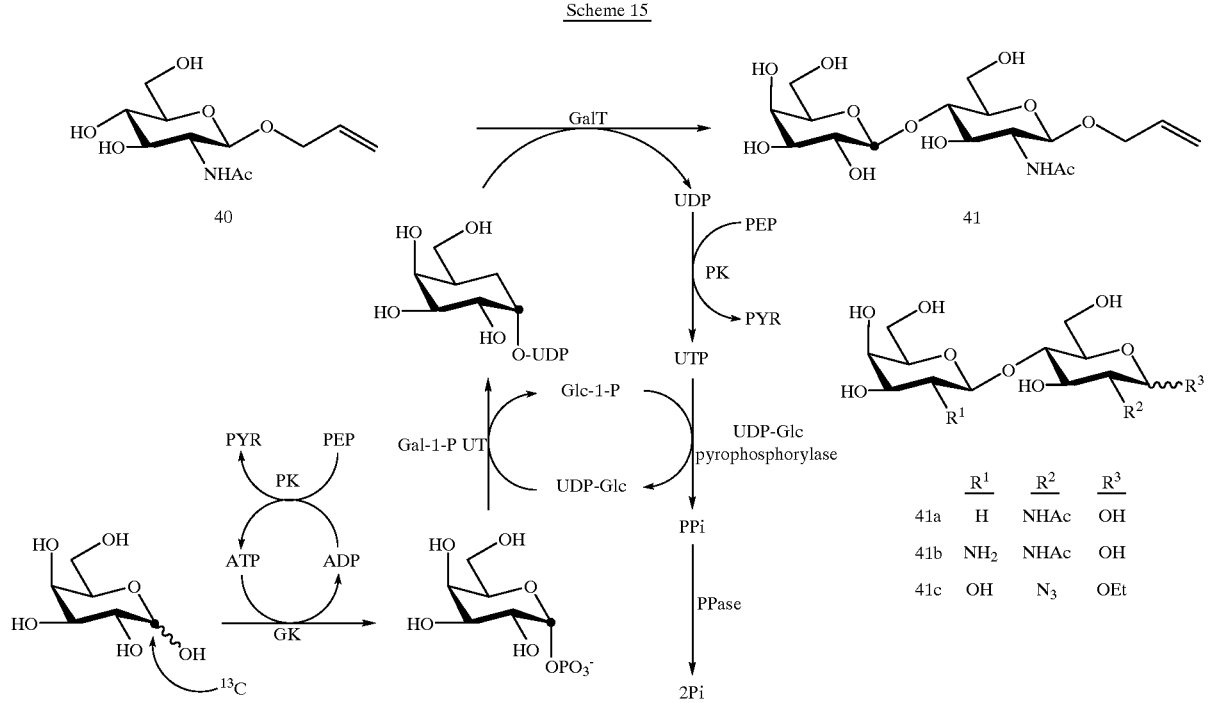

|     | $R^1$ | $R^2$ | $R^3$ |
|-----|-------|-------|-------|
| 41a | H     | NHAc  | OH    |
| 41b | NH$_2$ | NHAc | OH    |
| 41c | OH    | N$_3$ | OEt   |

The multi-enzyme system (Scheme 15) started with 1-$^{13}$C-Gal, [99 Atom Percent, purchased from Isotec Inc., Miamisburg, Ohio), GlcNAcβOallyl (Compound 40), (Lee et al., *Carbohydr. Res.*, 37:193 (1974)] phosphoenolpyruvate (PEP), and catalytic amounts of Glc-1-P, ATP and UDP. UDP was converted into UTP with pyruvate kinase (PK; EC 2.7.1.40) and PEP, and UTP reacted with Glc-1-P catalyzed by UDPGP to produce UDP-Glc. The byproduct inorganic pyrophosphate (PPi) was decomposed by inorganic pyrophosphatase (PPase; EC 3.6.1.1). With Gal-1-P UT, UDP-Glc reacted with $^{13}$C-Gal-1-P, generated from $^{13}$C-Gal and ATP in the presence of GK, to give UDP-$^{13}$C-Gal and Glc-1-P. The $^{13}$C-Gal of UDP-$^{13}$C-Gal was transferred onto the acceptor (GlcNAcβOallyl) by GalT to give [Gal-1-$^{13}$C]-containing LacNAcβOallyl (Compound 41). The produced UDP was again converted to UTP by a reaction of PK and PEP, which reacted with the released Glc-1-P to regenerate UDP-Glc. Using this multienzyme system, [Gal-1-$^{13}$C]-LacNAcβOallyl was obtained in 54 percent yield. The same procedure was also used in the preparation of unlabelled LacNAc and analogs. Exemplary analogs 41a–c are illustrated in the scheme.

Sialylation A multienzyme system for sialylation starts with NeuAc, [Gal-1-$^{13}$C]-LacNAcβOallyl, PEP, and catalytic amounts of ATP and CMP, as is shown in Scheme 16, below. CMP was converted to CDP by nucleoside monophosphate kinase (EC 2.7.4.4, NMK) in the presence of ATP, which was regenerated from its byproduct ADP catalyzed by PK in the presence of PEP, then to CTP with PEP by PK. The CTP was then reacted with NeuAc with CMP-NeuAc synthetase (EC 2.7.7.43) to produce CMP-NeuAc. The byproduct, PPi was hydrolyzed to Pi by PPase. Sialylation of LacNAcβOallyl was accomplished with CMP-NeuAc and α2,3sialyltransferase (α2,3SiaT; EC 2.4.99.6). The released CMP was again converted to CDP, CTP, and finally to CMP-NeuAc. Using this system, [Gal-1-$^{13}$C]NeuAcα2, 3Galβ1,4GlcNAcβOallyl (Compound 42) as well as the unlabelled trisaccharide were prepared.

Scheme 16

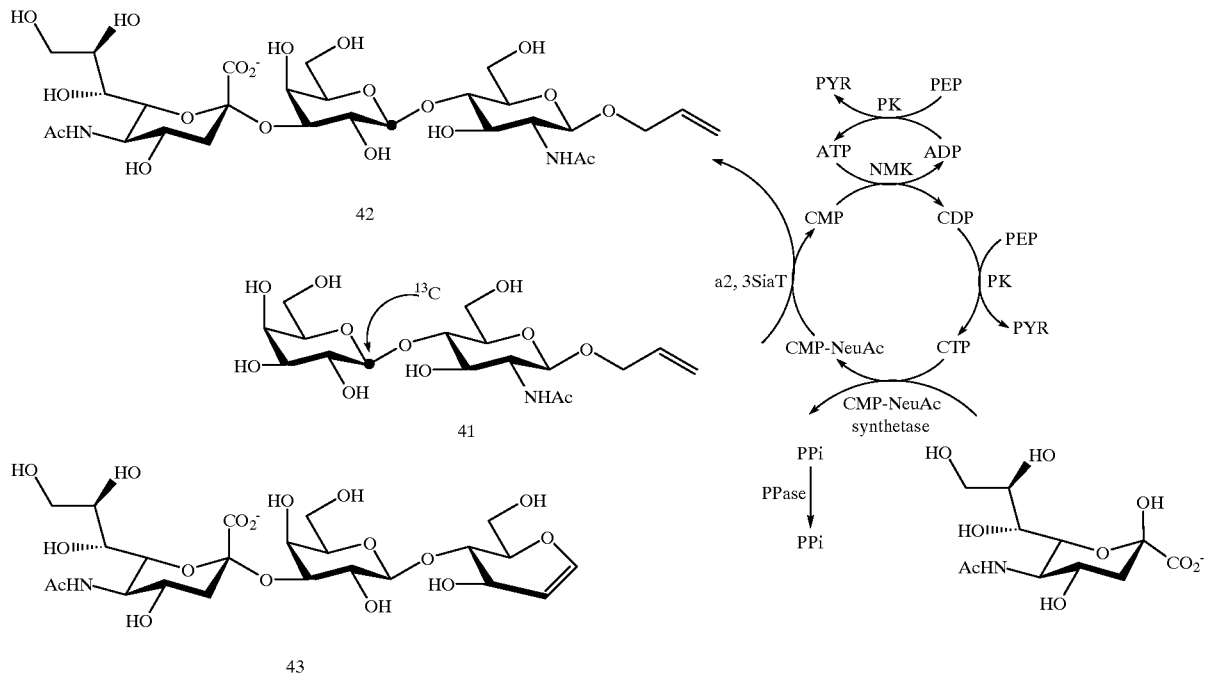

Interestingly, lactal (Galβ1,4Glucal) was also a good substrate for α2,3SiaT, permitting NeuAcα2,3Galβ1, 4Glucal (Compound 43, shown in Scheme 16) to be synthesized in 21 percent yield. Lactal was prepared either chemically [Haworth et al, *J. Chem. Soc.*, 2644 (1930)] or enzymatically using GalT and glucal. (Gautheron-Le Narvor et al., *J. Chem. Soc. Chem. Commun.*, 1130 (1991); Wong et al., *J. Am. Chem. Soc.*, 113:8137–8245 (1991)]. The glycal-containing oligosaccharide such as Compound 43 can be converted to other sialyl Le$^x$ derivatives employing the chemistry developed by Danishefsky and others. [Griffith et al., *J. Am. Chem. Soc.*, 112:5811 (1990); Halcomb et al., *J. Am. Chem. Soc.*, 111:6661 (1989); Kessler, et al., *Angew. Chem. Int. Ed. Engl.*, 29:425 (1990); Thiem et al., *Synthesis*, 696 (1978).] Compound 43 can also be halohydrated as discussed herein to provide the 2-halo-2-deoxy Glc derivatives.

A similar procedure to that shown in Scheme 16 using α2,6 sialyltransferase (EC 2.4.99.1) with Galβ1,4GlcNAc as acceptor carbohydrate provided a 22 percent yield of NeuAcα2,6Galβ1,4GlcNAc after reaction for two days at room temperature.

Fucosylation The cloned human enzyme was used for fucosylation with stoichiometric usage of GDP-Fuc (99 Atom percent, purchased from Isotec Inc., Miamisburg, Ohio) as shown in Scheme 17, below.

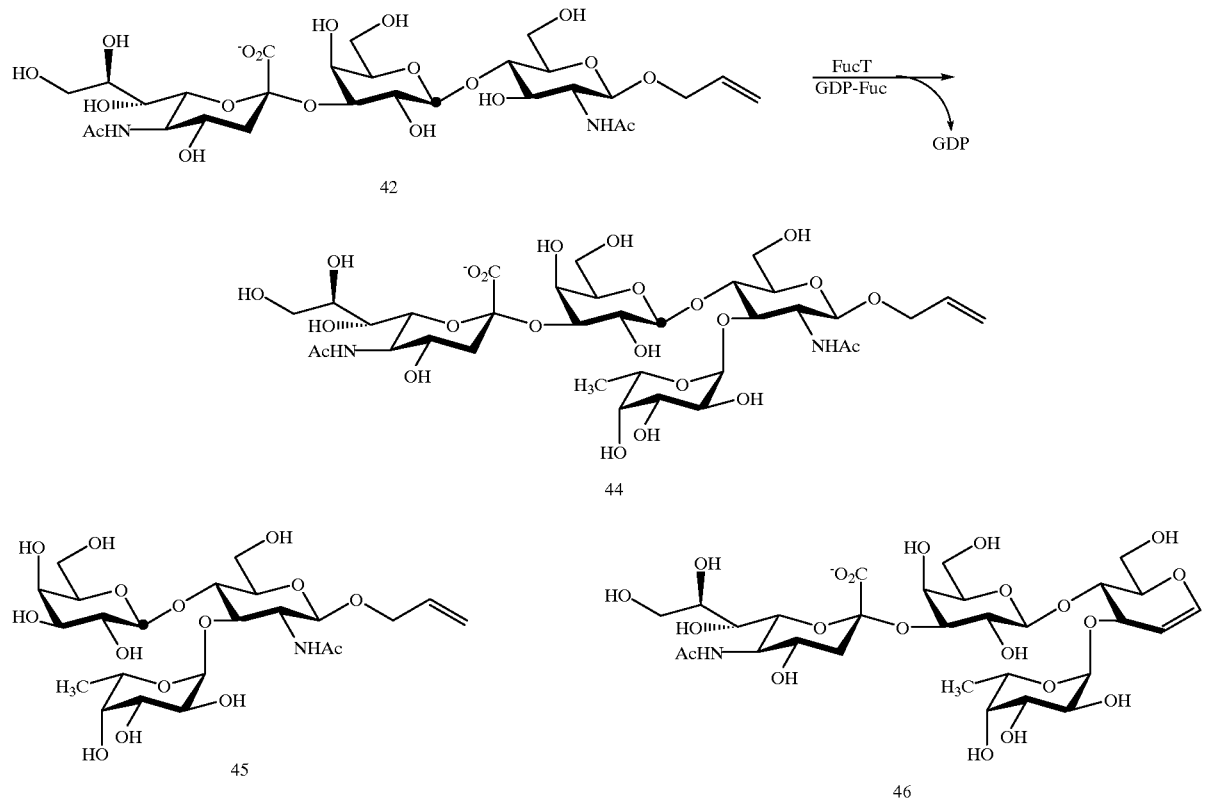

Thus, fucosylation of sialyl LacNAcβOallyl (Compound 42) gave sialyl Le$^x$ Compound 44 after silica gel and BioGel P-2 purification. LacNAcβOallyl (Compound 41) and the sialyl glycal, Compound 43, were also fucosylated to give Le$^x$ trisaccharide Compound 45 and sialyl Le$^x$ glycal Compound 46, respectively, which latter two compounds are shown in Scheme 16. Interestingly, α1,3-FucT and α1,3/4FucT accept Galβ1,4(5-thio)Glc to give a (5-thio)Glc-Le$^x$ analog, Galβ1, 4(fucα1,3)-(5-thio)Glc as shown in Scheme 18, below.

Scheme 18

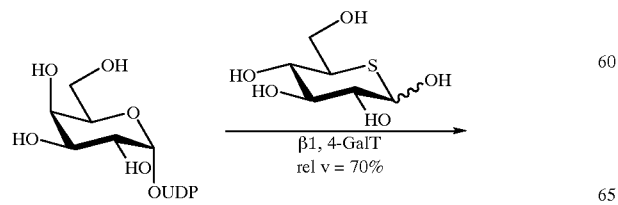

-continued

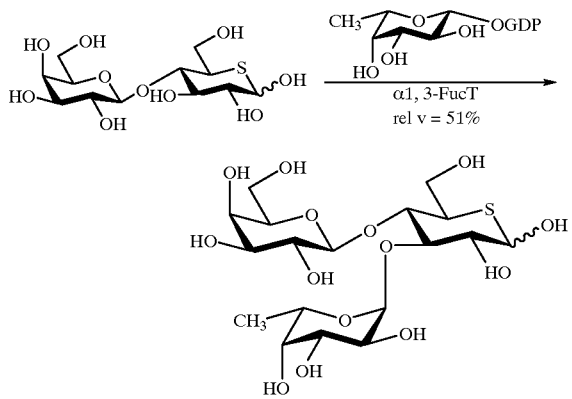

As for the in situ regeneration of GDP-Fuc, the conversion of Man-1-P to GDP-Fuc via GDP-Man based on the biosynthetic pathway of GDP-Fuc in microorganisms was first examined as shown in Scheme 19. The "Acceptor-OH" of Schemes 19 and 20 (hereinafter) is a hydroxyl group of a carbohydrate acceptor substrate such as those listed in Table 2, hereinbefore.

Scheme 19

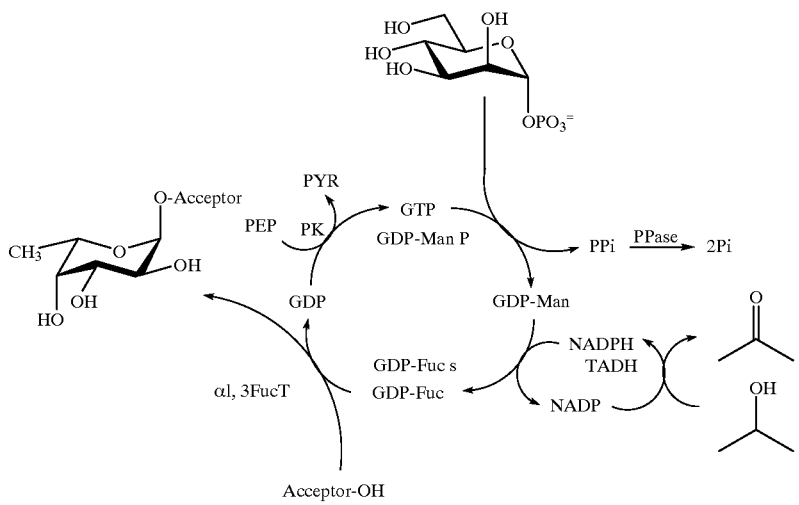

Microbial enzymes were used because of the ease of access. Furthermore, this system permits regeneration of GDP-Man. GDP-Man pyrophosphorylase (GDP-Man PP) has been found in yeast [Munch-Peterson, *Methods in Enzymol.*, 5:171 (1962); Simon et al., *J. Org. Chem.*, 55:1834 (1990)] and GDP-Fuc generating enzymes are known to exist in the bacterium [Ginsburg, *J. Biol. Chem.*, 235:2196 (1960); Ginsburg, *Methods in Enzymol.*, 8:293 (1966)] *Klebsiella pneumonia*. In this regeneration, GTP was generated from GDP in the presence of PEP and PK. Man-1-P reacted with GTP to give GDP-Man by GDP-Man PP from dried yeast cells. GDP-Man was transformed to GDP-Fuc in the presence of NADPH and GDP-Fuc generating enzymes partially purified from the bacterium. The oxidized NADP was recycled back to NADPH by *Thermoanaerobium brockii* alcohol dehydrogenase (TADH) (EC 1.1.1.1) and isopropanol. The production of GDP-Man and GDP-Fuc was confirmed by HPLC, and fucosylation of LacNAcβOallyl and Compound 42 to give Compounds 45 and 44 in 5–10 mg was accomplished. A preparative synthesis of sialyl Le$^x$ with in situ regeneration of GDP-Fuc using purified enzymes is in progress.

An alternative method was to start with Fuc-1-P, which was converted to GDP-Fuc catalyzed by GDP-Fuc pyrophosphorylase (GDP-Fuc P), as shown in Scheme 20, below). [Ishihara et al., *J. Biol. Chem.*, 243:1103 (1968); Ishihara et al., *J. Biol. Chem.*, 243:1110 (1968); Schachter et al., *Methods in Enzymol.*, 28:285 (1972); Richards et al., *Biochim. Biophys. Acta*, 484:353 (1977); Kilker et al., *Biochim. Biophys. Acta*, 570:271 (1979)]. GDP-Fuc P has been partially purified from porcine liver [Ishihara et al., *J. Biol. Chem.*, 243:1110 (1968)] and it has been demonstrated that the regeneration system depicted in Scheme 20 is functional on an analytical scale for the synthesis of Le$^x$ and sialyl Le$^x$.

Scheme 20

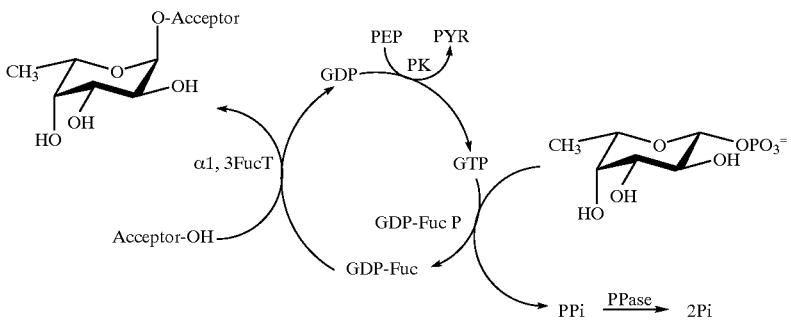

In addition to the sialyl Lewis antigens, SLe$^x$, SLe$^a$, and their respective analogs, the ABH blood-group antigens are also important oligosaccharides. This invention provides a rapid and economical means to obtain all of these compounds. For example to obtain SLe$^a$, which has a structure of NeuAc α2,3 Gal β1,3 (Fucα1,4)GlcNAc, one combines the following three glycosyltransferases: β1,3- galactosyltransferase, α2,3 sialyltransferase and α1,4 fucosyltransferase. The reaction conditions and ancillary substrates enzymes for regeneration of sugar nucleotides are as set forth above.

For H-active oligosaccharides, O-blood group antigen, which has a structure of Fucα1,2Galβ-R where R can be β1,3 GlcNAc-R1 or β1,3 GalNAc-R1 and where R1 is a restricted oligosaccharide, one can combine the following glycosyltransferases: β1,3 galactosyltransferase and α1,2 fucosyltransferase with the appropriate ancillary reaction components and conditions as set forth above for either $SLe^x$ or $SLe^a$ to yield Fucα1,2Galβ1,3GlcNAc-R1. The R1 group of an O-blood group thus constitutes another X group discussed before, as do the R1 groups for the A- and B-blood groups.

For A-active oligosaccharides, A-blood group antigen, which has a structure of GalNAcα1,3(Fuc α1,2) Galβ-R where R can be β1,3GlcNAc-R1 or β1,3GalNAc-R1 and where R1 is a restricted oligosaccharide, one can combine the following glycosyltransferases: β1,3 galactosyltransferase, α1,2 fucosyltransferase, α1,3 N-acetylgalactosaminyltransferase with the appropriate ancillary reaction components and conditions as set forth above to yield GalNAcα1,3(Fuc α1,2)Galβ1,3GlcNAc-R1.

For B-active oligosaccharides, B-blood group antigen, which has a structure of Gal α1,3 (Fuc α1,2) Gal β-R where R can be β1,3 GlcNAc-R1 or β1,3 GalNAc-R1 and where R1 is an restricted oligosaccharide, one can combine the following glycosyltransferases: β1,3 galactosyltransferase, α1,2 fucosyltransferase, α1,3 galactoslytransferase with the appropriate ancillary reaction components and conditions as set forth above to yield Galα1,3(Fuc α1,2)Galβ1,3GlcNAc-R1.

Thus, enzyme-catalyzed step-wise syntheses of oligosaccharides including fucosylated and fucosylated sialylated carbohydrate molecules are contemplated in which the products of each glycosylation reaction are isolated prior to the next glycosylation step. Those glycosylation reactions can, and preferably do, utilize the recycling steps discussed before.

Also contemplated are multiple glycosylations in a single reaction mixture to provide the same fucosylated and fucosylated sialylated carbohydrate molecules. Here also, the recycling reactions discussed before are utilized. In addition, $K_m$ and $V_{rel}$ data such as those provided in Tables 1 and 2 and published values are utilized to adjust concentrations of reactant species to minimize side reactions. Inhibitors as shown in Table 3 can also be used to control product formation.

Still further contemplated are multi-step glycosylation reactions in a single reaction mixture to provide the above products but in which one enzyme or reactant needed for glycosylation is added after the other reactions are substantially complete so that one glycosylation reaction begins after at least one or preferably two other glycosylations are substantially complete. In one exemplary synthesis, all of the reagents and enzymes shown in Scheme 1 except fucosyltransferase (FucT) are added to the reaction mixture and NeuAcα2,3Galβ1,4GlcNAc-OR is formed, as is also shown in Scheme 16 for formation of Compound 42 where R is allyl. Once a compound such as Compound 42 of Scheme 16 has been formed, a FucT such as α1,3fucosyltransferase or α1,3/4fucosyltransferase is added and the fucosylated sialylated carbohydrate such as Compound 44 of Scheme 17 is formed. Alternatively, the FucT enzyme can be present and the fucosyl donor precursor such as fucose can be omitted. Similarly, fucose can be present without its phosphorylating enzyme, fucose kinase.

F. Derivatizing the Fucosylated Products to Form Ligands

The fucosylated products described above are haptens that function best as ligands when bound to larger moieties. Such moieties include proteins, glycoproteins, glycolipids and non-biological analogs of such molecules. Typically, the reducing end of the sugar is linked to a free amine or mercaptan through a glycosidic bond. Liposomes are useful to prepare a multivalent macromolecule. A variety of methods are available for preparing liposomes, as described in, e.g., Szoka et al., *Ann. Rev. Biophys. Bioeng.*, 9:467 (1980), U.S. Pat. Nos. 4,235,871, 4,501,728 and 4,837,028, incorporated herein by reference.

G. Assaying for Sialyl Lewis Ligand Activity

One embodiment of this invention relates to production of sialylated Lewis antigens in both the natural forms and mimetics or analogs. These antigens play a role in intercellular adhesion and play a role in inflammation and other human and mammalian disease states. In order to facilitate the production of these antigens using the invention described herein it is useful to assay the resulting products for their ability to bind to natural sialylated Lewis antigen receptors such as the ELAM and GMP 140 receptors. Such assays have been described in detail in Polley et al., *Proc. Natl. Acad. Sci., U.S.A.*, 88:6224–6228 (1991) and Phillips et al., *Science*, 250:1130–1132 (1990) each of which is hereby incorporated by reference herein.

Although a number of different assays are available, a preferred assay measures the ability of the antigens to block or inhibit the binding of cells carrying the appropriate adhesion receptors and cells expressing the corresponding sialyated Lewis antigen. The binding is assessed visually under a microscope. Preferred receptor expressing cells are activated platelets and endothelial cells. The receptors are a part of a family known as selectins or LEC-CAMs and include LEC-CAM-1, ELAM-1, GMP-140 and CD62. The ligands are found on neutrophils, monocytes and tumor cells.

In a typical assay, neutrophils are isolated by layering heparinized blood over Mono-Poly Resolving Medium (Ficoll-Hypaque-Flow Laboratories), followed by centrifugation for 25 minutes at 2000 rpm and then, a further 25 minutes at 2500 rpm.

Platelets can be isolated following the described procedure. Blood is drawn from a normal human donor into a syringe containing ACD anticoagulant (dextrose, 2.0 g; sodium citrate 2.49 g; and citric acid 1.25 g; to 100 ml with $dH_2O$) at a ratio of 6 parts blood to 1 part anticoagulant. The blood is centrifuged at 800 rpm (approximately 90×g) for 15 minutes at room temperature. The supernatant is collected and centrifuged at 1200 rpm (approximately 400×g) for 6 minutes. The supernatant is removed and centrifuged at 2000 rpm (1200×g) for 10 minutes to pellet the platelets. The platelet button is washed two times with Tyrode-HEPES buffer, pH 6.5 (NaCl 8.0 g; KCl 0.2 g; $NaH_2PO_4.H_2O$ 0.057 g; $MgCl_2.6H_2O$ 0.184 g; $NaHCO_3$ 0.1 g; Dextrose, 1.0 g; and HEPES, 2.383 g; bring to 1 L with DI water, adjust to pH 6.5 with 1N NaOH) followed by one wash in PBS. Platelets are suspended to a concentration of $10^8$/ml in PBS and are activated by incubation for 20 minutes at room temperature with thrombin at a final concentration of 0.25 U/ml.

For the assay, 20 μl of the platelet suspension ($2 \times 10^8$/ml) is placed in an Eppendorf centrifuge tube. An equal volume of the oligosaccharide preparations at concentrations from 200 μg/ml to 0.3 μg/ml, or of glycolipid-liposome preparations (prepared as described, above), at concentrations from 2 μg/ml to 0.25 μg/ml, was added and the tubes were allowed to stand at room temperature for 20 minutes. Twenty μl of the neutrophil preparation (2×10⁶/ml) were then added and the tubes were allowed to stand for a further 20 minutes at room temperature.

Adhesion of activated platelets to the neutrophils is assessed microscopically. Typically, one hundred neutrophils are evaluated. They are scored as positive if two or more platelets were attached and negative if less than two platelets were bound.

H. Improved Means for Producing Glcosyl 1-or 2-P

Phosphorylated sugars having the phosphate on the anomeric carbon (1- or 2-position) are valuable as intermediates in the reactions described herein and several are items of commerce. This invention further provides an improved means of selectively phosphorylating this carbon of a monosaccharide. The improvement involves the use of a trivalent phosphitylating reagent to transfer a phosphityl moiety onto the desired carbon. The resulting phosphite is then used to prepare the corresponding phosphate that itself is used in an enzymatic reaction described herein.

A blocked phosphityl monosaccharide corresponds in structure to Formula I, below:

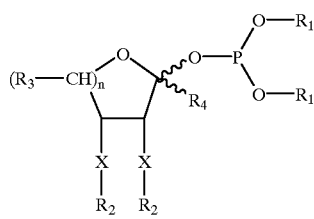

I wherein each $R_1$ is the same or different and is an aryl group such as phenyl or benzyl or a $C_1$–$C_5$ lower alkyl group;

X is independently oxygen or nitrogen;

$R_2$ is independently an acyl, benzyl, silyl or alkyl blocking group or X—$R_2$ together are absent and are replaced by hydrogen;

$R_3$ is independently hydrogen (—H), —CH₃, —OR₂, —CH₂OR₂, —CH(OR₂)—CH(OR₂), —CH(OR₂)—CH(OR₂)—CH(OR₂), —NH₂, or —NHR₂;

$R_4$ is hydrogen (H), carboxyl or $C_1$–$C_5$ alkyl or benzyl carboxylate; and n is 1 or 2, preferably 2.

A contemplated blocked phosphityl monosaccharide thus includes derivatives of sialic acid, KDO, KDN and similar compounds where $R_4$ is a carboxyl or carboxylate ester group. In a preferred group of compounds of formula I, $R_4$ is hydrogen. When that is the case, formula I becomes formula II, below, wherein $R_1$, $R_2$, $R_3$, X and n are as before defined.

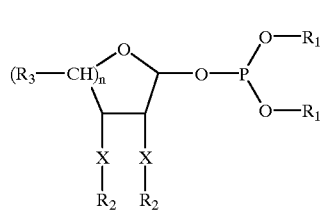

II

It is understood that each $R_1$ group can be different from the other. This stems from the fact that the phosphitylation reagent can be prepared by reaction of PCl₃ with a secondary amine such as diisopropylamine and two moles of alcohol. Thus, by mixing the alcoholic portion of the reaction mixture, one can prepare a phosphitylation reagent and phosphite that can have two different $R_1$ groups such as benzyl and ethyl. Preferably, both $R_1$ groups are the same, and most preferably both are benzyl groups or phenyl groups as those groups can be removed by hydrogenolysis.

It is also to be understood that each X can be oxygen or nitrogen, and compounds having both groups present are particularly contemplated such as the blocked sialyl dibenzylphosphate, Compound 97. $R_2$ blocking groups include acyl groups such as $C_1$–$C_5$ acyl groups such as formyl, acetyl, pivaloyl and pentanoyl groups, benzoyl and phthaloyl groups, alkyl blocking groups and silyl groups. Exemplary alkyl groups include $C_1$–$C_5$ alkyl such as methyl, ethyl, isopropyl, t-butyl, cyclopentyl and pentyl groups. Acetals and ketals formed from $C_1$–$C_5$ alkyl ketones or aldehydes such as the particularly preferred acetone and formaldehyde can also form an alkyl blocking group. Benzaldehyde is also a contemplated acetal-forming blocking group. Such ketals and acetals are well known blocking groups in saccharide chemistry. Exemplary silyl blocking groups include the tri-$C_1$–$C_5$ alkylsilyl groups such as trimethylsilyl, t-butyldimethylsilyl and the like, $C_1$–$C_5$ alkyldiphenylsilyl blocking groups such as a diphenylmethylsilyl group, di-$C_1$–$C_5$ alkylphenyl silyl blocking groups such as a phenyldimethylsilyl group and a triphenylsilyl blocking group.

It is usually preferred that all of the blocking groups be the same or that, if different, they be selectively removable by different reactions. For example, benzyl groups can be removed in the presence of acetyl groups by hydrogenolysis, whereas an acetyl group can be removed in the presence of a benzyl group by treatment with a primary amine such as benzyl amine. Acetyl is a particularly preferred blocking group as an O-acetyl group at the anomeric position (1- or 2-position) can be readily removed in the presence of other O-acetyl groups at the other ring positions by treatment with a primary amine.

It is also noted that X—$R_2$ can be absent and replaced with hydrogen. As such, the blocked monosaccharide is a deoxy monosaccharide as are exemplified by Compounds 97 and 101 through 113.

It should also be understood that where n=2 in formula I, as is preferred for six-membered ring sugars, both ($R_3$—CH) groups need not be the same, and are usually different. For example, for the blocked fucosyl phosphite, Compound 8, discussed previously in regard to Scheme 6, one $R_3$ group is CH₃, whereas the other is O-acetyl (OAc). Similarly, for the blocked mannosyl phosphite, Compound 16, discussed in regard to Scheme 9, one $R_3$ is a CH₂OAc group, whereas the other is an OAc group.

Formula I can alternatively be expressed as formula IA, below, wherein:

each $R_1$ is the same or different and is an aryl group such as phenyl or benzyl or a $C_1$–$C_5$ lower alkyl group;

X is independently oxygen or nitrogen;

$R_2$ is independently an acyl, benzyl, silyl or alkyl blocking group or X—$R_2$ together are absent and are replaced by hydrogen;

$R_3$ is independently hydrogen (—H), —CH₃, —OR₂, —CH₂OR₂, —CH(OR₂)—CH(OR₂), or —CH(OR₂)—CH(OR₂)—CH(OR₂);

$R_4$ is hydrogen (H), carboxyl or $C_1$–$C_5$ alkyl or benzyl carboxylate; and m is zero or 1 such that when m is zero the (CH—X—R$_2$) group is absent and a five-membered ring is formed, and when m is 1 the (CH—X—R$_2$) group is present and the monosaccharide has a six-membered ring, as is preferred.

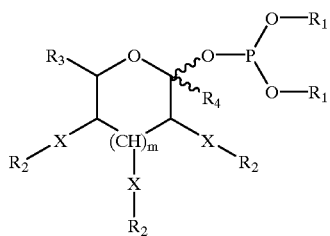

IA

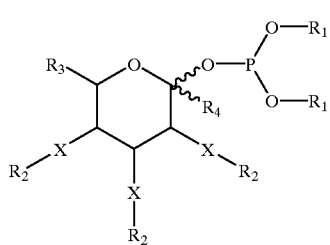

IB

Following the preference for six-membered ring blocked monosaccharide phosphates, formula IA can be expressed as formula IB, above, wherein R$_{1-4}$ and X are as in formula IA.

Following the preference for compounds wherein R$_4$ is hydrogen, formula II can be expressed as formula IIA, below. Following the preference for six-membered ring blocked monosaccharides (where m=1), formula IIA can be expressed as formula IIB, below. R$_{1-3}$, m and X are as in formula IA.

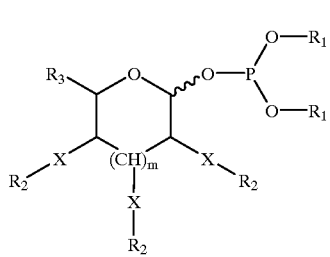

IIA

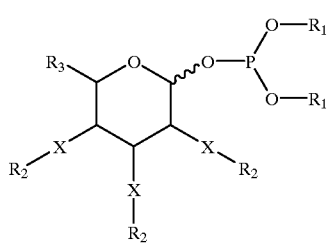

IIB

Except as noted for the differences in R group definitions between formulas I, II, IA, IB and IIA, the identities of X, acyl, silyl, alkyl and the like groups among those formulas are the same.

The trivalent phosphitylating reagents have been previously defined. Available trivalent phosphityl reagents include dibenzyl N,N-diethylphosphoramidite, 2-cyanoethyl N,N,N',N'-tetraisopropylphosphoroamidite or 2-cyanoethyl N,N-diisopropylchlorophosphoamidite.

The process for preparing a blocked monosaccharide phosphite from an unsubstituted (unblocked) monosaccharide is a multistep process beginning with any monosaccharide (aldose or ketose without restriction to confirmation or orientation). The monosaccharide is first blocked at each free hydroxyl (or amine) using a standard blocking reagent such as an acyl, benzyl, silyl or alkyl groups as discussed before. The blocking group, typically a C$_1$–C$_5$ acyl or benzyl group, at the 1- or 2-position is then selectively removed using either a porcine pancreatic lipase or an alkyl or benzyl amine in a nonaqueous polar solvent such as tetrahydrofuran or dichloromethane. The trivalent phosphitylating reagent is then added to the 1- or 2-position under anaerobic conditions using an aromatic secondary or tertiary amine condensing agent such as 1,2,4-triazole, imidazole, tetrazole or pyridinium-p-toulene sulfonate. Triazole or tetrazole are presently preferred condensing agents. The product is then oxidized using an oxidant such as hydrogen peroxide or t-butyl hydroperoxide. The resulting phosphoryl group is deprotected to the phosphate salt (e.g., sodium) using hydrogen/palladium reduction for benzyl derivatives and alkaline treatment for 2-cyanoethyl derivatives.

Thus, using the above reaction, a number of monoglycosyl phosphites and corresponding phosphates have been prepared. Examplary compounds, as the phosphates, were prepared from 2-acetamido-2-deoxy-D-galactose (GalNAc; Compound 89), 2-acetamido-2-deoxy-D-glucose (GlcNAc; Compound 90) D-galactose (Gal, Compound 91), D-glucose (Glc; Compound 92) D-mannose (Man; Compouds 18 and 93), L-rhamnose (Rha; Compound 94), L-fucose (Fuc; Compound 5), and N-acetyl-neuraminic acid (NeuAc; Compound 99). Schemes 21–23, below, outline these reactions. The phosphite of 2-phthalimidoyl-2-deoxy-D-glucose-3,4, 6-triacetate (Compound 100) was also prepared by the process illustrated in Scheme 23 in about 90 percent yield.

Scheme 21

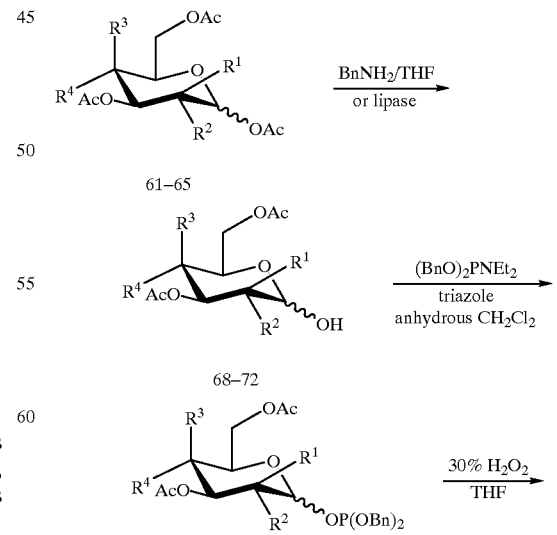

Table 4, below, provides the identities of the various "R" groups ($R^{1-4}$) utilized in the above schemes. Table 5 provides yields and anomeric ratios for various compounds of Schemes 21–23 and Table 4.

Solvents were found to affect the anomeric ratio of the phosphitylated products. Thus, when Compound 70 was phosphitylated in THF, the α:β ratio was found to be 1:6, whereas in chloroform, the ratio changed to 1:2.

TABLE 4 for Schemes 21 and 22

| CP* | $R^1$ | $R^2$ | $R^3$ | $R^4$ |
|---|---|---|---|---|
| 61 | H | NHAc | OAc | H |
| 62 | H | NHAc | H | OAc |
| 63 | H | OAc | OAc | H |
| 64 | H | OAc | H | OAc |
| 65 | OAc | H | H | OAc |
| 66 | H | OAc | OAc | H |
| 67 | OAc | H | H | OAc |
| 68 | H | NHAc | OAc | H |
| 69 | H | NHAc | H | OAc |
| 70 | H | OAc | OAc | H |
| 71 | H | OAc | H | OAc |
| 72 | OAc | H | H | OAc |
| 73 | H | OAc | OAc | H |
| 74 | OAc | H | H | OAc |
| 75 | H | NHAc | OAc | H |
| 76 | H | NHAc | H | OAc |
| 77 | H | OAc | OAc | H |
| 78 | H | OAc | H | OAc |
| 79 | OAc | H | H | OAc |
| 80 | H | OAc | OAc | H |
| 81 | OAc | H | H | OAc |
| 82 | H | NHAc | OAc | H |
| 83 | H | NHAc | H | OAc |
| 84 | H | OAc | OAc | H |
| 85 | H | OAc | H | OAc |
| 86 | OAc | H | H | OAc |
| 87 | H | OAc | OAc | H |
| 88 | OAc | H | H | OAc |
| 89 | H | NHAc | OH | H |
| 90 | H | NHAc | H | OH |
| 91 | H | OH | OH | H |
| 92 | H | OH | H | OH |
| 93 | OH | H | H | OH |

TABLE 4-continued for Schemes 21 and 22

| CP* | R¹ | R² | R³ | R⁴ |
|---|---|---|---|---|
| 94 | H | OH | OH | H |
| 95 | OH | H | H | OH |

*CP = Compound

TABLE 5

Anomeric ratios and chemical yields for steps in Schemes 21–23

| CP* | α:β | yield (%) |
|---|---|---|
| 68 | α only | 71 |
| 69 | α only | 83 |
| 70 | 2:1 | 81 |
| 71 | 3:1 | 85 |
| 72 | α only | 87 |
| 73 | 18:1 | 88 |
| 75 | 7.4:1 | 47 |
| 76 | α only | 93 |
| 77 | 1:2 | 88 |
| 78 | 1:4 | 97 |
| 79 | 3:1 | 80 |
| 80 | 6:1 | 97 |
| 82 | α only | 93 |
| 83 | α only | 97 |
| 84 | 1:2 | 94 |
| 85 | 1:4 | 98 |
| 86 | 3:1 | 98 |
| 87 | 6:1 | 98 |
| 99 | α only | 64 |
| 90 | α only | 39 |
| 91 | 1:2 | 42 |
| 92 | 1:4 | 59 |
| 93 | 3:1 | 72 |
| 94 | 6:1 | 76 |
| 97 | β only | 68 |
| 98 | β only | 95 |
| 99 | β only | 99 |

*CP = Compound

It is noted that the compounds of the schemes above and tables above include mannose and fucose derivatives given different numbers in earlier discussions. Those compouds are renumbered here for ease in presentation of the data. Both numbers are provided in the examples that follow.

Following the reactions outlined in Scheme 23, the synthesis of several further, specific monosaccharide carboxylates of formula I is also contemplated. These compounds are related to D-sialic acid (Compound 101), D- and L-KDN and D- and L-KDO. Structures for exemplary methyl ester (Me) members of those compounds where $R_2$ is acetyl and $R_1$ is benzyl are shown below as Compounds 101–113. The underlying monosaccharide carboxylates can be prepared using sialic acid aldolase-catalyzed reactions as discussed in Gautheron-LeNarvor et al., *J. Am. Chem. Soc.*, 113:7816 (1991) and Sugai et al., *J. Am. Chem. Soc.*, in press.

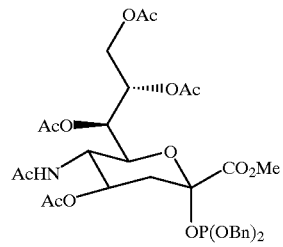

101

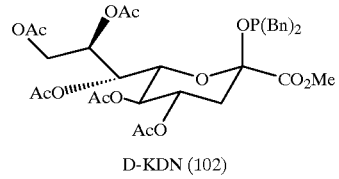

D-KDN (102)

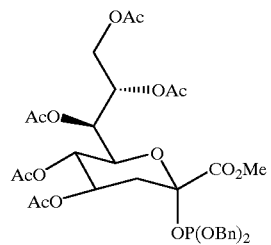

L-KDN (103)

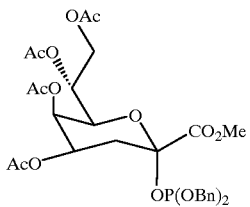

D-KDO (104)

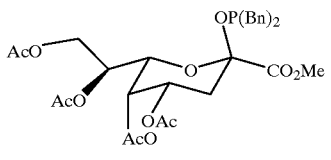

L-KDO (105)

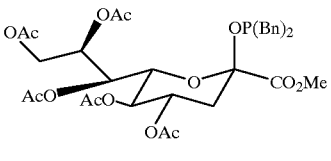

106

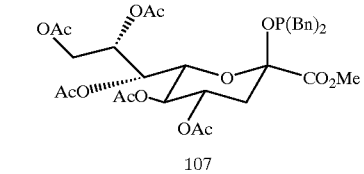

107

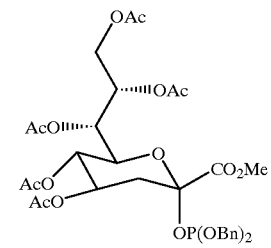

108

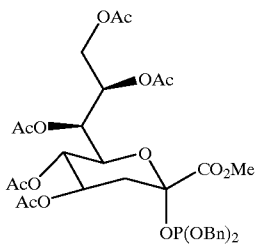

109

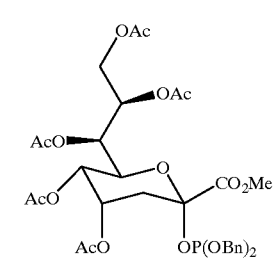

110

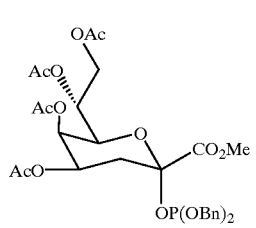

111

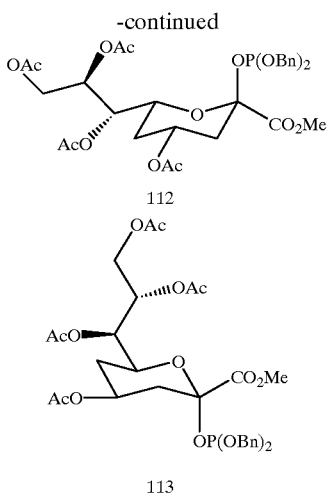

112

113

EXAMPLES

Having presented a general overview of the invention and guidance for coupling the fucosyltransferase reactions to energy generating reactions which use catalytic amounts of inexpensive nucleotides and to other transferase reactions, examples are provided below to provide further details. These examples are provided by way of illustration only and not by way of limitation. Those of skill will readily recognize that many parameters are not critical and could be varied.

Example 1

Chemical synthesis of Fucose 1-phosphate
(Schemes 5 and 6)

(a) 1,2,3,4-Tetra-O-benzoyl-L-fucose (Compound 2)

Benzoyl chloride (21.4 g, 152.3 mmol; 17.7 mL) was added dropwise to a cooled solution of L-fucose (5.0 g, 30.5 mmol) in pyridine (100 mL), at 0–5° C., and the mixture was stirred for three hours at room temperature. The mixture was poured onto ice water and extracted with ethyl acetate (EtOAc). The extracts were successively washed with ice cold dilute HCl aqueous $NaHCO_3$, and brine, dried over anhydrous $MgSO_4$, and concentrated. The product was used for the next step without further purification.

(b) Dibenzylphosphoryl 2,3,4-tri-O-benzoyl-β-L-fucoside (Compound 4)

To a cooled solution of Compound 2 (2.0 g, 3.44 mmol) in $CH_2Cl_2$ (20 mL) and $Ac_2O$ (2 mL) was added dropwise 30 percent HBr—AcOH (8 minutes) at 0–5° C., and the mixture was stirred for two hours at room temperature. The mixture was poured onto ice water and extracted with EtOAc. The extracts were successively washed with water, aqueous $NaHCO_3$, and brine, dried over anhydrous $MgSO_4$, and concentrated to provide Compound 3. Compound 3 was used for the next step without further purification. $^1H$ NMR ($CDCl_3$) δ: 1.36 (3 H, d, J 6.51 Hz, 6-$CH_3$), 4.69 (1H, br q, J 6.56 Hz, H-5), 5.62 (1H, dd, J 3.91, 10.5 Hz, H-2), 5.84 (1H, dd, J 0.97, 3.33 Hz,H-4), 6.01 (1H, dd, J 3.36, 10.50 Hz, H-3), 6.94 (1H, d, J 3.92 Hz,H-1); $^{13}C$ NMR ($CDCl_3$) δ: 15.8, 68.6, 69.2, 70.4, 89.4, 165.4, 165.6, 165.7.

$Ag_2CO_3$ (1.90 g, 6.89 mmol) was added in a cooled (0–5° C.) solution of the above Compound 3, dibenzylphosphate (2.88 g, 10.3 mmol), and MS 3 Å (6 g) in $CH_2Cl_2$—$Et_2O$—$CH_3CN$ (20 mL each) in a round-bottom flask wrapped with aluminum foil to shut-out light. The mixture was stirred for 10 hours at room temperature and filtered through a Celite filter pad, and the filtrate was concentrated. The residue was chromatographed on silica gel, with toluene-EtOAc(2.5:1), to give Compound 4 (2.4 g, 95 percent) as a single product. $^1H$ NMR($CDCl_3$) δ: 1.35 (1H, d,J 6.35 Hz, 6-$CH_3$),4.225 (1H, br dt, J 5.71, 6.70 Hz, H-5), 4.77 (1H, dd, J 7.07, 11.65 Hz, benzylic), 4.86 (1H, dd, J 6.50, 1.63 Hz, benzylic), 5.11 (1H, dd, J 7.51, 11.71 Hz, benzylic), 5.14 (1H, dd, J 7.27, 11.70 Hz, benzylic), 5.58 (1H, dd, J 3.48, 10.44 Hz, H-3), 5.69 (1H, dd, J 7.37, 7.89 Hz, H-1), 5.76 (1H, dd, J 8.03, 3.44 Hz, H-4), 5.90 (1 H, dd, J 8.03, 10.45 Hz, H-2); $^{13}C$ NMR ($CDCl_3$) δ: 16.12, 69.31, 69.35, 69.54, 69.58, 69.63, 69.70, 70.57, 70.83, 71.70, 96.97, 97.00, 127.28, 127.40, 127.89, 128.06, 128.13, 128.26, 128.31, 128.43, 128.58, 128.66, 128.83, 129.06, 129.67, 129.72, 129.77, 129.93, 133.27, 133.41, 133.51, 165.24, 165.45, 165.79. HRMS calcd for $C_{41}H_{37}O_{11}PCs$ ($M+Cs^+$) 869.1128, found 869.1138.

(c) β-L-Fucose 1-phosphate (Compound 5)

Compound 4 (2.32 g, 3.15 mmol) was hydrogenated over 5 percent Pd/C (400 mg) in EtOH (60 mL) and 1 N $NaHCO_3$ (15 mL) for 10 hours. The catalyst was filtered off through a Celite™, filter pad. To a cooled solution of the residue in water (20 mL) was added dropwise 1 N NaOH (20 mL) at 0–5° C., and the mixture was stirred for three hours at room temperature. The mixture was carefully neutralized by the addition of cold 1N AcOH to pH 7.5, and insoluble material was filtered off through a Celite™ pad. The filtrate was diluted to 250 mL, and applied to the column of Dowex 1-X8 [$HCO_2$] (2×15 cm), and eluted with stepwise gradient of $NH_4OAc_2$; water (200 mL), 0.1 M $NH_4OAc_2$ (200 mL), 0.1 M $NH_4OAc_2$ (200 mL), and 0.3 M $NH_4OAc_2$ (200 mL). Fucose was eluted with water and the desired Compound 5 was eluted between 0.2–0.3 M $NH_4OAc_2$. After removal of salt, Compound 5 (700 mg, 82 percent) was obtained. $^1H$ and $^{13}C$-NMR data were in good agreement with those reported by Baker's group. [Nunez et al., Can. J. Chem., 59:2086 (1981)].

(d) 1,2,3,4-Tetra-O-acetyl-L-fucose (Compound 6)

A mixture of L-fucose (3.0 g, 18.2 mmol) and anhydrous NaOAc (50 mg, 0.61 mmol) in acetic anhydride (20 mL) was stirred for two hours at room temperature and then heated at 100° C. for two hours. After cooling, the mixture was poured onto ice water, stirred for two hours, and extracted with chloroform. The extracts were successively washed with aqueous sodium hydrogencarbonate and water, dried over anhydrous magnesium sulfate, and concentrated. The residual syrup was chromatographed on silica gel, with toluene-ethyl acetate (10:1), to give Compound 6 (5.92 g, 98 percent) as a mixture of α and β (1:7 judged by $^1N$ NMR spectrum).

(e) 2,3,4-Tri-O-acetyl-L-fucose (Compound 7 or 74)

i. Chemical Method: A solution of Compound 6 or 67 (3.0 g, 9.0 mmol) and benzyl amine (1.45 g, 13.5 mmol; 1.47 mL) in THF (35 mL) was stirred for a day at room temperature. The mixture was diluted with chloroform and successively washed with ice cold diluted hydrochloric acid, aqueous sodium hydrogencarbonate, and water, dried over anhydrous magnesium sulfate, and concentrated. The residual syrup was chromatographed on silica gel, with toluene-ethyl acetate (1:1), to give Compound 7 or 74 (2.40 g, 92 percent). The $^1H$ NMR spectrum was in good agreement with that reported. [Hennen et al., J. Org. Chem., 53:4743 (1988)].

ii. Enzymatic procedure: A suspension of Compound 6 or 67 (2.5 g, 7.5 mmol) and porcine pancreatic lipase (5.6 g) in 13 percent (v/v) DMF/phosphate buffer (50 mM, pH 7) was stirred for five days at room temperature, in which time the pH was adjusted with N NaOH. The mixture was filtered, and the filtrate was extracted with ethyl acetate. The extract was washed with water, and dried over anhydrous magnesium sulfate. The purification of the product was performed as above to give Compound 7 or 74 (1.1 g, 48.4 percent) as a mixture of α and β(1:1).

(f) Dibenzylphosphoryl 2,3,4-tri-O-acetyl-L-fucoside (Compound 9 or 88)

Dibenzyl N,N-diethylphosphoramidate [Pederson et al., *Tetrahedron*, 47:2643 (1991)] (2.7 g, 8.5 mmol) was added dropwise to a solution of Compound 7 or 74 (1.0 g, 3.4 mmol) and tetrazole (1.0 g, 14.5 mmol) in THF (50 mL) under nitrogen at room temperature, and the mixture was stirred for one hour at room temperature. Ether (50 mL) was added to the mixture, and the organic phase was washed with ice cold diluted hydrochloric acid, aqueous sodium hydrogen carbonate, and water, dried over anhydrous magnesium sulfate and concentrated. The residual syrup was chromatographed on silica gel, with hexane-ethyl acetate (4:1), to give Compound 8 or 81 (1.43 g, 79 percent) as a mixture α and β (1:10). β anomer: $^1$H NMR (CDCl$_3$) δ: 1.22 (3H, d, J 6.50 Hz, 6-CH$_3$), 1.91, 1.99, 2.19 (3H each, s, 3×OAc), 3.85 (1 H, dq, J 1.00, 6.50 Hz, H-5), 4.82–4.96 (4H, m, benzylic protons), 5.02–5.08 (2H, m, H-2, 3), 5.25 (1H, dd, J 0.50, 3.50 Hz, H-4), 5.32 (1H, dd, J 8.00, 10.50 Hz, H-1).

To a cooled solution of Compound 8 or 81 (500 mg, 0.9 mmol) in THF (50 mL) was added 30 percent hydrogen peroxide (7 mL) in one portion, and the mixture was allowed to warm up to room temperature and stirred for 90 minutes. The mixture was diluted with ether and washed with ice cold aqueous sodium thiosulfate, aqueous sodium hydrogencarbonate, and water, dried over magnesium sulfate and concentrated to give Compound 9 or 88 (420 mg, 81 percent). This was used for the next step without further purification. The 1H NMR spectrum was in good agreement with that reported. [Schmidt et al., *Liebigs Ann. Chem.*, 191:121 (1991).] $^1$H NMR (CDCl$_3$) δ: 1.22 (3H, 3, J 10.0 Hz, 6-CH$_3$), 1.91, 1.99, 2.19 (3H each, s, 3×OAc), 3.90 (1H, dq, J 6.50, 7.50 Hz, H-5), 5.00–5.03 (m, H-3, benzylic protons), 5.03–5.12 (m, benzylic protons), 5.26 (1H, dd, J 1.00, 3.50 Hz, H-4), 5.27–5.33 (2H, m, H-1,2). HRMS calcd for C$_{26}$H$_{31}$O$_{11}$PCs (M+Cs)+683.0658, found 683.0658.

(g) L-Fucose-1-phosphate (Compound 5 or 95)

Compound 9 or 88 (5.0 g, 9.1 mmol) was hydrogenated over 5 percent Pd/C (400 mg) in EtOH (70 mL) and N sodium hydrogencarbonate (30 mL) under hydrogen atmosphere for three hours at room temperature, and the catalyst was filtered off. To the cold filtrate was added N NaOH at 0–5° C. until the solution became strongly alkaline (>pH 13). The mixture was stirred for four hours at room temperature and neutralized by the addition of cold N acetic acid to pH 7.5. The mixture was filtered, diluted to 500 mL, applied to a column of Dowex 1-X8 [HCOO$^-$] resin, and eluted with a linear gradient of ammonium bicarbonate (0–0.5 M). The appropriate fractions were collected and lyophilized. Excess ammonium bicarbonate was removed by adding Dowex 50×8 [H$^+$] resin to a solution of the lyophilized powder in water. The resin was filtered off, and the filtrate was lyophilized. A solution of the product was passed through a column of Dowex 50 W-X8 [Na$^+$] with water and lyophilized to give Compound 5 or 95 (2.61 g, 99 percent) as a mixture of α and β (1:10 judged by 1H NMR). $^1$H- and $^{13}$C-NMR spectra were in good agreement with those reported. [Nunez et al., *Can. J. Chem.*, 59:2086 (1981).]

Example 2

Chemical synthesis of GDP-Fucose (Compound 12) (Scheme 7)

Compound 5 was first converted to its triethylammonium salt by passing through a column of Dowex 50 W-X8 [Et$_3$NH$^+$ form] with water and lyophilized. The lyophilized L-fucose-1-phosphate triethylammonium salt (Compound 10) (300 mg, 0.83 mmol) and guanosine-5'-monophosphate morpholidate (Compound 11; 600 mg, 0.83 mmol) were separately dried by co-evaporating with pyridine twice. They were then combined with dry pyridine (20 mL) and the mixture was stirred for 5 days at room temperature, and concentrated. The product was purified with a column of Sephadex 0–25 (superfine) (3×65 cm) twice with water. The appropriate fractions were pooled and passed through a column of Dowex 50 W-Xg (Na$^+$) with water. The fractions were pooled and lyophilized to give Compound 12 (~300 mg) concomitant with a small amount of GMP (judged by $^1$H NMR). $^1$H NMR spectrum was in good agreement with the reported value. [Gokhale et al., *Can. J. Chem.*, 68:1063 (1990).]

Example 3

Enzymatic procedures and assays for converting Mannose-1-P to GDP-Fucose (Schemes 9–11)

(a) Preparation of GDP-mannose Pyrophosphorylase for the Conversion of Man-1-p to GDP-mannose The enzyme for production of the GDP-Mannose is GDP-Mannose pyrophophorylase (GDP-ManPP), which is obtainable from yeast. Most of the GDP-ManPP from the yeast was recovered by ammonium sulfate precipitation (about 80 percent as compared to crude cell free extract) with specific activity about 0.1 Units per mL enzyme solution.

Yeast *Saccharomyces cerevisiae* was grown on the medium: (g/L) Yeast extract, 5; peptone, 10; pH 6.0. The culture was grown at 30° C. with shaking overnight. The cells were harvested with centrifugation and washed with 50 mM tris buffer (pH 7.5) containing 2 mM MgCl$_2$ and 0.5 mM DTT. The cells (about 10 g) were broken by glass beads using Bead-beater (Bioseptic Products, OK) by pulse with one minute intervals for five times. The solution was then centrifuged at 4° C. at 23,000 g for one hour. The supernatant (cell-free extract) was then collected and used for enzyme purification. To partially purify the enzyme, 40–80 percent (at zero degrees C.) of ammonium sulfate precipitation was collected by slowly adding powdered ammonium sulfate to the cell-free extract to 40 percent saturation and centrifuged at 4° C. at 15,000 g for 30 minutes and then the supernatant was further added with ammonium sulfate to 80 percent saturation. After the centrifugation, the precipitate was collected and redissolved in 20 mL of 50 mM tris (pH 7.5) buffer containing 2 mM MgCl$_2$ and 0.5 mM DTT and dialyzed in 4 L of the same buffer overnight (about 18 hours) at 4° C. The activity of this preparation was estimated about 0.1 U/mL base on the HPLC activity assay.

(b) Preparation of GDP-Fucose Synthetic Enzymes for the Conversion of GDP-Mannose to GDP-fucose The initial attempt to use partially purified GDP-fucose synthetic enzyme (collected after ammonium sulfate precipitation) for the conversion of GDP-mannose to GDP-fucose was not successful due to the strong internal oxidation of NADPH. Further purification of the enzyme by passing through DEAD-Sepharose CL-6B column resulted in a higher activity of the enzyme as well as the decrease of NADPH oxidation activity. The enzyme solution at this stage was estimated about 0.05 U/mL based on the NADPH oxidation assay.

The increase of GDP-fucose formation was observed using the HPLC assay. After six hours of reaction, the yield of GDP-fucose was estimated about 9 percent based on the added mannose 1-phosphate. It is expected that a higher yield can be obtained if enzyme solutions with higher activities can be prepared. During the reaction, the degradation of GDP-mannose was observed. This degradation can be prevented by the addition of potassium fluoride. This is due to the contamination of other enzymes in the enzyme preparation. If pure enzyme can be used, the addition of fluoride salt may not be needed.

Bacteria, *Klebsiella pneumonia* ATCC 12658, were grown on 2 L of a medium that contained 10 g of casamino acid (Difco), 5 g of yeast extract, 3 g of $K_2HPO_4$, 1 g of $KH_2PO4$ and 5 g of D-glucose per liter (pH 7.0). After incubation of 37° C. for 18 hours, the cells were harvested by centrifugation (10,000×g, 50 minutes, 4° C.) and resuspended in 50 mM tris buffer containing 0.5 mM DTT (pH 7.5). The cells were disrupted by a French pressure cell at 16,000 lb/in. The cell debris was removed by centrifugation at 23,000×g for 60 minutes and the supernatant (cell-free extract) was used for enzyme purification. The cell-free extract (50 mL) from 2 liter culture was treated with 60 mg of protamine sulfate and the resulting precipitate was removed after centrifugation. Solid ammonium sulfate was then added slowly stirring until 70 percent saturation is reached (0.436 g per mL at zero degrees C.). After the centrifugation, the precipitate was collected and resuspended in 20 mL of the buffer (50 mM tris containing 0.5 mM DTT, pH 7.5), and dialyzed overnight (about 18 hours) at 4° C. in 4 liters of the same buffer. The resulting solution (20 mL) was then passed through the DEAE-Sepharose CL-6B column (Pharmacia) (3×30 cm) that was previously equilibrated with the same buffer. The enzyme was eluted with a linear gradient from 0 to 1 mM NaCl in the same buffer (total 400 mL). The active fraction was pooled and dialyzed in 2 L of 50 mM tris buffer containing 0.5 mM DTT (pH 7.5). This enzyme preparation was used for synthesis directly. The activity was estimated about 0.5 U/mL based on IPLC and NADH oxidation assay.

(c) Assay for Enzyme Activity

A HPLC system was used to determine the formation of GDP-Man and GDP-Fucose. The column partisil 5 SAX (Whatman Co.), 4.6×12.5 cm, with particle size 5 m was used. The mobile buffer was 0.1 M phosphate buffer (pH 3.5) with flow rate 0.5 mL/minute (pressure 600 psi). The compounds were detected by UV detector at 254 nm. The retention time for GDP-mannose was about 8.9 minutes and GDP-fucose was about 13 minutes. The activity of the GDP-mannose pyrophosphorylase was assayed by following the formation of GDP-mannose from α-mannose-1-phosphate and GTP by HPLC analysis. The reaction contained 10 μmole of tris-HCl, 1 μmole α-mannose 1-phosphate, 1 μmole GTP and partially purified enzyme in total volume 0.5 mL. After incubation at 30° C. for a period of time depending on the enzyme activity. The reactant (100 μL) was withdrawn and centrifuged through Ultrafree filter unit (10,000 MW cutout, Millipore). The filtrate (5 μL) was then injected into the HPLC for the measurement of GDP-mannose formation. The quantification of GDP-mannose was estimated by the GDP-mannose standard solution prepared from purified GDP-mannose (Sigma). One unit is equal to 1 μmole GDP-mannose formed per minute under the assayed conditions.

The activity measurement for the conversion of GDP-D-mannose to GDP-L-fucose can be followed either by the spectrophotometric determination of NAHPH oxidation or directly measuring the formation of GDP-L-fucose by HPLC method. Because the enzyme preparations contain NADPH oxidase activity, it is necessary to determine simultaneously the rate of NADPH oxidation in the absence of substrate. In two cuvettes, 1 mL of the 50 mM tris buffer (pH 7.5) containing 0.2 μmole of NADPH and enzyme solution, to the other cuvette, 0.1 μmole of GDP-mannose was added. The rate of decrease in optical density of the two cuvettes at 340 nm was determined. The difference in rate of NADPH oxidation is the measurement of conversion process. FIG. 1 shows a typical assay in which absorbance line A is the control cuvette without GDP-mannose, and line B is the same solution further containing 1 μmole of GDP-mannose. One unit is equal to 1 μmole NADPH oxidation per minute under assay conditions.

For an HPLC assay, the reaction medium was 1 mL of tris buffer (pH 7.5) containing 1 μmole of GDP-D-mannose, 0.2 μmole NADPH, 2 μmole KF, 2 U *T. brokii* alcohol dehydrogenase, 10 μL isopropanol and the proper enzyme solution. After incubation for a certain time period (one hour), 100 μL of the reactant was withdrawn and centrifuged through Ultrafree filter unit (10,000 MW cutout, Millipore). The filtrate (5 μL) was then injected to HPLC for the measurement of GDP-fucose formation. The quantification of GDP-fucose was estimated by the GDP-fucose standard prepared from purified GDP-fucose (Sigma). One unit is equal to 1 μmole GDP-fucose formed per minute under assayed conditions. FIG. 2 shows three exemplary HPLC plots at zero time (A), about three hours (B) and about six hours (C) after the reaction was initiated. As noted before, GDP-mannose elutes at about 8.9 minutes, whereas GDP-fucose elutes at about 13 minutes.

Example 4

Enzymatic Synthesis of GDP-fucose from Mannose 1-phosphate

To 5 mL of the reaction solution, 5 μmole Man-1-phosphate, 1 μmole NADPH, 5 μmole GTP, 5 μmole PEP, 100 U pyruvate kinase, 50 μl isopropanol, 5 U *T. brokii* alcohol dehydrogenase, 1 μmol $MgCl_2$, 100 U inorganic phosphatase, 5 μmol KF, 0.1 U GDP-mannose pyrophosphatase solution and 0.05 U GDP-fucose synthetic enzymes were added and incubated at 30° C. for six hours, the formation of GDP-fucose was determined by HPLC assay.

Example 5

Preparation of Galβ1,3(Fucα1,4)GlcNAc Using in situ Generation of GDP-fuc

A mixture of GTP Na salt (6.0 mg, 10 μmol), Man-1-P K salt (3.5 mg, 10 μmol), Galβ1,3GlcNAc (3.8 mg, 10 μmol), NaF (0.42 mg, 10 μmol), NADPH (9.4 mg, 10 μmol), PEP K salt (4.1 mg, 20 μmol), $MgCl_2$—$6H_2O$ (2.6 mg, 10 μmol), $MnCl_2$—$4H_2O$ (2 mg, 10 μmol), 2-propanol, (50 μL), ADH (12 U), PK (200 U), PPase (100 U), crude enzyme preparation of GDP-mannose pyrophosphorylase (1.0 mL), and crude enzyme preparation of GDP-Fuc producing enzyme (1.0 mL) in 100 mM tris buffer (pH 7.5) and diluted to 3 mL. α1,3/4-Fucosyltransferase (0.01 U) was added to the mixture and the resulting mixture was stirred under Ar for three days at room temperature. The mixture was filtered and the filtrate was applied to a column of Dowex 1-X8 [OH⁻] form followed with a column of Dowex 50W-X8 [H⁺] with water. The fractions were collected and lyophilized. The residual material was purified with a column of Sephadex G-25 (superfine) with water. The appropriate fractions were pooled and lyophilized to give Galβ1,3(Fucα1,4)GlcNAc. Its ¹H-NMR spectrum was in good agreement with that reported. [Dumas et al., *Biomed. Chem. Lett.*, 1:425 (1991).]

Example 6

Chemical Synthesis of Mannose 1-phosphate (Compound 18 or 93: Scheme 9)

(a) 1,2,3,4,6-Penta-O-acetyl-D-mannose (Compound 14 or 65)

D-mannose (Compound 13; 5.0 g, 27.8 mmol was dissolved in anhydrous pyridine (30 mL) and cooled to 0–5° C. in an ice-bath. Acetic anhydride (20 mL) was added slowly to the solution and the mixture was permitted to stir at room temperature for eight hours. The mixture was poured into ice water and extracted with ethyl acetate. The extracts were subsequently washed with cold hydrochloric acid, water, cold saturated sodium bicarbonate, water, saturated sodium chloride, water and dried over anhydrous sodium sulfate. The organic layer was concentrated in vacuo and used for the next step without further purification. Compound 14 or 65; 10.6 g, 98 percent yield, pure α-isomer.

(b) 2,3,4,6-Tetra-O-acetyl-D-mannose (Compound 15 or 72)

The pentaacetate (Compound 14 or 65; 10.0 g, 25.6 mmol was dissolved in tetrahydrofuran and 1.5 equivalents of benzylamine (4.6 mL) were added. The mixture was stirred at room temperature for a day. It was then extracted with ethyl acetate and washed subsequently with cold hydrochloric acid, water, cold saturated sodium bicarbonate, water, cold saturated sodium chloride, water and dried over anhydrous sodium sulfate. The solvent was removed in vacuo and the residual syrup was chromatographed on silica gel with ethyl acetate:hexane (2:3, v/v) to give Compound 15 or 72 (7.8 g, 87 percent yield, pure α-isomer) $^1$H NMR (CDCl$_3$) δ: 2.00, 2.05, 2.11, 2.17 (3H, s, 4×CH$_3$CO), 4.01–4.15, (1H, m, 5-H), 4.21–4.29 (2H, m, 6-H), 5.24 (1H, d, 1-H), 5.26–5.27 (1H, m, 2-H), 5.30–5.34 (1H, d, J=12.03 Hz, 4-H), 5.41–5.45 (1H, dd, J 3.36, 9.99 Hz, 3-H).

(c) Dibenzylphosphityl 2,3,4,6-tetra-O-acetyl-D-mannoside (Compound 16 or 79)

The mannose-tetraacetate (Compound 15 or 72) (1.5 g, 4.31 mmol) was dissolved in anhydrous tetrahydrofuran (30 mL) and stirred under nitrogen at room temperature. 1,2,4-Triazole (1.5 g, 21.7 mmol) was added into the solution and stirred until it dissolved. To the solution was added dibenzyl-N,N-diethyl-phosphoryamidite (10.0 g, 31 mmol) and the mixture was stirred for one hour. 50 Milliliters of ether were added to the solution and the reaction mixture was subsequently extracted with cold saturated sodium bicarbonate, water, cold saturated sodium chloride and water, and dried over anhydrous sodium sulfate. The organic extract was then concentrated in vacuo and the residual syrup was purified through a silica gel column with ETOAc-hexane (1:4 v/v) as the solvent system (pure α-isomer) to give Compound 16 or 79.

$^1$H NMR (CDCl$_3$) δ: 2.0–2.3 (12H, 4s, 4×CH$_3$CO), 3.92–3.98 (1H, dd, 6-Ha), 4.05–4.1 (1H, m, 5-H), 4.18–4.24 (1H, dd, 6-Hb), 4.85–5.12 (4 h m, CH$_2$Ph), 5.22–5.24 (1H, m, 2-H), 5.28–5.32 (1H, t, 4-H), 5.38–5.42 (1H, dd, 3-H), 5.48–5.52 (1H, dd, 1-H).

(d) Dibenzyl phosphoryl 2,3,4,6-tetra-O-acetyl-D-mannoside (Compound 17 or 86)

Compound 16 or 79 dissolved in anhydrous tetrahydrofuran and cooled to –76° C. with a dry ice/acetone bath and 30 percent hydrogen peroxide (7 mL) was added to the solution in a single portion. The solution was allowed to warm up to room temperature and stirred for 90 minutes. The excess hydrogen peroxide was quenched by adding ice cold sodium thiosulfate. 100 Milliliters of ether were then added and the extraction was carried out as described above to give Compound 17 or 86 which was used for the next step without further purification.

(e) D-Mannose-1-phosphate (Compound 18 or 93)

Compound 17 or 86 was hydrogenated over 5 percent Pd/C (400 mg) in ethanol (30 mL) and in sodium bicarbonate (10 mL) under hydrogen atmosphere for two hours. The catalyst was filtered off and the filtrate was concentrated. Sodium hydroxide was added dropwise to the residue at 0–5° C. until pH of the reaction mixture was above 12. The mixture was stirred for three hours at 4° C. and then neutralized by the addition of cold N acetic acid to pH 7.2. The mixture was filtered, diluted to 400 mL, applied to a Dowex 1-X8 column (HCOO$^-$ form, 2×28 cm), and eluted with a linear gradient of ammonium bicarbonate (0–0.6 M). The fractions containing D-mannose-1-phosphate were pooled and lyophilized. Excess ammonium bicarbonate was removed by washing the lyophilized powder with Dowex 50W-X8 (hydrogen form) to give Compound 18 or 93 as the disodium salt.

Example 7

Enzymatic Halohydrations

A. General Procedure for Chloroperoxidase-Catalyzed Halohydration (Schemes 3, 4 and 4a)

A reaction mixture containing 20 mL citric-phosphate buffer (pH 3), 1 mmol of glycal, 5 mmol of potassium halide and 1170 units of the enzyme was added 600 μL of H$_2$O$_2$ (30 percent). The reaction was continued for 30 minutes (iodohydration), three hours (bromohydration) or three days (chlorohydration) at room temperature. The solvent was removed under reduced pressure, and methanol was added to the residue. The insoluble material was filtered off, and the solvent was removed under reduced pressure. The residue was purified with C8 reversed phase silica gel column chromatography to yield 2-deoxy-2-halo sugars. The products were converted to peracetates by a standard method (pyridine, catalytic amount of 4-dimethylaminopyridine, acetic anhydride, one day) and purified by silica gel column chromatography for characterization.

(1) Peracetate of Compound 20

$^1$H-NMR (CDCl$_3$) δ: α-isomer: 2.04 (3H, s), 2.08 (3H, s), 2.10 (3H, s), 2.21 (3H, s), 4.05 (1H, dd, J=2.5, 12.5 Hz, H-6), 4.08 (1H, dd, J=3.5, 11 Hz, H-2), 4.28 (1H, ddd, J=2, 4, 10 Hz, H-5), 4.31 (1H, dd, J=4, 12.5 Hz, H-6), 5.09 (1H, dd, J=9, 10 Hz, H-3), 5.52 (1H, dd, J=9, 11 Hz, H-4), 6.36 (1H, d, J=3.5 Hz, H-1) ppm.

β-isomer: 2.03 (3H, s), 2.09 (3H, s), 2.11 (3H, s), 2.18 (3H, s), 3.88 (1H, ddd, J=2.4, 4.5, 10.5 Hz, H-5), 3.90 (1H, dd, J=9, 10.5 Hz, H-2), 4.11 (1H, dd, J=2.5, 12.5 Hz, H-6), 4.32 (1H, dd, J=4.5, 12.5 Hz, H-6), 5.03 (1H, dd, J=9, 10 Hz, H-3), 5.34 (1H, dd, J=9, 10.5 Hz), 5.81 (1H, d, J=9 Hz, H-1) ppm. $^{13}$C-NMR (CDCl$_3$) d: 20.52–20.67 (4×C), 47.50, 62.10, 68.46, 72.85, 74.36, 93.11, 167.91–172.10 (4×C) ppm. HRMS (M+Na$^+$): calcd 433.0110/435, found 433.0112/435.

(2) Peracetate of Compound 21

$^1$H-NMR (CDCl$_3$) δ: α-isomer: 2.07 (3H, s), 2.10 (3H, s), 2.11 (3H, s), 2.17 (3H, s), 4.19 (1H, ddd, J=2.5, 4.5, 10.5 Hz, H-5), 4.17 (1H, dd, J=2.5, 10.5 Hz, H-6), 4.23 (1H, dd, J=4.5, 12.5 Hz, H-6), 4.43 (1H, dd, J=2, 4 Hz, H-2), 5.21 (1H, dd, J=4, 9.5 Hz, H-4), 5.45 (1H, t, J=10 Hz, H-4), 6.32 (1H, d, J=2 Hz, H-1) ppm. $^{13}$C-NMR (CDCl$_3$) δ: 20.60, 20.66, 20.75, 20.86, 47.77, 61.82, 65.54, 68.75, 71.25, 93.11, 167.20–171.90 (4×C) ppm.

β-isomer: 2.07 (3H, s), 2.10 (3H, s), 2.12 (3H, s), 2.18 (3H, s), 3.82 (1H, ddd, J=2.5, 5, 9.5 Hz, H-5), 4.13 (1H, dd, J=2.5, 12.5 Hz, H-6), 4.27 (1H, dd, J=5, 10.5 Hz, H-6), 4.60 (1H, dd, J=3.5, 1.5 Hz, H-2), 5.00 (1H, dd, J-4, 9.5 Hz, H-3), 5.43 (1H, t, J-9.5 Hz, H-4), 5.74 (1H, d, J=1.5 Hz, H-1) ppm. $^{13}$C-NMR (CDCl$_3$) δ: 20.60–20.85 (4×C), 51.05, 61.82, 65.27, 71.01, 73.04, 90.01, 167.20–171.90 (4×C) ppm. HRMS (M+Na$^+$): calcd 433.0110/435, found 433.0115/435.

(3) Peracetate of Compound 22

$^1$H-NMR (CDCl$_3$) δ: β-isomer: 2.04 (3H, s), 2.07 (3H, s), 2.16 (3H, s), 2.19 (3H, s), 4.08 (1H, dd, J=9, 11.5 Hz, H-2), 4.10–4.15 (3H, m, 2×H-6 & H-5), 5.15 (1H, dd, J=3, 11.5 Hz, H-3), 5.35 (1H, d, J=3 Hz, H-4), 5.84 (1H, d, J=9 Hz, H-1) ppm. $^{13}$C-NMR (CDCl$_3$) δ: 20.42, 20.52, 20.61, 20.66, 46.35, 60.89, 67.03, 71.94, 72.78, 93.43, 168.31–170.90 (4×C) ppm. α-isomer: $^{13}$C-NMR (CDCl$_3$) δ: 20.42–20.66 (4×C), 44.39, 67.04, 67.69, 68.64, 69.39, 91.05, 167.01–170.86 (4×C) ppm. HRMS (M+Na$^+$): calcd 433.0110/435, found 433.0119/435.

(4) Compound 23

$^1$H-NMR (CDCl$_3$), β-isomer: 1.12 (3H, d, J=6.5, CH$_3$), 3.45 (1H, dd, J=1, 3 Hz, H-4), 3.52 (1H, dd, J=3, 10.5 Hz, H-3), 3.58 (1H, qd, J=1, 6.5 Hz, H-5), 3.69 (1H, dd, J=8.5, 10.5 Hz, H-2), 4.45 (1H, d, J=8.5 Hz, H-1). $^{13}$C-NMR (CDCl$_3$), β-isomer: 16.71, 58.04, 72.13, 73.56, 76.03, 98.78 ppm. β-isomer: 16.71, 54.71, 67.25, 71.13, 74.55, 94.20 ppm. HRMS (M+Na$^+$): calcd 248.9738/251, found 248, 9730/251.

(5) Peracetate of Compound 25

$^1$H-NMR (CDCl$_3$) δ: β-isomer: 2.05 (3H, s), 2.08 (3H, s), 2.16 (3H, s), 2.18 (3H, s), 4.06 (1H, dd, J=9, 11.5 Hz, H-2), 4.07–415 (3H, m, 2×H-6 & H-5), 5.09 (1H, dd, J=3, 11.5 Hz), 5.39 (1H, d, J=3 Hz, H-4), 5.75 (1H, d, J=9 Hz, H-1) ppm. $^{13}$C-NMR (CDCl$_3$), β-isomer: 20.21–22.55 (4×C), 55.30, 60.87, 66.84, 71.86, 72.74, 93.53, 168.20–180.21 (4×C) ppm. α-isomer: 20.1–22.55 (4×C), 53.46, 61.04, 67.44, 68.67, 69.51, 90.94, 168.20–180.21 (4×C) ppm. HRMS (M+Na$^+$): calcd 389.0615/391, found 389.0610/391.

(6) Peracetate of Compound 27

$^1$H-NMR (CDCl$_3$) δ: β-isomer: 2.04 (3H, s), 2.07 (3H, s), 2.12 (3H, s), 2.17 (3H, s), 4.06–4.17 (4H, m, H-2, 2×H-6 & H-5), 5.13 (1H, dd, J=3.5, 10 Hz, H-3), 5.25 (1H, d, J=3.5 Hz, H-4), 5.91 (1H, d, J=9.5 Hz, H-1) ppm. $^{13}$C-NMR (CDCl$_3$), β-isomer: 20.5–22.50 (4×C), 24.98, 60.94, 67.10, 72.16, 74.10, 94.15, 168.20–179.36 (4×C) ppm; α-isomer: 20.5–22.50 (4×C), 29.87, 60.63, 67.68, 68.31, 69.42, 92.16, 168.20–179.36 (4×C) ppm. HRMS (M+Na$^+$): calcd 480.9972, found 480.9999.

B. Chloroperoxidase-Catalyzed Halohydration of Disaccharide Glycals and Sialal (1) Halohydration of Compound 28 (Scheme 4)

40 Microliters of 30 percent H$_2$O$_2$ were added to a mixture of Compound 28 (20 mg, 0.065 mmol), KBr (38.6 mg, 0.32 mmol) and chloroperoxidase (76 units) in citrate buffer (1.4 mL; pH 3), and the reaction mixture was gently stirred for three hours at room temperature. The solvent was removed under reduced pressure, and MeOH was added to the residue. The insoluble material was filtered off, and the filtrate was concentrated under reduced pressure. The residue was purified with a C$_8$-reverse phase silica gel column chromatograph to give a mixture of D-galactopyranosyl-β(1,3)-2-bromo-2-deoxy-D-glucopyranose, Compound 29, (10 mg) and D-galactopyranosyl-β(1,3)-2-bromo-2-deoxy-D-mannopyranose, Compound 30 (10 mg) in 76 percent yield. The products were acetylated with Ac$_2$O and pyridine in the presence of catalytic amount of DMAP for the characterization.

(2) Chloroperoxidase-Catalyzed Halohydration of 2, 3-Dehydro-N-acetyl-neuraminic Acid (Compound 35) (Scheme 3)

100 Microliters of 30 percent H$_2$O$_2$ were added to a mixture of Compound 34 [Meindl, *Hoppe-Seyler's Z. Physiol. Chem.*, 1350:1088 (1969); 50 mg, 0.17 mmol], KBr (102 mg, 0.857 mmol), and chloroperoxidase (200 units) in citrate buffer (3.5 mL; pH 3), and the reaction mixture was gently stirred for 30 minutes at room temperature. The solvent was removed under reduced pressure, and MeOH was added to the residue. The insoluble material was filtered off, and the filtrate was concentrated under reduced pressure. The residue was purified with a BioGel P-2 column and further purified with a C$_8$-reverse phase silica gel column chromatograph CH$_3$CN/H$_2$O (5:1) to give 2-bromo-2-deoxy-N-acetylneuraminic acid (Compound 35 (43 mg, 65 percent). The product was peracetylated with Ac$_2$O and pyridine in the presence of catalytic amount of DMAP followed by methylation with MeI and Cs$_2$Co$_3$ for the characterization.

$^1$H-NMR (CDCl$_3$) δ: 1.95, 2.04, 2.05, 2.10, 2.19, 2.20, (3H, s, each, OAc and NHAc), 3.83 (3H, s, COOCH$_3$), 4.11 (1H, ddd, J=8.7, 10.6, 10.7 Hz, H-5), 4.22 (1H, dd, J=6.4, 12.5 Hz, H-9), 4.32 91H, dd, J-1.8, 10.6 Hz, H-6), 4.57 (1H, dd, J=5.15 (1H, ddd, J=2.4, 5.5, 6.4 Hz, H-8), 5.31 (1H, dd, J=1.8, 5.5 Hz, H-7), 5.43 (1H, d, J=8.7 Hz, NH), 5.67 (1H, dd, J=3.8, 10.7 Hz, H-4). HRMS: calcd for C$_{22}$H$_{30}$NO$_{14}$BrCs (M+Cs$^+$) 743.9904/746, found 743.9900/746.

(3) 1,3,6,2',3',4',6'-Heptaacetyl-D-galactopyranosyl-β(1,4)-2-bromo-2-deoxyglycopyranose (Compound 32) and -2-deoxymannopyranose (Compound 33)

According to the general procedure, a 1:1 mixture of Compound 32 and Compound 33 (155 mg, 71 percent) was obtained from Galβ(1,4)Glucal (Compound 31) (96.5 mg). The ratio of Compounds 32 and 33 was determined from the integral ratio of the anomeric protons of Compounds 32 and 33. Compounds 32 and 33 were obtained as α:β anomeric mixtures: Compound 32 (α:β=1:3), Compound 33 (α:β– 2:1).

HRMS of Compound 32 and Compound 33: calcd for C$_{26}$H$_{35}$O$_{17}$BrCs (M+Cs$^+$) 831.0112/833, found 831.0112/833.

$^1$H-NMR of the mixture of Compounds 32 and 33: $^1$H-NMR (CDCl$_3$) δ1.96, 1.97, 1.98, 1.981, 2.03, 2.04, 2.05, 2.06, 2.070, 2.074, 2.075, 2.08, 2.12, 2.13, 2.132, 2.15, 2.16, 2.166 (—OCH$_3$), 3.84 (dd, J=1.6, 9.0 Hz, H-2 of Glu of β anomer of Compound 32), 3.73–4.22 (m), 4.40 (dd, J=2.2, 3.8 Hz, H-2 of a anomer of Compound 33), 4.43–4.47 (m), 4.46 (dd, J=1.0, 7.6 Hz), 4.55 (d, J=8.0 Hz), 4.57 (dd, J=1.6, 4.0 Hz, H-2 of α anomer of Compound 33), 4.59 (d, J=8.0 Hz), 4.93 (dd, J=3.5, 5.1 Hz), 4.96 (dd, J=3.5, 4.96 Hz), 4.99 (dd, J=3.5, 10.5 Hz, H-3' of β anomer of Compound 32, 5.03 (dd, J=3.8, 8.8 Hz), 4.07–5.12 (m), 5.16 (dd, J=8.0, 10.5 Hz), 5.20–5.26 (m), 5.35–5.38 (m), 5.70 (d, J=1.6, H-1 of β anomer of Compound 33), 5.76 (d, J=9.0 Hz, H-1 of β anomer of Compound 32), 6.26 (d, J=2.2 Hz, H-1 of α anomer of Compound 33), 6.30 (d, J=3.4 Hz, H-1 of α anomer of Compound 32). $^{13}$C-NMR (CDCl$_3$) 20.52, 20.61, 20.65, 20.75, 20.80, 20.84, 20.88, 20.93, 46.27, 47.95, 48.13, 51.26, 60.77, 60.91, 61.08, 61.49, 61.67, 61.79, 62.04, 66.56, 66.62, 66.71, 66.75, 68.97, 69.03, 69.09, 69.14, 69.30, 70.68, 70.72, 70.75, 70.78, 70.82, 70.86, 70.91, 70.94, 70.98, 71.16, 71.73, 73.44, 73.68, 73.80, 74.13, 74.29, 76.32, 76.61, 89.77, 90.34, 92.98, 93.13, 100.84, 101.19, 101.45, 168.42, 168.45, 168.53, 168.92, 169.14, 169.22, 169.36, 169.59, 169.65, 170.08, 170.13, 170.16, 170.29, 170.36, 170.46.

(4) 1,3,6,2',3',4',6'-Heptaacetyl-D-galactopyranosyl-β(1,3)-2-bromo-2-deoxyglycopyranose (Compound 29) and -2-deoxymannopyranose (Compound 30)

According to the general procedure, a 1:1 mixture (Compounds 29 and 30) (66 mg, 76 percent) was obtained from Galβ(1,3)Glucal (Compound 28) (38.6 mg). Compounds 29 and 30 were isolated by silica gel column chromatography (AcOEt/n-hexane, 5/2), as α:β anomeric mixtures: Compound 29 (α:β=1:10), Compound 30 (α:β=12:5).

β anomer of Compound 29: $^1$H-NMR (CDCl$_3$) δ: 1.98, 2.04, 2.07, 2.08, 2.09, 2.15, 2.17 (3H, each, s, OAc×7), 3.78 (1H, ddd, J=1.8, 4.6, 9.7 Hz, H-5 of Glu), 3.85 (1H, t, J=9.5 Hz, H-2 of Glu), 3.89 (1H, t, J=7 Hz, H-5 of Gal), 3.96 (1H, t, J=10.0 Hz, H-3 of Glu), 4.07 (1H, m, H-6 of Gal), 4.09 (1H, dd, J=1.8, 12.4 Hz, H-6 of Glu), 4.13 (1H, dd, J=7.0, 11.1 Hz, H-6 of gal), 4.25 (1H, dd, J=4.6, 12.4 Hz, H-6 of Glu), 4.89 (1H, d, J=7.7 Hz, H-1 of Gal), 4.97 (1H, t, J=9.6 Hz, H-4 of Glu), 5.03 (1H, dd, J=3.4, 10.0 Hz, H-3 of Gal), 5.13 (1H, dd, J=7.7, 10.0 Hz, H-2 of Gal), 5.36 (1H, d, J=3.4 Hz, H-4 of Gal), 5.75 (1H, d, J=9.0 Hz, H-1 of Glu).

HRMS: calcd for C$_{26}$H$_{35}$O$_{17}$BrCs (M+Cs$^+$) 831.0112/833, found 831.0112/833.

$^{13}$C-NMR (CDCl$_3$) δ: 20.55, 20.64, 20.68, 20.71, 20.75, 20.96, 50.11, 60.93, 61.62, 66.73, 68.53, 68.96, 70.62, 70.82, 72.87, 77.21, 81.30, 92.86, 101.61, 168.77, 169.03, 169.35, 170.13, 170.20, 170.36, 170.67.

α anomer of Compound 30: $^1$H-NMR (CDCl$_3$) δ: 4.24 (1H, bd, J=3.0 Hz, H-2 of Man), 4.55 (1H, d, J=8.0 Hz, H-1 of Gal), 5.01 (1H, dd, J=3.4, 10.5 Hz, H-3 of Gal), 5.18 (1H, dd, J=7.8, 10.5 Hz, H-2 of Gal), 5.32 (1H, t, J=8.7 Hz, H-4 of Man), 5.39 (1H, dd, J=1.0, 3.4 Hz, H-4 of Gal, 6.30 (1H, d, J=3.0 Hz, H-1 of Man).

β anomer of Compound 30: $^1$H-NMR (CDCl$_3$) δ: 4.45 (1H, dd, J=2.0, 3.5 Hz, H-2 of Man), 4.55 (1H, d, J=8.0 Hz, H-1 of Gal), 5.01 (1H, dd, J=3.4, 10.5 Hz, H-3 of Gal), 5.20 (1H, dd, J=7.8, 10.5 Hz, H-2 of Gal), 5.30 (1H, t, J=7.4 Hz, H-4 of Man), 5.39 (1H, dd, J=1.0, 3.4 Hz, H-4 of Gal), 5.80 (1H, d, J=2.0 Hz, H-1 of Man).

HRMS: calcd for C$_{26}$H$_{35}$O$_{17}$BrCs (M+Cs$^+$) 831.0112/833, found 831.0110/833.

$^{13}$C-NMR 20.57, 20.65, 20.76, 20.87, 20.95, 21.01, 21.04, 48.21, 60.98, 61.19, 62.01, 62.61, 66.75, 66.82, 68.43, 68.52, 70.71, 70.88, 71.05, 72.03, 73.36, 74.74, 75.93, 77.23, 90.08, 92.80, 100.10, 100.24, 168.23, 169.13, 169.22, 169.73, 170.18, 170.40.

(5) Sialyl α(1,3)Galβ(1,4) [Fucα(1,3)]-2-bromo-2-deoxyglucopyranose (Compound 37a) and -2-bromo-2-deoxymannopyranose (Compound 37b)

According to the general procedure, a 1:1 mixture of Compounds 37a and 37b (3.5 mg, 56 percent) was obtained from NeuAc(2,3)Galβ(1,4)[Fucα(1,3)]glucal Compound 36 (5.5 mg). The ratio of Compounds 37a and 37b was determined from the integrated ratio of the methyl protons of fucose.

$^1$H-NMR of the mixture of Compounds 37a and 37b: $^1$H-NMR (D$_2$O) δ1.17 (d, J=6.0 Hz, CH3 of Fuc), 1.18 (d, J=6.0 Hz, CH3 of Fuc), 1.80 (t, J=12.7 Hz, H-3ax of NeuAc), 2.02 (s, NHAc), 2.75 (dd, J=5.0, 12.7 Hz, H-3 eq of NeuAc), 3.45–4.13 (m), 4.48 (d, J=8.0 Hz, H-1 of Gal), 4.49 (d, J=8.0 Hz, H-1 of Gal), 5.0–5.04 (m), 5.18–5.22 (m), 5.38–4.42 (m).

Example 8

General Procedure for Bromohydration with NBS

To a solution of 1 mmole of glucal in a mixture of 3.6 mL CH$_3$CN-1.5 mL H$_2$O was added 1 mmole of N-bromosuccinimide (NBS) at room temperature. The reaction was continued for three hours at the same temperature. The solvent was removed under reduced pressure, and the residue was chromatographed on silica gel column chromatography. The products were converted to peracetates by pryidine and acetic anhydride in the presence of a catalytic amount of 4-dimethylaminopyridine and purified by silica gel column chromatography for characterization.

(a) 1,3,6,2',3',4',6'-Heptaacetyl-D-galactopyranosyl-β(1,4)-2-bromo-2-deoxyglucopyrannose (Compound 32) and -2-deoxymannopyranose (Compound 33)

According to the general procedure, a 1:2.5 mixture of Compounds 32 and 33 (30 mg, 78 percent) was obtained from Galβ(1,4)Glucal (Compound 31) (17 mg). The ratio of Compounds 32 and 33 was determined from the integrated ratio of the anomeric protons. Compounds 32 and 33 were obtained as α:β anomeric mixtures: Compound 32 (α:β=3:5), Compound 33 (α:β=5:2).

(b) Methyl 5-acetamido-2,4,7,8,9-penta-O-acetyl-3-bromo-3,5-dideoxy-β-D-erythro-L-manno-2-nonulopyranosonate (methyl peracetyl Compound 35, Compound 35a) and methyl 5-acetamido-2,4,7,8,9-penta-O-acetyl-3-bromo-3,5-dideoxy-α-D-erythro-L-gluco-2-nonulopyranosonate (Compound 35b)

Chemical bromohydration was carried out according to the general procedure, and the products were converted to peracetates, followed by esterification with methyl iodide in the presence of an equimolar amount of cesium carbonate to obtain a mixture of Compounds 35a and 35b (155 mg, 74 percent). The production ratio of Compounds 35a and 35b was determined from the integral ratio of methyl ester protons.

$^1$H-NMR spectra of Compounds 35a and 35b were in good agreement with a previous report.

Compound 35b: $^1$H-NMR (CDCl$_3$) δ: 1.90, 2.03, 2.08, 2.10, 2.12, 2.15 (3H, s, each OAc and NHAc), 3.78 (3H, s, COOCH$_3$), 4.04 (1H, dd, J=6.0, 12.4 Hz, H-9), 4.09 (1H, d, J=10.0 Hz, H-3ax), 4.33 (1H, ddd, J=10.0, 10.6, 10.7 Hz, H-5), 4.36 (1H, dd, J=2.4, 12.4 Hz, H-9'), 5.10 (1H, ddd, J=2.4, 6.0, 6.1 Hz, H-8), 5.25 (1H, dd, J=2.5, 10.7 Hz, H-6), 5.30 (1H, dd, J=10.0, 10.6 Hz, H-4), 5.38 (1H, dd, J=2.5, 6.1 Hz, H-7), 5.90 (1H, d, J=10.0 Hz, NH).

Example 9

Expression of Galβ1,3/4GlcNAc α2,3 Sialyltransferase

High yield expression of a soluble Galβ1,3/4GlcNAc α2,3 sialyltransferase was accomplished in a baculovirus expression system using cDNA encoding a fusion protein between the pre-insulin signal peptide and the catalytic domain of the sialyltransferase. The cDNA encoding the fusion protein was constructed by Wen et al. in the plasmid vector pGIR199. [Huseh et al., *J. Biol. Chem.* 261:4940

(1986)]. To isolate a DNA fragment containing the entire coding sequence, the unique Eco RI site at the 3' end of the chimera was first digested, the overhang was made blunt, and synthetic linkers containing an Nhe 1 site were ligated. The resulting plasmid was digested with Nhe 1 to release the fusion protein cDNA, and this fragment was cloned at the unique Nhe 1 site in pBlueBac, and baculovirus expression system transfer vector, under the control of the baculovirus polyhedrin promoter (Invitrogen; San Diego, Calif.). All recombinant DNA manipulations were performed in the conditions recommended by the enzyme manufacturers' instruction using standard protocols. [Sambrook et al., *Molecular Cloning: A Laboratory Manual,* 2nd ed., Cold Spring Harbor Laboratory Press, Plainview, N.Y. (1989)].

Creation of recombinant baculovirus was done using the MaxBac expression system (Invitrogen) following exactly the protocols recommended by the manufacturer. Briefly, plasmid and wild type virus DNA were mixed and used to transect Sf-9 cells by the calcium phosphate method. Recombinant virus was produced by the transferred cells and shed into the culture medium, and repetitively plaque purified at limiting dilution. Several clonal plaques isolated were analyzed for the ability to cause secretion of α2,3 NeuT into the infected cell medium by testing an aliquot of the media directly for α2,3 NeuT activity in a sialyltransferase assay. The isolate that directed the highest levels of α2,3 NeuT secretion was designated rBv2,3ST, and was expanded to 500 mL by infection of fresh Sf-9 cells. α2,3 NeuT activity was assayed using a modification of the published assay with 0.9 mM. These manipulations are illustrated schematically in Scheme 24, below.

Scheme 24

-continued

Example 10

Galβ1,3GlcNAcβ1,3Galβ1,4Glc as acceptor

To produce large amounts of α2,3 NeuT, rBv2,3ST was used to infect Sf-9 cells in monolayer culture, and generally yielded 2–3 units of α2,3NeuT activity secreted per $10^8$ infected cells when grown in Excell-400 media (JRH Biosciences, Lenexa, Kans.). Units of activity (mmol/min) are defined by multiplication of the assay results by a factor of 1.6 to give activity at $V_{max}$. Conditioned media from rBv2,3ST-infected cells were collected 72 hours post-infection and the recombinant α2,3 NeuT was partially purified in one chromatography step. Three liters media containing α2,3 NeuT were filtered and concentrated to approximately 250 mL in an Amicon CH2PRS spiral cartridge system equipped with an S1Y10 cartridge. The unit was then run in diafiltration mode to desalt to the concentrated supernatant with three volumes of 10 mM cacodylic acid, 25 mM NaCl, 25 percent glycerol, pH 5.3 (buffer A). Samples were then applied to a column (2.5×17 cm) of S-Sepharose Fast Flow (Pharmacia) equilibrated with buffer A at a flow rate of 2 mL/minutes. After all of the sample has been loaded, the column was washed with buffer A until the $OD_{280}$. of the column effluent had returned to baseline (1.6 column volumes).

α2,3 NeuT was then eluted from the column with 50 mM cacodylic acid, 1M NaCl, 25 percent glycerol pH 6.5. Fractions containing α2,3 NeuT were pooled and dialyzed overnight (about 18 hours) against 1L 50 mM cacodylic acid, 0.5 M NaCl, 50 percent glycerol, pH 6.0, and then stored at −20° C.

Example 11

Galactosylation (a) LacNAcβOallyl from (Compound 41; Scheme 14)

A mixture of Compound 40 [Lee et al., *Carbohydr. Res.,* 37:193 (1974)] (2.0 g, 7.65 mmol), Glc-1-P (2.74 g, 7.65 mmol), PEP (K salt), 1.6 g, 7.65 μmol), $NAD^+$ (193 mg, 0.25 mmol), $MnCl_2.4H_2O$ (79.2 mg, 0.4 mmol), $MgCl_2.6H_2$ (162.6 mg, 0.8 mmol), DTT (306 mg, 2 mmol), KCl (1.04 g, 15 mmol), NaN$_3$ (20 mg, 0.31 mmol) and UDP (90 mg, 0.19 mmol) in HEPES buffer (100 mM, pH 7.5; 200 mL) was adjusted with 10N and N NaOH to pH 7.5 and the enzymes, UDPGE (10 U), UDPGP (20 U), PK (100 U), GalT (5 U) and PPase (100 U) were added to the solution. The mixture was gently stirred under an argon atmosphere at room temperature (25° C.) for five days. The mixture was concentrated and chromatographed on silica gel, with CHCl$_3$—EtOAc—MeOH (5:2:2 to 5:2:3) to give a disaccharide, which was further purified with Sephadex G-25, with water, to give LacNAcβOallyl (Compound 41) (1.7 g, 50 percent); $^1$H NMR (D$_2$O) δ: 2.00 (3H, s, NHAc), 3.49 (1H, dd, J 7.84, 9.97 Hz, H-2 of Gal), 3.52–3.57 (1H, m, H-5 of GlcNAc), 3.63 (1H, dd, J 3.31, 10.04 Hz, H-3 of Gal), 3.65–3.75 (8 H, m), 3.79 (1H, dd, J 5.10, 12.27 Hz, H-6a of GlcNAc), 3.88 (1H, br d, J 3.32 Hz, H-4 of Gal), 3.95 (1H, dd, J 2.14, 12.27 Hz, H-6b of GlcNAc), 4.43 (1H, d, J 7.81 Hz, H-1 of Gal), 4.55 (1H, d, J 8.28 Hz, H-1 of GlcNAc), 5.21–529 (2H, m, allylic), 5.83–5.90 (1H, m, allylic), $^{13}$C NMR (D$_2$O) δ: 22.6, 55.5, 60.5, 61.5, 69.0, 70.9, 71.4, 72.9, 75.2, 75.8, 78.8, 100.4, 103.3, 118.6, 133.7.

(b) From Scheme 15, Compound 1-$^{13}$C-41

A solution of Compound 40 (1.15 g, 4.4 mmol), 1-$^{13}$C-Gal (99 Atom percent, purchased from Isotec Inc., Miamisburg, Ohio; 800 mg, 4.4 mmol), PEP K salt (1.82 g, 8.8 mmol; 95 percent), UDP (90 mg, 0.19 mmol), ATP (100 mg, 0.18 mmol), cysteine (116 mg, 0.96 mmol), DTT (183 mg, 1.2 mmol), MgCl$_2$.6H$_2$O (244 mg, 1.2 mmol), MnCl$_2$.4H$_2$O (118 mg, 0.6 mmol), KCl (179 mg, 2.4 mmol) and Glc-1-P (77 mg, 0.22 mmol) in HEPES buffer (100 mM, pH 7.5; 120 mL) was adjusted by 10 N and N NaOH to pH 7.5, and the enzymes, GK (10 U), PK (200 U), PPase (10 U), Gal-1-P UT (10 U), UDPGP (10 U) and GalT (10 U) were added to the solution. The mixture was gently stirred under an argon atmosphere at room temperature (ca. 25° C.) for three days. The mixture was concentrated in vacuo and the residue was chromatographed on silica gel, with EtOAc—MeOH (2:1), to give a disaccharide, which was further purified with a column of Sephadex G-25, with water, to give Compound 1-$^{13}$C-41 (106 g, 57 percent). $^1$H NMR (D$_2$O) δ: 2.00 (3H, s, NHAc), 3.48–3.52 (1H, m, H-2 of Gal), 4.43 (1H, dd, $J_{H-1,H-2}$ 8.32, $J_{H-1,13C-1}$ 162.33 Hz, H-1 of Gal), 4.54 (1H, d, J 8.32 Hz, H-1 of GlcNAc). HRMS calcd for $^{12}$C$_{16}$ $^{13}$CH$_{29}$NO$_{11}$Na (M+Na$^+$) 447.1672, found 447.1681.

(c) 2-Deoxy-D-galactopyranosyl-b(1,4)-2-acetamido-2-deoxy-glycopyranose Compound 41b (36 Percent): both $^1$H NMR spectrum of its heptaacetate and $^{13}$C NMR spectrum of Compound 41a are in good agreement with those reported. [Thiem et al., *Anaew. Chem. Int. Ed. Enal.*, 30:1163 (1991)].

(d) 2-Amino-2-deoxy-D-galactopyranosyl-b(1,4)-2-acetamido-2-deoxy-glucopyranose (Compound 41b)

(12 Percent): $^1$H NMR for HCl salt (D$_2$O) δ: 2.022, 2.024 (s, NHAc of α and β anomer of GlcNAc), 3.17–3.23 (1H, m, H-2 of GalN), 4.67 (d, J 7.53 Hz, H-1b of GlcNAc), 5.13 (d, J 1.54 Hz, H-1a of GlcNAc). HRMS calcd for C$_{14}$H$_{26}$N$_2$O$_{10}$Na (M+Na$^+$) 405.1485, found 405.1489. $^1$H NMR of its acetate form is in good agreement with that reported. [Palcic et al., *Glycobiology*, 1:205 (1991)].

(e) Ethyl D-Galactopyranosyl-b(1,4)-2-azido-2-deoxy-D-glucopyranoside (Compound 41c)

In this case DTT was eliminated since 2-azido group was reduced to the corresponding amine with DTT. (15 percent): $^1$H NMR β anomer (D$_2$O) δ: 1.22 (1H, t, J 7.80 Hz, OCH$_2$CH$_3$), 3.27 (1H, J 8.33, 9.64 Hz, H-2 of GlcN$_3$), 4.40 (1H, d, J 7.81 Hz, H-1 of Gal), 4.55 (1H, H 8.24 Hz, H-1 of GlcN$_3$). HRMS calcd for C$_{14}$H$_{25}$N$_3$O$_{10}$Na (M+Na$^+$) 418.1438, found 418.1438.

The acceptor, ethyl 2-azido-2-deoxy-D-glucopyranoside was prepared as follows: Triacetyl-D-glucal was azidonitrated [Lemieux et al., *Can. J. Chem.*, 57:1244 (1979)] [NaN$_3$ and Ce(NH$_4$)$_2$(NO$_3$)$_6$ in CH$_3$CN] and acetolyzed (NaOAc in AcOH) to give 2-azido-1,3,4,6-tetra-O-acetyl-2-deoxy-D-glucopyranose, which was treated with TiBr$_4$ in CH$_2$Cl$_2$ and EtOAc, giving a glycosyl bromide, then glycosylated with EtOH in the presence of AgOTf and MS 4 Å in CH$_2$Cl$_2$ to give after O-deacetylation with NaOMe in MeOH, ethyl 2-azido-2-deoxy-D-glucopyranoside (22 percent overall yield) as a mixture of α and β 1:1.5. $^1$H NMR (D$_2$O) δ: 1.21 (t, J 7.80 Hz, OCH$_2$CH$_3$ of β anomer), 1.22 (t, J 7.80 Hz, OCH$_2$CH$_3$), 2.99 (dd, J 7.43, 9.83 Hz, H-2 of β anomer), 5.11 (d, J 3.58 Hz, H-1 of a anomer). HRMS calcd for C$_8$H$_{15}$N$_3$O$_5$Cs (M+Cs$^+$) 366.0066, found 366.0066.

Example 12

Sialylation (Scheme 16)

(a) Compound 42

A solution of Compound 1-$^{13}$C-41 (210 mg, 0.50 μmol), NeuAc (160 mg, 0.52 μmol), PEP Na$_3$ salt (120 mg, 0.51 mmol), MgCl$_2$.6H$_2$O (20 mg, 0.10 mmol), MnCl$_2$.4H$_2$O (4.9 mg, 0.025 mmol), KCl (7.5 mg, 0.10 mmol), CMP (16 mg, 0.05 mmol), ATP (2.7 mg, 0.005 μmol) and mercaptoethanol (0.34 mL) in HEPES buffer (200 mM, pH 7.5; 3.5 mL) was adjusted with N NaOH to pH 7.5 and the enzymes, NMK (5 U), PK (100 U), PPase (10 U), CMP-NeuAc synthetase (0.4 U) and α2,3SiaT (0.1 U) were added to the solution. The mixture was gently stirred under an argon atmosphere at room temperature (25° C.) for three days. The mixture was concentrated and the residue was chromatographed on silica gel, with EtOAc—iPrOH—H$_2$O (2:2:1), to give a trisaccharide, which was further purified with BioGel P-2, with water to give Compound 42 (88 mg, 24 percent). $^1$H NMR (D$_2$O) d 1.81 (1H, br t, J 12.02 Hz, H-3ax of NeuAc), 2.04 (6H, s, NHAC of GlcNAc and NeuAc), 2.76 (1H, dd, J 4.57, 12.33 Hz, H-3eq of NeuAc), 3.96 (1H, br d, J 3.10 Hz, H-4 of Gal), 4.13 (1H, dd, J 3.09, 9.94 Hz, H-3 of Gal), 4.56 (1H, dd, $J_{H-1,H-2}$ 7.83, $J_{H-1,13C}$ 162.78 Hz, H-1 of Gal), 4.58 (1H, d, J 8.32 Hz, H-1 of GlcNAc). HRMS calcd for C$_{27}$H$_{44}$N$_2$O$_{19}$Cs$_2$ (M–H$^+$+2Cs$^+$) 980.0759, found 980.0720.

(b) NeuAcα2.3'Lactal Compound 43 (82 mg)

$^1$H NMR (D$_2$O, 320° K) δ: 1.84 (1H, br t, J 12.18 Hz, H-3eq of NeuAc), 2.08 (3H, s, NHAC of NeuAc), 2.82 (1H, dd, J 4.46, 12.32 Hz, H-3eq of NeuAc), 4.01 (1H, br d, J 2.50 Hz, H-4 of Gal), 4.16 (1H, dd, J 2.50, 9.50 Hz, H-3 of Gal), 4.43 (1H, dt, J 1.18, 6.46 Hz, H-3 of Glucal), 4.65 (1H, d, J 7.86 Hz, H-1 of Gal), 4.88 (1H, dd, J 2.63, 6.07 Hz, H-2 of Glucal) and 6.51 (1H, dd, J 1.45, 6.08 Hz, H-1 of Glucal). HRMS calcd for C$_{23}$H$_{35}$NO$_{17}$NaCs$_2$ (M–H$^+$+2Cs$^+$) 864.0092, found 864.0066.

Example 13

Fucosylation (Scheme 17)

(a) Compounds 44, 45 and 46

A solution of FucT (0.02 U; 2 mL) was added to a solution of Compound 42 (23 mg, 0.031 mmol) and GDP-Fuc (Ichikawa et al., *J. Org. Chem.*, in press) (24 mg, 0.036 mmol) in HEPES buffer (3 mL; 200 mM, pH 7.5) containing 5 mM ATP, 20 mM Mn$^{2+}$. The mixture was gently stirred under an argon atmosphere for five days at room temperature (25° C.). A similar result was obtained using a solution containing Compound 42 (23 mg; 0.031 mmol) and GDP-Fuc (70 mg, 0.105 mmol) in HEPES buffer (1 mL; 200 mM, pH 7.4) containing $Mn^{2+}$ (20 mM) and an α1,3FucT solution (0.01 U) that was similarly manipulated. The mixture was concentrated and chromatographed on silica gel, with EtOAc—iPrOH—$H_2O$ (2:2:1), to give a tetrasaccharide, which was further purified with BioGel P-2, with water. The eluant was passed through a column of Dowex 50W-X8 [$H^+$], eluted with water to remove $Mn^{2+}$ cation, neutralized with N NaOH, and lyophilized to give Compound 44 (18 mg): similarly, Compounds 45 (42 mg) and 46 (51 mg) were similarly prepared.

Compound 44: 1H NMR ($D_2O$) δ: 1.11 (3H, d, J 6.61 Hz, 6-$CH_3$ of Fuc), 1.73 (1H, br t, J 12.04 Hz, H-3ax of NeuAc), 1.96 (3H, s, NHAc of GlcNAc), 1.97 (3H, s, NHAc of NeuAc), 2.69 (1H, dd, J 4.52, 12.38 Hz, H-3eq of NeuAc), 3.46 (1H, dt, J 7.00, 9.68 Hz, H-2 of Gal), 3.71 (1H br d, J 3.00 Hz, H-4 of Fuc), 4.02 (1H, dd, J 2.94, 9.78 Hz, H-3 of Gal), 4.46 (1H, dd, $J_{1,2}$ 7.90, $J_{13C,H}$ 162.13 Hz, H-1 of Gal), 4.52 (1H, d, J 8.41 Hz, H-1 of GlcNAc), 5.04 (1H, d, J 3.98 Hz, H-1 of Fuc).

Compound 45: 1H NMR ($D_2O$) δ: 1.17 (3H, d, J 6.61 Hz, 6-$CH_3$ of Fuc), 2.03 (3H, s, NHAc of GlcNAc), 3.50 (1H, ddd, J 6.47, 7.86, 9.86 Hz, H-2 of Gal), 3.80 (1H, br d, J 2.88 Hz, H-4 of Fuc), 4.46 (1H, dd, $J_{1,2}$ 7.79, $J_{13C,H}$ 161.45 Hz, H-1 of Gal), 4.59 (1H, d, J 8.44 Hz, H-1 of GlcNAc), 4.84 (1H, br q, J 7.50 Hz, H-5 of Fuc), 5.11 (1H, d, J 3.90 Hz, H-1 of Fuc).

Compound 46: $^1$H NMR ($D_2O$ at 320° K) δ: 1.11 (3H, d, J 6.61 Hz, 6-$CH_3$ of Fuc), 1.84 (1H, br t, J 12.00 Hz, H-3ax of NeuAc), 2.08 (3H, s, NHAc of NeuAc), 2.80 (1H, dd, J 4.52, 12.38 Hz, H-3eq of NeuAc), 4.49 (1H, br q, J 7.50 Hz, H-5 of Fuc), 4.64 (1H, d, J 8.0 Hz, H-1 of Gal), 5.02 (1H, dd, J 2.5, 6.0 Hz, H-2 of Glucal), 5.09 (1H, d, J 3.98 Hz, H-1 of Fuc), 6.51 (1H, dd, J 1.5, 6.0 Hz, H-1 of Glucal).

(b) Galβ1,4(Fucα1,3)-(5-thio)Glc

A solution of Galβ1,4(5-Thio)Glc (30 mg, 84 mmol), GDP-Fuc (60 mg, 84 mmol) and α1,3/4FucT (0.5 U) in Na cacodylate buffer (5.4 mL; 50 mM, pH 6.2) containing 5 mM ATP and 20 mM $MnCl_2$ was stirred for two days at room temperature. The $R_f$ values of the starting material and the product were 0.39 and 0.31, respectively, in EtOAc/AcOH/$H_2O$ 3:2:1 on silica TLC. The reaction mixture was applied directly to a column of Sephadex G-25 Superfine (1.5×30 cm), and eluted with water. The fractions containing the product were pooled and successively passed through columns of QAE-Sephadex and Dowex 50-X8 [$H^+$] with water. The effluent was pooled and lyophilized (21 mg). $^1$H NMR ($D_2O$, 20° C.) δ: 1.13 (3H, d, J=6.7 Hz, 6-$CH_3$ of Fuc), 3.40 (1H, dd, J=6.4 and 11.7 Hz), 3.60 (1H, dd, J=3.6 and 11.7 Hz), 4.52 (1H, d, J=7.9 Hz), 4.95 (1H, J=2.6 Hz, 5.34 (1H, d, J=3.8 Hz).

Example 14

Kinetic Study of Enzymes (a) For FucT

The assay procedure was essentially the same as described previously [Fukowska-Latallo et al, *Gene & Development*, 4:1288 (1990)] with some modifications. A stock mixture containing 0.25 mM GDP-$^{14}$C-Fuc (5000 cpm/mL), 6.25 mM ATP, 25 mM $MnCl_2$ and 62.5 mM sodium cacodylate buffer, pH 6.2 was mixed freshly and kept on ice. To this solution, FucT was added immediately before use, and the reaction was initiated by combining 16 μL of this mixture and 4 μL of 100 mM of acceptor (total incubation solution was 20 μL). The incubation was carried out at 37° C. for 30 to 240 minutes depending upon the acceptor under study. Separate assays in the absence of acceptor were used to correct for background hydrolysis of GDP-Fuc. Upon completion of incubation, 400 μL of a 25 percent (v/v) suspension of QAE-Sephadex was added. These suspensions were gently mixed at room temperature for 10 minutes before centrifugation at 13,000 rpm for one minute. From the supernatant fluid, 200 μL were extracted and mixed with 10 mL of scintillation cocktail. The radio-activity was counted on a scintillation counter. Care was taken to be sure less than 10 percent of the enzymatic reaction had taken place over the incubation period. This assay can be run in the absence of ATP.

(b) For GalT

Initial velocities of the enzyme reaction were determined by measuring the rate of LacNAc formation with a slight modification of the assay by Pierce et al. [Pierce et al., *Anal. Biochem.*, 102:441 (1980)]. All the reactions were carried out in 100 mM cacodylate buffer (pH 7.5) with fixed concentrations of $Mn^{2+}$ (9.3 mM) and UDP-Gal (0.1 mM; 58.5 cpm/pmol of UDP-$^{14}$C-Gal) in 100 mL of solution. The reaction was initiated by the addition of GalT (0.05 U, 120 mg protein; from Sigma) and permitted to stand at 20° C. for 30 minutes. Nonspecific hydrolysis of UDP-Gal was measured by the control reaction in the absence of GalT. The reaction was stopped by passing through a column of QAE-Sephadex (700 mL), and eluted by gentle air pressure to remove the unreacted UDP-Gal. The reaction vial was rinsed twice with 400 mL of water each and passed through the resin column. The filtrates were collected and directly transferred into a scintillation vial. The scintillation fluid was added to the vial, and then radioactivity was counted by a liquid scintillation counter. The data were analyzed by a double reciprocal plot to obtain $K_m$ (1.5 mM for GlcNAc) [a value of 1.3± 1 mM was reported in Palcic et al., *Carbohydr. Res.*, 159:315 (1987)] and $K_i$ (0.46±0.06 mM) for UDP. Similarly, $IC_{50}$ value of UDP for GalT was determined using different concentration of UDP.

Example 15

GDP-Fuc Generating Enzyme Used in Scheme 19

(a) Enzyme Preparation (GDP-Fuc S)

Bacterium, *Klebsiella pneumonia*, ATCC 12658 was grown in 2 L of the medium containing 10 g of casamino acid (Difco), 5 g of yeast extract, 3 g of $K_2$ $HPO_4$, 1 g of $KH_2PO_4$ and 5 g of D-glucose per liter (pH 7.0). After incubation at 37° C. for 18 hours, the cells were harvested by centrifugation (10,000×g, 50 minutes, 4° C.) and resuspended in 50 mM tris buffer containing 0.5 mM DTT. The cells were disrupted by a French press at 16,000 lb/in. The cell debris was removed by centrifugation at 23,000×g for 60 minutes and the supernatant (cell free extract) was used for enzyme purification. The cell free extract (50 mL) for a 2 L culture was treated with 60 mg of protamine sulfate and the resulting precipitate was removed after centrifugation. Solid ammonium sulfate was then added with slowly stirring until 70 percent saturation was reached (0.436 g/mL at zero degrees C.). After the centrifugation, the precipitate was collected and resuspended in 20 mL of the buffer (50 mM tris containing 0.5 mM DTT, pH 7.5) and dialyzed overnight at 4° C. in 4 L of the same buffer.

The remaining solution (20 mL) was then passed through a DEAE-Sepharose CL-6B column (Pharmacia) (3×30 cm) preequilibrated with the same buffer. The enzyme was eluted with a linear gradient of NaCl from 0 to 1 mM in the same buffer (total 400 mL). The active fractions were pooled and dialyzed in 2 L of 50 mM of tris buffer containing 0.5 mM of DTT (pH 7.5). This preparation of GDP-Fuc S enzyme was used for the preparation of GDP-Fuc. The activity was estimated about 0.05 U/mL based on IPLC and NADH oxidation assay.

(b) Enzymatic Preparation and Regeneration of GDP-Fuc from Man-1-P, Scheme 19

A solution of imidazole (10 mM), Man-1-P (10 mM), GDP (10 mM), PEP (10 mM), KF (5 mM), $Mg^{2+}$ (10 mM), KCl (20 mM), NADP (2 mM), EDTA (6 mM), iPrOH (2 percent), PK (80 U), TBDH (32 U), yeast cells (*S. cerevisae* 52 mg, freeze-dried from 50 mM Tris buffer, pH 7.5), GDP-Fuc S generating enzyme (400 mL) in HEPES buffer (pH 7.5) (the total solution volume 2 mL) was incubated at 37° C. under an argon atmosphere for 18 hours.

The HPLC column partisil 5 SAX (Whatman Co.), 0.46× 12.5 cm, with particle size 5 mm was used. The mobile phase was 0.1 M phosphate buffer (pH 3.5) with flow rate 0.5 mL/min (pressure 600 psi). The compounds were detected by a UV detector at 254 nm. The retention times for GDP-Man and GDP-Fuc were 9.92 and 13.4 minutes, respectively. GDP-Fuc (5 percent) and GDP-Man (30 percent) were formed based on the HPLC analysis.

A solution of Compound 41 or 42 (10 mM in 2 mL HEPES buffer pH 7.5, containing 5 mM ATP and 20 mM $MnCl_2$) was then added and the mixture was stirred for five days. TLC on silica gel plate: $R_f$=0.28 for Compound 45 and 0.50 for Compound 41 with EtOAc: AcOH: $H_2O$=4:2:1 (v/v) and 0.56 for Compound 44 and 0.63 for Compound 42 with 1M $NH_4OH$:iPrOH=1:2.4 (v/v). Compounds 45 and 44 (8 and 4 mg each) were isolated and purified as described above.

Example 16

Purification of GDP-fucose Pyrophosphorylase for Use in Scheme 20

(a) Enzyme Preparation

Porcine liver (4 kg) was homogenized in ice cold 10 mM MOPS, pH 7.5, with 1 mg/mL each antipain, aprotinin, chymostatin, leupeptin and pepstatin, in a Waring blender (five 15 second bursts on high setting). Cell debris was removed by centrifugation of 8000×g for 20 minutes at 4° C. To the supernatant fraction 1 L of a 2 percent solution of protamine sulfate was added. The mixture was stirred for five minutes, and the precipitate removed by centrifugation as above. Solid ammonium sulfate was slowly added to the supernatant fraction to 50 percent saturation (0.291 g/mL at zero degrees C. After centrifugation as described above, the precipitate was collected and resuspended in 1600 mL 1.2 M ammonium sulfate.

The sample was mixed with a slurry of phenyl Sepharose (250 mL) that had been equilibrated in 1.2 M ammonium sulfate. The resin with the bound enzyme was washed with 1.2 M ammonium sulfate (1.5 L) and the enzyme activity eluted with 0.4 M ammonium sulfate (750 mL). This process was repeated with the flow-through until the majority of the enzyme activity was removed from the sample. A portion of the phenyl Sepharose eluate (200 mL) was dialyzed against 10 mM MOPS, pH 7.5, and passed through a column of DEAE 5PW (15 cm×21.5 mm) equilibrated in the same buffer. Enzyme activity was observed in the material that flowed through the column, and was concentrated by means of an Amicon ultrafiltration device.

The sample was then subjected to gel filtration on a column of TSK Gel 3000 SW9 (30 cm×21.5 mm) equilibrated and run in 50 mM MOPS, pH 7.5 with 150 mM KCl. Active fractions were pooled and stored as a 50 percent ammonium sulfate slurry. Throughout the purification GDP-Fuc pyrophosphorylase was assayed according to the method of Ishihara and Health. [Ishihara et al., *J. Bioo. Chem.*, 243:1110 (1968)]. One unit of activity is defined as the incorporation of 1 mmol inorganic $^{32}P$-pyrophosphate into GTP per minute.

(b) GDP-Fucose Regeneration Employing GDP-Fucose Pyrophosphorylase, Scheme 20, Synthesis of Sialyl Lewis-x A solution of MOPS, pH 7.5 (50 mM), Fuc 1-P (10 mM), GDP (1 mM), PEP (10 mM), KF (5 mM), $Mg^{2+}$ (10 mM), $Mn^{2+}$ (10 mM), PK (5 U), sialyl-[3H]-LacNAcβ-O-$(CH_2)_6CO_2Me$ (10 mM), α1,3FucT (0.1 U), inorganic pyrophosphatase (5 U), and GDP-Fuc pyrophosphorylase (0.1 U) were mixed in a volume of 100 mL. The reaction was incubated on a tube turner at room temperature for 60 hours. Products were collected on a Sep-Pac C18 column and eluted with 50 percent methanol. The sample was dried by evaporation under reduced pressure, resuspended in water, and analyzed by thin layer chromatography on silica gel plates with isopropanol/1M ammonium acetate (6:1) as solvent. Sialyl Lewis x was formed with a yield of about 30 percent as determined by scintillation counting.

Example 17

(2R)-Methyl-(5S)-hydroxymethyl-(3R,4R)-dihydroxypyrollidine; (Compound 50)

A. Cis-2,3-epoxy-1,4-butane-diol

Cis-2,3-epoxy-1,4-butane-diol was prepared from 1,4-dihydroxy-2-butene according to the reported procedure [Nelson et al., *J. Med. Chem.*, 19:153 (1976) except that the reaction was carried out at room temperature for 36 hours.

B. 2-Azido-2-deoxy-threitol

A solution containing cis-2,3-epoxy-1,4-butane-diol (1.82 grams, 17.50 millimoles), sodium azide ($NaN_3$; 5.68 grams, 5 equivalents), and ammonium chloride ($NH_4Cl$; 4.68 grams, 5 equivalents) in 100 milliliters (mL) methanol and 12 mL $H_2O$ was heated at reflux for 24 hours. The solvent was removed under reduced pressure, then ethanol was added and the precipitate was filtered off. The precipitation procedure was repeated several times to remove excess $NaN_3$ and $NH_4Cl$, to thereby obtain 2-azido-2-deoxy-threitol as yellow liquid (90 percent: $R_f$=0.28 (EtOAc 100 percent); infrared (neat) 2109 $cm^{-1}$ ($—N_3$); $^1H$-NMR ($CD_3COCD_3$) δ3.49 (1H, m) 3.59 (3H, m), 3.79 (5H, m), 4.03 (1H, t, J=5.5 Hz), 4.19 (1H, d, J=5.5), 4.30 (1H, t, J=5.5 Hz) ppm. HRMS ($M+H^+$) calculated 148.0722, found 148.072.

C. 5-Azido-5-deoxy-L-xylo-hexulose-1-phosphate

A solution containing 2-azido-2-deoxy-threitol prepared above (476 milligrams, 3.24 millimoles) in 10 mL $H_2O$ was cooled to zero degrees C. and sodium periodate ($NaIO_4$; 762 milligrams, 1.1 equivalent) was added. After 10 minutes, the starting material disappeared completely and a new spot appeared according to thin layer chromatography ($R_f$=0.5, ethyl acetate). Barium chloride ($BaCl_2.2H_2O$; 870 milligrams, 1.1 equivalent) was then added to the solution and the precipitate was filtered off. The solution was acidified to pH 1 with Dowex 50 ($H^+$). Racemic 2-azido-3-hydroxypropionaldehyde, thus prepared was not isolated.

After filtration, the solution containing the racemate was adjusted to pH 7 with sodium hydroxide (NaOH; 10 normal). Dihydroxyacetone phosphate (1.5 millimoles) was then added and the solution was readjusted to pH 7 with 10 normal NaOH. To that solution, rabbit muscle FDP aldolase (500 units) was added and the solution was stirred slowly for 2 days. Enzymatic assay indicated that all of the DHAP had been consumed.

The title compound was first isolated as the barium salt by adding two equivalents $BaCl_2.2H_2O$ to the reaction mixture.

The solution was maintained at −20° C. overnight (about 18 hours). The precipitate was recovered, and treated with Dowex 50 (H⁺) in distilled water to remove barium cations. After filtration, the solution was adjusted to pH 7 and lyophilized to obtain the purified title compound (75 percent). $^1$H-NMR (D$_2$O) δ3.13 (1H, d, J=9.5 Hz, H-3), 3.14 (1H, ddd, J=9.5, 5, 11 Hz, H-5), 3.20 (1H, t, J=11 Hz, H-6a), 3.31 (1H, t, J=9.5 Hz, H-4), 3.37 (1H, dd, J=6, 11 Hz, H-6e), 3.40–3.44 (2H, m, 2×H-1) ppm. $^{13}$C-NMR (D$_2$O) δ61.78, 63.36, 67.35, 70.95, 97.67 (d, J=9.5 Hz) ppm. HRMS (M-4H⁺+5Na⁺) calculated 395.9540, found: 395.9538.

D. A solution of 5-azido-5-deoxy-L-xylo-hexulose-1-phosphate (100 milligrams, 0.35 millimoles) in 5 mL water was hydrogenated with 20 milligrams 10 percent palladium-carbon (Pd-C) under 40 pounds per square inch (psi) of hydrogen for one day. The catalyst was removed by filtration and the filtrate was concentrated in vacuo. The residue was chromatographed on silica gel column (methanol: chloroform: H$_2$O=6:4:2) to yield Compound 50 (40 milligrams, 78 percent yield, 2R:2S≈6:1). $^1$H-NMR (D$_2$O) δ1.31 (3H, d, J=7 Hz, 2R—CH$_3$), 1.27 (3H, d, J-6.5 Hz, 2S-CH$_3$), 3.36 (1H, m, H-2), 3.66 (1H, m, H-5), 3.74–3.81 (2H, m, 2×H-5), 3.85 (1H, m, H-3), 4.08 (1H, dd, J=2.5, 4.5 Hz, H-4) ppm; $^{13}$C-NMR (D2O) δ16.58 (C-2'), 57.90 (C-5'), 61.50, 63.44, 75.62, 87.09 ppm. HRMS (M+H⁺) calculated 148.0974, found 148.0974.

Example 18

Preparation of FucT Inhibitor Compounds 51–53

Inhibitor Compounds 51–53 were prepared generally as shown in Scheme 25, below

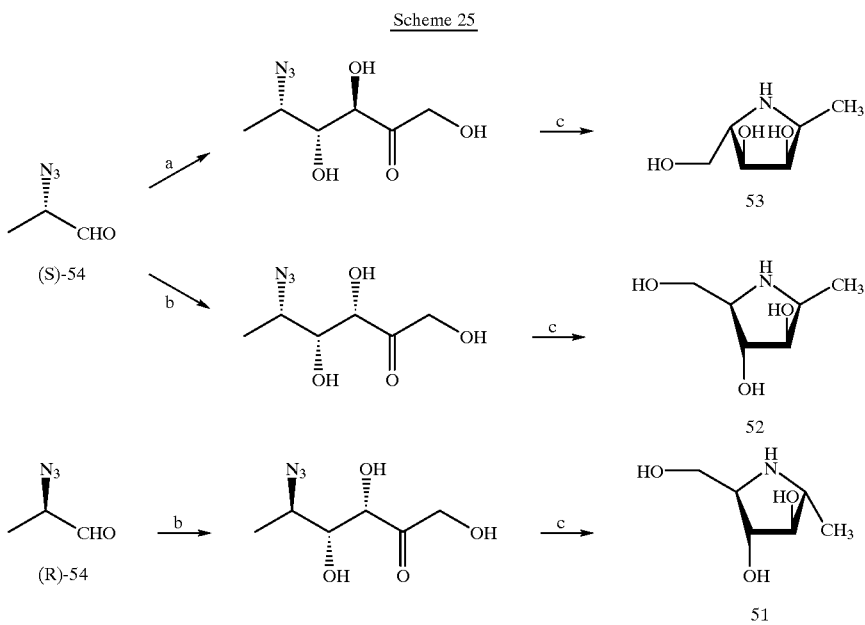

For the synthesis of Compounds 51–53, the azido-aldehydes (S)-54 and (R)-54 were chosen as acceptors for the adlolase-catalyzed reactions with dihydroxyacetone phosphate (step a, fuculose 1-phosphate aldolase; step b, rabbit muscle fructose-1,6-diphosphate aldolase to form intermediate phosphates that were first treated with acid phosphatose and then reductively aminated (step c; H$_2$/Pd—C, 50 psi) to form the final products that contained two additional chiral centers at the 3- and 4-positions.

Compounds (S)-54 and (R)-54 were prepared from 2-butyn-1-ol via reaction with Lindlar catalyst followed by epoxidation and azide opening to provide the corresponding enantiomeric 2- and 3-azidodiols in a 6:1 ratio, respectively. Resolution of the 2-azidodiol was then carried out using a lipase from Pseudomonas sp. and vinyl acetate as acylating agent [Wang et al., *J. Org. Chem.,* 53:3127 (1988); Wang et al., *J. Am. Chem. Soc.,* 110:7200 (1980)] to obtain the (2R,3S)-2-azido-3-hydroxy-4-acetate and the (2S,3R)-2-azido-3,4-diacetate in high optical purity as determined by $^1$H NMR in the presence of Eu(hfc)$_3$. The purified azidohydroxyacetate and azidodiacetate were separately hydrolyzed to form the respective diols that were then oxidatively cleaved with sodium periodate to form Compounds (S)-54 and (R)-54.

Physical data for Compounds 51–53 are provided below.

53:$[\alpha]_D^{25}$+21.8° (c=1.0, $CH_3OH$); Rf=0.20 ($CHCl_3$/$CH_3OH$/$H_2O$/$NH_4OH$=5/4/1/0.08); $^1$H NMR (500 MHz, $CD_3OD$/TMS): δ1.140 (3H, d, J=6 Hz, $CH_3$), 2.34–2.45 (1H, m, CHN), 2.47–2.55 (1H, m, CHN), 3.656 (1H, dd, J=4 Hz and 11 Hz, $CH_aO$), 3.744 (1H, dd, J=5 Hz and 11 Hz, $CH_bO$), 3.876 (1H, dd, J=5 Hz and 5 Hz, CHO), 4.268 (1H, dd, J=5 Hz and 8 Hz, CHO). $^{13}$C NMR (125 MHz, $CD_3OD$): δ12.98, 60.56, 65.24, 70.95, 72.14, 73.88. HRMS (M+H$^+$) calcd: 148.0974, found: 148.0968.

52:$[\alpha]_D^{25}$+22.7° (c=1.2, $CH_3OH$); Rf=0.19 ($CHCl_3$/$CH_3OH$/$H_2O$/$NH_4OH$=5/4/1/0.08); $^1$H NMR (500 MHz, $CD_3OD$/TMS): δ1.162 (3H, d, J=6.5 Hz, $CH_3$), 2.915 (1H, dt, J=4 and 4.5 Hz CHN), 3.213 (1H, dq, J=4 and 6.5 Hz, CHN), 3.650 (1H, dd, J=5 Hz and 11 Hz, $CH_aO$), 3.685 (1H, dd, J=5 Hz and 11 Hz, $CH_bO$), 3.741 (1H, dd, J=1.5 Hz and 4 Hz, CHO), 3.835 (1H, dd, J=1.5 Hz and 4 Hz, CHO). $^{13}$C NMR (125 MHz, $CD_3OD$): δ13.72, 57.85, 63.07, 68.60, 80.60, 81.54. HRMS (M+H$^+$) calcd: 148.0974, found: 148.0964.

51:$[\alpha]_D^{25}$+39.1° (c=0.8, $CH_3OH$); Rf=0.19 ($CHCl_3$/$CH_3OH$/$H_2O$/$NH_4OH$=5/4/1/0.08); $^1$H NMR (500 MHz, $CD_3OD$/TMS): δ1.193 (3H, d, J=6.5 Hz, $CH_3$), 2.920 (1H, dt, J=6.5 and 7.5 Hz, CHN), 2.982 (1H, ddd, J=4.5, 6.5 and 6.5 Hz, CHN), 3.500 (1H, dd, J=6.5 and 7.5 Hz, CHO), 3.572 (1H, dd, J=6 Hz and 11 Hz, $CH_aO$), 3.644 (1H, dd, J=4.5 Hz and 11 Hz, $CH_bO$), 3.751 (1H, dd, J=6.5 Hz and 6.5 Hz, CHO). $^{13}$C NMR (125 MHz, $CD_3OD$): δ18.83, 58.07, 63.61, 64.36, 79.88, 84.88. HRMS (M+H$^+$) calcd: 148.0974, found: 148.0971.

Example 19

Syntheses and Data for Compounds of Schemes 21–23

Compounds 61–99 and their syntheses have been discussed in relation to Schemes 21–23. Selected $^1$H NMR and HRMS data for compounds of those schemes are provided in Table 6–8 hereinafter. Specific synthetic details for exemplary compounds in addition to those already discussed are provided below.

The procedures described below were also applied to the other glycosyl-1-phosphate Compounds 89–95. The only modification occured at the purification step of Compounds 68, 69, 75 and 76. EtOAc was used as the eluent for Compounds 68 and 69, EtOAc: hexane (2:3) for Compound 75 and $CHCl_3$:EtOAc:MeOH (15:0.5:0.2) for Compound 76.

A. 2,3,4,6-Tetra-O-acetyl-D-glucose (Compound 71)

A solution of pentaacetate Compound 64 (5.0 g, 12.8 mmol) and $BnNH_2$ (19.2 mmol) in THF (30 mL) was maintained at room temperature overnight (about 18 hours). The mixture was diluted with cold water and extracted with $CHCl_3$ (3×50 mL). The combined organic layer was successively washed with ice-cold dilute HCl, saturated $NaHCO_3$, saturated NaCl and water, then dried over anhydrous $Na_2SO_4$, and concentrated in vacuo. The residual syrup was purified by silica gel chromatography with EtOAc/hexane (2:3) to give Compound 71 (3.80 g, 85 percent) as a 3:1 (α:β) mixture of anomers as judged by $^1$H-NMR ($CDCl_3$).

B. Dibenzylphosphinyl 2,3,4,6-tetra-O-acetyl-D-glucose phosphite (Compound 78)

Dibenzyl N,N-diethylphosphoramidite (0.86 g, 7.3 mmol) was added to a solution of Compound 71 (1.0 g, 2.9 mmol) and 1,2,4-triazole (0.8 g, 11.5 mmol) in anhydrous $CH_2Cl_2$, under nitrogen atmosphere at room temperature. The mixture was allowed to stir at room temperature for 1–2 hours before diluting with ether. The mixture was successively washed with ice-cold saturated $NaHCO_3$, saturated NaCl, and water, dried over anhydrous $Na_2SO_3$ and concentrated in vacuo. The residual syrup was chromatographed by silica gel with EtOAc/hexane (1:4) to give Compound 78 (1.73 g, 97 percent) as a mixture of (α:β) 1:4 by $^1$H NMR ($CDCl_3$).

C. Dibenzylphosphoryl 2,3,4,6-tetra-O-acetyl-D-glucose (Compound 25)

To a solution of Compound 78 (1.2 g, 2.2 mmol) in THF (50 mL) cooled to −78° C. with a dry ice-acetone bath was added dropwise 30 percent $H_2O_2$ (10 mL), and the mixture was allowed to warm up to room temperature, and stirred for 1.5 hours at room temperature. The mixture was diluted with ether and successively washed with ice-cold saturated $Na_2S_2O_3$, saturated $NaHCO_3$, saturated NaCl, and water. The organic phase was dried over anhydrous $Na_2SO_4$ and concentrated to give a α:β (1:4) mixture of Compound 85 (1.36 g, 98 percent) as judged by $^1$H-NMR ($CDCl_3$). This product was used for the next step without further purification.

D. Glucose-1-phosphate (Compound 92)

Compound 85 (1.0 g, 1.8 mmol) was hydrogenated (14.7 Psi) over 5 percent Pd/C (200 mg) in EtOH (30 mL) and 10 percent $NaHCO_3$ (20 mL) for 10 hours at room temperature. The mixture was filtered and the filtrate concentrated. The residue was treated with 1N NaOH (10 mL) at room temperature for 3 hours. The mixture was neutralized with ice-cold 1N AcOH to pH 7.5 and the insoluble material was removed by filtration. Alternatively, a solution of MeOH:$H_2O$ (1:1 v/v) in 10% $Et_3N$ was used instead of NaOH, so that the subsequent neutralization step was eliminated. The filtrate was concentrated, diluted with water, and passed through a column of Dowex 50W-X8 [Na$^+$] (1×15 cm) with water as the eluent. The appropriate fractions were pooled, and lyophilized to give Compound 92.

Occasionally, a small amount of dephosphorylated product was observed. It was removed by passing the diluted filtrate to a column of Dowex 1W-X8 [$HCO_2^-$] (1×30 cm). The column was first eluted with water to remove the neutral product, and then a linear gradient of $NH_4HCO_3$ (0.1 M–0.3 M) was applied to elute the desired product. The appropriate fractions were pooled and lyophilized. The lyophilized powder was dissolved in water (10 mL), cooled to zero degrees C., and neutralized to pH 7.0 with Dowex 50W-X8 [H$^+$] resin. The resin was filtered off and the filtrate was again lyophilized to yield Compound 92 (0.30 g, 59 percent) as a α:β (1:4) mixture as judged by $^1$H-NMR ($D_2O$).

E. Methyl 5-acetamido-4,7,8,9-tetra-O-acetyl-3,5-dideoxy-β-D-glycero-D-galacto-2-nonulopyranosonate (Compound 96)

This compound was prepared by the procedure of Marra et al., *Carbohydr. Res.*, 190:317 (1989). Alternatively, a mixture of methyl 2-chloro-5-acetamido-4,7,8,9-tetra-O-acetyl-3,5-dideoxy-β-D-glycero-D-galacto-2-nonulopyranosonate [Kuhn et al., *Chem. Ber.*, 99:611 (1966)] (0.67 g, 1.3 mmol) and silver carbonate (0.363 g, 1.3 mmol) in acetone (5 mL)—$H_2O$ (0.5 mL) was stirred for 10 hours at room temperature. The suspension was filtered by passing through a Celite™ 545 bed, and the filtrate was evaporated to dryness. The residue was diluted with chloroform, washed with water and brine, and then dried over sodium sulfate. The solution was evaporated in vacuo to give a crude material, which was chromatographed on a silica gel column (chloroform-methanol 25:1) to give Compound 96 (0.568 g, 88 percent) as white needles.

¹H-NMR (CDCl₃) δ: 1.90, 2.02, 2.03, 2.10, 2.14 (3H each, s, 4×OAc and NAc), 2.17 (1H, dd, J 5.04, 12.72 Hz, H-3eq), 2.29 (1H, dd, J 11.52, 12.72 Hz, H-3ax), 3.87 (3H, s, COOMe), 4.02 (1H, dd, J 7.04, 12.4 Hz, H-9), 4.12 (1H, dd, J 2.1, 7.8 Hz, H-6), 4.13 (1H, d, J 7.8 Hz, NH), 4.17 (1H, ddd, 7.8, 9.8, 10.28, Hz, H-5), 4.42 (1H, dd, J 1.92, 12.4 Hz, H-9'), 5.20–5.26 (2H, m, H-4 and H-8), 5.32 (1H, dd, J 2.1, 6.50 Hz, H-7), 5.37 (1H, bs, OH).

F. Methyl 5-acetamido-4,7,8,9-tetra-O-acetyl-2-(dibenzylphosphityl)-3,5-dideoxy-β-D-glycero-D-galacto-2-nonulopyranosonate (Compound 97)

Dibenzyl N,N-diethylphosphoamidate (0.25 g, 0.78 mmol) was added dropwise to a solution of Compoud 96 (0.166 g, 0.34 mmol) and 1H-tetrazole (0.10 g, 1.43 mmol) in THF (5 mL) under nitrogen atmosphere, and the mixture was maintained for four hours at room temperature. Dichloromethane (10 mL) was added to the mixture, and the organic phase was washed with ice-cold dilute HCl aqueous NaHCO₃, and ice-water, dried over anhydrous NaSO₄. The solution was evaporated in vacuo to give a crude material, which was chromatographed on a silica gel column with EtOAc/hexane (5:1) to give Compound 97 (0.17 g, 68 percent) as a colorless syrup. ¹³C-NMR (CDCl₃) δ: 20.7, 20.8, 20.9, 21.0, 23.1, 36.0, 49.5, 53.5, 62.6, 67.3, 67.4, 67.8, 69.3, 70.8, 94.8, 128.0, 128.7, 135.5, 141.8, 153.0, 169.1, 170.2, 170.4, 170.8, 171.0. HRMS: calcd for $C_{34}H_{42}NO_{15}PCS$ (M+Cs⁺) 868.1346, found 868.1346.

G. Methyl 5-acetamido-4,7,8,9-tetra-O-acetyl-2-(dibenzylphosphoryl)-3,5-dideoxy-β-D-glycero-D-galacto-2-nonulopyranosonate (Compound 98)

To a cooled solution of Compound 97 (0.13 g, 0.17 mmol) in THF (2 mL) was added t-BuO₂H (0.4 mL) at −10° C., and the mixture was allowed to warm up to room temperature, and stirred for one hour at room temperature. The mixture was diluted with CH₂Cl₂ and washed with ice-cold aqueous NaHCO₃ and water, then dried over anhydrous Na₂SO₄. The organic phase was evaporated in vacuo to give a crude material, which was chromatographed on a silica gel with CHCl₃/MeOH (25:1) to give Compound 98 (0.126 g, 95 percent) as a colorless syrup. HRMS: calcd for $C_{34}H_{42}NO_{16}PCs$ (M+Cs⁺) 884.1396; found, 884.1305.

H. Methyl 5-acetamido-4,7,8,9-tetra-O-acetyl-3,5-dideoxy-β-D-glycero-D-galacto-2-nonulopyranosaonate 2-phosphoric acid (Compound 99. Hydrogen form)

Compound 98 (0.22 g, 0.25 mmol) was hydrogenated (14.7 Psi) over 5 percent Pd/C (10 mg) under hydrogen atmosphere for 7 hours at room temperature. The catalyst was filtered off through a Celite™ 545 bed and the filtrate was concentrated in vacuo. The crude material was chromatographed on a silica gel column of reversed phase with CH₃CN/H₂O (5:1) to give Compound 99, hydrogen form (0.164 g, 99 percent) as a colorless syrup. HRMS: calcd for $C_{20}H_{30}NO_{16}PCs$ (M+Cs⁺) 704.0356, found 704.0356.

TABLE 6

Selected $^1$H NMR data of compounds$^a$ of Scheme 21

| | H-1α | H-1β | H-2 | H-3 | H-4 | H-5 | H-6a | H-6b | CH$_3$CO | CH$_3$CO$_2$ | CH$_3$CONH | CH$_3$CON |
|---|---|---|---|---|---|---|---|---|---|---|---|---|
| 68 | 5.32(t) $J_{2,3}$ 3.35 | — | 4.53(dt) $J_{2,3}$ 11.95 $J_{1,2}$ 10.30 | 5.26(dd) $J_{3,4}$ 3.20 | 5.39(dd) $J_{4,5}$ 0.80 | 4.45(t) $J_{5,6}$ 6.60 | 4.14 | 4.05(m) | 2.17, 2.06, 2.01, 2.00(4s) | | | |
| 69 | 5.30–5.28(m) | — | 4.32(dt) $J_{1,2}$ 4.20 $J_{2,3}$ 10.40 | 5.15(t) $J_{2,3}$ 10.40 | 5.30–5.28(m) | 4.15–4.13(m) | 4.22- | 4.20(dd) | 2.10, 2.04, 2.05, 1.97(4s) | | | |
| 70 | 5.52(brod) | n.d.$^b$ | 5.19(dd) $J_{1,2}$ 3.50 $J_{1,P}$ 8.80 | 5.41(dd) $J_{3,4}$ 3.40 | 5.48(dd) $J_{4,5}$ 1.25 | 4.72(dt) $J_{5,6a} = J_{5,6b}$ 6.50 | 4.12(dd) $J_{6a,6b}$ 11.50 | 4.08(dd) | 2.15, 2.10, 2.06, 1.99(4s) | | | |
| 71 | 5.47(d) $J_{1,2}$ 3.55 | 4.76(d) $J_{1,2}$ 9.00 | 4.90(dd) $J_{2,3}$ 10.25 | 5.54(t) $J_{3,4}$ 10.00 | 5.09(t) $J_{4,5}$ 10.50 | 4.29- | 4.22(m) | 4.17–4.12(m) | 2.10, 2.09 2.04, 2.02(4s) | | | |
| 72 | 5.23(brod) | — | 5.28(dd) $J_{1,2}$ 1.85 | 5.43(dd) $J_{3,4}$ 10.00 | 5.31(t) $J_{4,5}$ 10.00 | 4.29- | 4.23(m) | 4.16–4.12(m) | 2.17, 2.11, 2.06, 2.00(4s) | | | |
| 75$^c$ | 5.58(dd) $J_{1,2}$ 3.40 $J_{1,P}$ 7.75 | 5.46(t) $J_{1,2}$ 5.00 | 4.58(ddd) $J_{2,3}$ 11.50 $J_{2,P}$ 3.40 | 5.13–5.08(m) | 5.36(bd) $J_{3,4}$ 2.00 | 4.24(dt) $J_{4,5}$ 0.90 $J_{5,6a} = J_{5,6b}$ 6.50 | 4.06(dd) $J_{6a,6b}$ 11.30 | 3.94(dd) | | 2.15, 2.00, 1.96(3s) | 1.65(1s) | |
| 76$^d$ | 5.56(dd) $J_{1,2}$ 3.35 $J_{1,P}$ 7.80 | — | 4.35(ddd) $J_{2,3}$ 10.75 | 5.21(t) $J_{3,4}$ 10.00 | 5.13(t) $J_{4,5}$ 10.00 | 4.00(ddd) $J_{5,6a}$ 4.15 $J_{5,6b}$ 2.20 | 4.13(dd) $J_{6a,6b}$ 12.45 | 3.92(dd) | | 2.03, 2.02, 2.01(3s) | 1.62(1s) | |
| 77$^e$ | 5.82(dd) $J_{1,2}$ 3.40 $J_{1,P}$ 8.35 | 5.07(t) $J_{1,2}$ 8.20 | 5.35(dd) $J_{2,3}$ 10.50 | 5.05(dd) $J_{3,4}$ 3.45 | 5.41(dd) $J_{4,5}$ 1.00 | 3.97(dt) $J_{5,6a} = J_{5,6b}$ 6.85 | 4.16(dd) $J_{6a,6b}$ 11.50 | 4.12(dd) | | 2.17, 2.00, 1.99, 1.91(4s) | — | |
| 78$^e$ | 5.77(dd) $J_{1,2}$ 3.50 $J_{1,P}$ 8.33 | 5.15–4.85(m) | 5.15–4.85(m) | 5.23(t) $J_{2,3}=J_{3,4}$ 9.50 | 5.15–4.85(m) | 3.75(ddd) $J_{4,5}$ 10.00 $J_{5,6a}$ 5.00 $J_{5,6b}$ 2.00 | 4.24(dd) $J_{6a,6b}$ 12.50 | 4.10(dd) | | 2.032, 2.01, 1.90(4s) | — | |
| 79$^e$ | 5.50(dd) $J_{1,2}$ 1.50 $J_{1,P}$ 8.00 | n.d.$^b$ | 521(dd) $J_{2,3}$ 3.50 | 5.40(dd) $J_{4,5}$ 10.00 | 5.30(t) $J_{5,6a}$ 5.00 $J_{5,6b}$ 2.50 | 4.07(ddd) $J_{5,6a,6b}$ 12.50 | 420(dd) | 3.96(dd) | | 2.16, 2.05, 2.02, 2.01(4s) | — | |
| 82 | 5.72(dd) $J_{3,4}$ 3.15 $J_{4,5}$ 1.20 | — | 4.61(dddd) $J_{2,P}$ 3.50 $J_{2,3}$ 11.50 | 5.12–5.07(m) | 5.37(dd) | 4.24(dt) $J_{5,6a} = 3_{5,6b}$ 6.50 | 4.06(dd) 36a,6b 11.50 | 3.93(dd) | | 2.13, 1.98, 1.92(3s) | | 1.72(1s) |
| 83$^f$ | 5.67(dd) $J_{1,2}$ 3.30 $J_{1,P}$ 5.95 | — | 4.39–4.35(m) | 5.17- | 5.10(m) | 3.98(ddd) $J_{4,5}$ 10.00 | 4.13(dd) $J_{5,6a}$ 3.95 $J_{5,6b}$ 12.50 | 3.92(dd) $J_{5,6b}$ 2.25 | | 2.03, 2.02, 2.01(3s) | | 1.71(1s) |
| 84$^g$ | 5.96(dd) $J_{1,2}$ 3.40 $J_{1,P}$ 6.80 | 5.35–5.31(m) | 5.35–5.31(m) | 5.03(dd) $J_{3,4}$ 3.50 $J_{4,5}$ 10.00 | 5.42(dd) $J_{4,5}$ 0.85 | 4.03(dt) $J_{5,6a} = 3_{5,6b}$ 6.50 | 4.16(dd) $J_{6a,6b}$ 11.30 | 4.09(dd) | | 2.18, 1.99, 1.97, 1.92(4s) | — | |
| 85$^g$ | 5.91(dd) $J_{1,2}$ 3.30 $J_{1,P}$ 7.50 | 5.35(t) $J_{1,2}=J_{1,P}$ 7.50 | 5.13–5.08(m) | 5.22(t) $J_{3,4}$ 9.50 | 5.15–5.09(m) | 3.81(ddd) $J_{4,5}$ 10.95 $J_{5,6a}$ 5.00 $J_{5,6b}$ 2.00 | 4.24(dd) $J_{6a,6b}$ 12.50 | 4.12(dd) | | 2.04, 2.01, 2.00, 1.90(4s) | — | |
| 86 | 5.61(dd) $J_{1,2}$ 1.80 $J_{1,P}$ 6.40 | 5.44(dd) $J_{1,2}$ 1.50 $J_{1,P}$ 6.80 | 5.23(t) $J_{2,3}$ 2.80 | 5.30- | 5.28(m) | 4.04(ddd) $J_{4,5}$ 9.00 $J_{5,6a}$ 4.60 $J_{5,6b}$ 2.30 | 4.18(dd) $J_{6a,6b}$ 12.45 | 3.92(dd) | | 2.14, 2.03, 3.00, 1.99(4s) | — | |
| 89 | 5.33(dd) | — | 4.14(ddd) | 3.89(dd) | 395(bd) | 4.16(ddd) | 373(dd) | 3.68(dd) | | | | 2.02(ls) |

TABLE 6-continued

Selected $^1$H NMR data of compounds$^a$ of Scheme 21

| | H-1α | H-1β | H-2 | H-3 | H-4 | H-5 | H-6a | H-6b | CH$_3$CO | CH$_3$CO$_2$ | CH$_3$CONH | CH$_3$CON |
|---|---|---|---|---|---|---|---|---|---|---|---|---|
| 90 | $J_{1,2}$ 3.60<br>$J_{1,P}$ 7.55<br>534(dd)<br>$J_{1,2}$ 3.30<br>$J_{1,P}$ 755 | — | $J_{2,3}$ 10.85<br>$J_{2,P}$ 1.50<br>3.90(ddd)<br>$J_{2,3}$ 8.50<br>$J_{2,P}$ 2.00 | $J_{3,4}$ 3.20<br>3.77(dd)<br>$J_{3,4}$ 10.50 | 347(t)<br>$J_{4,5}$ 9.50 | $J_{5,6a}$ 7.60<br>$J_{5,6b}$ 4.55<br>3.92(ddd)<br>$J_{5,6a}$ 2.50<br>$J_{5,6b}$ 5.00 | $J_{6a,6b}$ 1.65<br>386(dd)<br>$J_{6a,6b}$ 12.50 | 3.76(dd) | | | | 2.04(ls) |
| 91 | 5.44(dd)<br>$J_{1,2}$ 3.65<br>$J_{1,P}$ 7.40 | 4.78(t)<br>$J_{1,2}$ = $J_{1,P}$<br>9.22 | 347(dd)<br>$J_{2,3}$ 11.50 | 3.62(dd)<br>$J_{3,4}$ 3.75 | 383(bd) | 3.67- | 3.65(m) | 3.74(dd)<br>$J_{5,6b}$ 10.00<br>$J_{6a,6b}$ 12.50 | | | | — |
| 92 | 5.42(dd)<br>$J_{1,2}$ 3.60<br>$J_{1,P}$ 7.60 | 4.86(t)<br>$J_{1,2}$ = $J_{1,P}$<br>7.75 | 3.27(t)<br>$J_{2,3}$ 8.50 | 3.49(t)<br>$J_{3,4}$ 9.45 | 3.30(t)<br>$J_{4,5}$ 9.50 | 3.48–3.45(m) | 3.87(dd)<br>$J_{5,6a}$ 1.50<br>$J_{6a,6b}$ 12.50 | 3.64(dd)<br>$J_{5,6b}$ 7.00 | | | | — |
| 93 | 5.27(dd)<br>$J_{1,2}$ 1.65<br>$J_{1,P}$ 8.73 | 5.11(dd)<br>$J_{1,2}$ 1.50<br>$J_{1,P}$ 8.90 | 3.89–3.81(m) | 3.54(t)<br>$J_{2,3}$ = $J_{3,4}$<br>10.00 | 3.89–3.81(m) | 367(dd)<br>$J_{4,5}$ 12.50<br>$J_{5,6a}$ = $J_{5,6b}$<br>6.78 | 3.89- | 3.81(m) | | | | — | a: chemical shift in p.p.m. and coupling constant (J) in Hz
b: not determined due to spectral overlap
c: HRMS calcd for C$_{28}$H$_{34}$PO$_{11}$NCs(M + Cs$^+$) 724.0924, found, 724.0931.
d: HRMS calcd for C$_{28}$H$_{34}$PO$_{11}$NNa(M + Na$^+$) 614.1767, found, 614.1798.
e: HRMS calcd for C$_{28}$H$_{33}$PO$_{12}$Cs(M + Cs$^+$) 725.0764, found, 725.0764 for 77, 725.0760 for 78, 725.0766 for 79.
f: The $^1$H-NMR data were in good agreement with those reported.
g: The $^1$H-NMR data were in good agreement with those reported.

TABLE 7

Selected 1H NMR data of compounds[a] of Scheme 22

| | H-1α | H-1β | H-2 | H-3 | H-4 | H-5 | CH₃ | CH₃CO₂ |
|---|---|---|---|---|---|---|---|---|
| 73 | 5.17(dd) $J_{1,2}$ 1.78 $J_{1,OH}$ 3.89 | n.d.[b] | 529(dd) $J_{2,3}$ 3.42 | 528(dd) $J_{3,4}$ 10.08 | 5.09(t) J4,5 9.98 | 4.15–4.09(m) | 1.23(d) $J_{5,CH3}$ 6.18 | 2.16, 2.06, 2.00(3s) |
| 30[c] | 423(dd) $J_{1,2}$ 1.80 $J_{1,P}$ 7.80 | n.d.[b] | 522(dd) $J_{2,3}$ 3.40 | 536(dd) $J_{3,4}$ 10.20 | 5.08(t) $J_{4,5}$ 10.00 | 4.02–3.98(m) | 1.14(d) $J_{5\text{-}CH3}$ 6.25 | 2.15, 2.05, 2.00(3s) |
| 87[d] | 5.55(dd) $J_{1,2}$ 1.60 $J_{1,P}$ 6.35 | 5.40(dd) $J_{1,2}$ 1.05 $J_{1,P}$ 7.45 | 523(dd) $J_{2,3}$ 3.50 | 516(dd) $J_{3,4}$ 9.50 | 5.11–5.08(m) | 3.99–3.93(m) | 1.11(d) $J_{5,CH3}$ 6.25 | 2.14, 2.05. 1.99(3s) |
| 94 | 520(dd) $J_{1,2}$ 2.00 $J_{1,P}$ 8.30 | 5.00(dd) $J_{1,2}$ 0.90 $J_{1,P}$ 8.75 | 3.91(dd) $J_{2,3}$ 3.35 | 386(dd) $J_{3,4}$ 8.90 | 3.35(t) $J_{4,5}$ 9.75 | 3.40–3.30(m) | 1.22(d) $J_{5,CH3}$ 6.30 | — |

[a]: chemical shift in p.p.m. and coupling constant (J) in Hz.
[b]: not determined due to spectral overlap.
[c]: HRMS calcd for C₂₆H₃₁PO₁₀Cs (M + Cs⁺) 557.1553, found, 557.1542.
[d]: The ¹H-NMR data were in good agreement with those reported.

TABLE 8

Selected ¹H NMR data of compounds[a] of Scheme 23

| | H-3eq | H-4 | H-5 | H-6 | H-7 | H-8 | H-9a | H-9b | COOMe | CH₃COO |
|---|---|---|---|---|---|---|---|---|---|---|
| 97[b] | 239(dd) $J_{3eq,4}$ 4.90 $J_{3eq,3ax}$ 13.00 | 4.83–4.91(m) | 3.99(ddd) $J_{5,NH}=J_{4,5}$ 10.40 | 3.74(dd) $J_{5,6}$ 10.60 $J_{6,7}$ 2.00 | 5.14(dd) $J_{7,8}$ 2.40 | 4.83–4.91(m) | 4.10(dd) $J_{8,9a}$ 7.40 $J_{9a,9b}$ 12.40 | 457(dd) $J_{8,9b}$ 2.00 | 3.73(s) | 1.96. 2.01, 2.06, 2.07(4s) |
| 98[b] | 2.60(dd) $J_{3eq,4}$ 4.90 $J_{3eq,3ax}$ 13.40 | 4.98–5.04(m) | 4.12(ddd) $J_{5,NH}=J_{4,5}$ 9.60 | 4.07(dd) $J_{5,6}$ 10.60 $J_{6,7}$ 2.00 | 532(dd) $J_{7,3}$ 2.00 | 530(ddd) | 4.23(dd) $J_{8,9a}$ 2.40 $J_{8,9b}$ 7.60 | 4.60(dd) $J_{9a,9b}$ 12.30 | 3.67(s) | 1.99, 2.00, 2.05, 2.12(4s) |
| 99[b] | 2.73(dd) $J_{3eq,4}$ 4.80 $J_{3eq,3ax}$ 13.00 | 5.40(ddd) $J_{3ax,4}$ 10.40 $J_{4,5}$ 10.80 | 3.88(dd) $J_{5,6}$ 10.40 | 452(dd) $J_{6,7}$ 2.12 | 545(dd) $J_{7,8}$ 2.16 | 5.30–5.34(m) | 4.40(dd) $J_{8,9a}$ 6.00 $J_{9a,9b}$ 12.60 | 454(dd) $J_{8,9b}$ 3.00 | 3.80(s) | 2.03, 2.09, 2.13, 2.15(4s) |

[a]: chemical shift in p.p.m. and coupling constant (J) in Hz
[b]: chemical shift of CH₃CON for 97 = 1.79(s); 98 = 1.87(s); 99 = 1.89(s)

The foregoing description and the examples are intended as illustrative and are not to be taken as limiting. Still other variations within the spirit and scope of this invention are possible and will readily present themselves to those skilled in the art.

What is claimed is:

1. A method of producing a fucosylated carbohydrate in a single reaction mixture comprising the steps of:
   (a) using a fucosyltransferase to form an O-glycosidic bond between a nucleoside 5'-diphospho-fucose and an available hydroxyl group of a carbohydrate acceptor molecule to yield a fucosylated carbohydrate and a nucleoside 5'-diphosphate, and;
   (b) recycling in situ the nucleoside 5'-diphosphate to form the corresponding nucleoside 5'-diphospho-fucose.

2. The method of claim 1 wherein the base of the nucleoside is guanine.

3. The method of claim 1 wherein the nucleoside 5'-diphosphate is present in a catalytic amount.

4. The method of claim 1 wherein the hydroxyl group of the carbohydrate acceptor molecule is a part of an N-acetylglucosamine, galactose or N-acetylgalactosamine.

5. The method of claim 1 wherein the carbohydrate acceptor molecule is sialylated.

6. A method for producing a fucosylated sialylated carbohydrate molecule through enzymatic formation of glycosidic linkages in a single reaction mixture comprising:
   (a) forming a first glycosidic linkage between an diphosphonucleoside-activated glycosyl donor and an available hydroxyl group of a carbohydrate acceptor molecule using a first glycosyltransferase;
   (b) forming a second glycosidic linkage between a monophosphonucleoside-activated sialyl donor and an available hydroxyl group of the carbohydrate acceptor molecule using a sialyltransferase; and
   (c) forming a third glycosidic linkage between a diphosphonucleoside-activated fucosyl donor and an available hydroxyl group of the carbohydrate acceptor molecule using a fucosyltransferase to yield a fucosylated carbohydrate acceptor and a nucleoside 5'-diphosphate, with in situ recycling of said nucleoside 5'-diphosphate to form more of said diphosphonucleoside-activated fucosyl donor, said glycosidic linkages of steps (a), (b) and (c) being formed in a single reaction mixture.

7. The method of claim 6 wherein the fucosylated sialylated carbohydrate moiety is a sialylated Lewis ligand.

8. The method of claim 7 wherein the sialylated Lewis ligand is SLe$^x$ or SLe$^a$.

9. The method of claim 6 wherein the fucose is transferred from a fucosyl donor to a hydroxyl group of a N-acetylglucosamine residue of the carbohydrate acceptor molecule.

10. The method of claim 9 wherein the fucosyl donor transfers fucose to a hydroxyl group of carbon 3 of the N-acetylglucosamine.

11. The method of claim 6 wherein the fucosyl donor transfers fucose to a hydroxyl group of a galactose residue of the carbohydrate acceptor molecule.

12. The method of claim 6 wherein the sialyltransferase is selected from the group consisting of α2,3 sialyltransferase, α2,4 sialyltransferase, α2,6 sialyltransferase and α2,8 sialytransferase.

13. The method of claim 6 wherein the fucosyltranferase is selected from the group consisting of α1,2 fucosyltransferase, α1,3 fucosyltransferase; α1,6 fucosyltransferase, α1,4 fucosyltransferase and α1,3/4 fucosyltransferase.

14. The method of claim 6 wherein the fucosyltransferase is selected from the group consisting of β-galactosidase α1,2 fucosyltransferase, N-acetylglucosamine α1,3 fucosyltransferase, N-acetylglucosamine α1,4 fucosyltransferase, N-acetylglucosamine α1,6 fucosyltransferase and N-acetylglucosamine α1,3/4 fucosyltransferease.

15. The method of claim 6 wherein the carbohydrate acceptor molecule is a carbohydrate substituted molecule wherein the carbohydrate terminates in a Galβ1,4GlcNAc-X where X is an organic molecule.

16. The method of claim 6 wherein the base of at least one nucleoside is either cytidine or uridine.

17. The method of claim 6 wherein the monophosphonucleoside-activated sialyl donor is cytidine 5'-monophospho-N-acetylneuraminic acid.

18. The method of claim 6 wherein the diphosphonucleoside-activated fucosyl donor is guanosine 5'-diphospho-fucose.

19. The method of claim 6 wherein the glycosyl donor of step (a) is a diphosphonucleoside-activated galactosyl donor that is uridine 5'-diphospho-galactose.

20. The method of claim 6 wherein steps (a) and (b) are substantially completed before step (c) is begun.

\* \* \* \* \*